United States Patent
Schatte et al.

(10) Patent No.: US 11,174,502 B2
(45) Date of Patent: *Nov. 16, 2021

(54) TRANSAMIDATION REACTION IN DEEP EUTECTIC SOLVENTS

(71) Applicant: Hoffmann-La Roche Inc., Little Falls, NJ (US)

(72) Inventors: Martin Schatte, Karlsbad (DE); Mara Boenitz-Dulat, Tutzing (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/933,779

(22) Filed: Mar. 23, 2018

(65) Prior Publication Data

US 2019/0040436 A1 Feb. 7, 2019

Related U.S. Application Data

(63) Continuation of application No. PCT/EP2016/072510, filed on Sep. 22, 2016.

(30) Foreign Application Priority Data

Sep. 25, 2015 (EP) .................... 15186955
Jun. 2, 2016 (EP) .................... 16172623

(51) Int. Cl.
*C12P 21/02* (2006.01)

(52) U.S. Cl.
CPC ......... *C12P 21/02* (2013.01); *C12Y 304/2207* (2013.01)

(58) Field of Classification Search
None
See application file for complete search history.

(56) References Cited

U.S. PATENT DOCUMENTS

| | | | |
|---|---|---|---|
| 8,247,198 B2 | 8/2012 | Gorke et al. | |
| 10,864,277 B2 | 12/2020 | Grawunder et al. | |
| 2009/0117628 A1* | 5/2009 | Gorke ...................... | C12N 9/00 435/129 |
| 2014/0030697 A1 | 1/2014 | Ploegh et al. | |
| 2014/0057317 A1 | 2/2014 | Liu et al. | |
| 2015/0152134 A1 | 6/2015 | Pentelute et al. | |
| 2016/0082046 A1 | 3/2016 | Lodish et al. | |
| 2016/0193355 A1 | 7/2016 | Qin et al. | |

FOREIGN PATENT DOCUMENTS

| | | |
|---|---|---|
| WO | 02/059148 | 8/2002 |
| WO | 2007/140371 A2 | 12/2007 |
| WO | 2010/099536 A3 | 2/2010 |
| WO | 2010/087994 A2 | 8/2010 |
| WO | 2010/099536 A2 | 9/2010 |
| WO | 2012/145522 | 10/2012 |
| WO | 2013/003555 A1 | 1/2013 |
| WO | 2013/016653 A1 | 1/2013 |
| WO | 2013/1533203 | 10/2013 |
| WO | 2013/177231 | 11/2013 |
| WO | 2014/001324 A1 | 1/2014 |
| WO | 2014/001325 A1 | 1/2014 |
| WO | 2014/055936 | 4/2014 |
| WO | 2014/177042 | 6/2014 |
| WO | 2014/131906 A1 | 9/2014 |
| WO | 2014/145441 | 9/2014 |
| WO | 2014/183066 A2 | 11/2014 |

OTHER PUBLICATIONS

Maugeri Z et al. Chymotrypsin-Catalyzed Peptide Synthesis in Deep Eutectic Solvents. 2013. European Journal of Organic Chemistry. p. 4223-4228. (Year: 2013).*
ISR of PCT/EP2016/072510 (dated Nov. 15, 2016).
Race et al., "Crystal Structure of *Streptococcus pyogenes* Sortase A Implications for Sortase Mechanism" Journal of Biological Chemistry 284:6924-6933 (2009).
Schmohl et al., "Sortase-mediated ligations for the site-specific modification of proteins" Current Opinion in Chemical Biology 22:122-128 (2014).
Zhao et al., "Protease activation in glycerol-based deep eutectic solvents" J Mol Catal B Enzym. 72:163-167 (2011).
Abbot et al., "Processing of Leather Using Deep Eutectic Solvents" CA Sustainable Chem Eng. 3(6): 1241-1247 (2015).
Antos et al., "Site-Specific N- and C-Terminal Labeling of a Single Polypeptide Using Sortases of Different Specificity" Journal of the American Chemical Society 131:10800-10801 (2009).
Antos, John M., et al., "Supporting Information" Title: Site-specific N- and C-terminal labeling of a single polypeptide using sortases of diffrent specificity, Whitehead Institute for Biomedical Research, 9 Cambridge Center, Cambridge, MA 02142, pp. S1-S20 (2009).
Biswas et al., "Sorting of LPXTG Peptides by Archetypal Sortases A: Role of Invariant Substrate Residues in Modulating the Enzyme Dynamics and Conformational Signature of a Productive Substrate" Biochemistry 53(15):2515-2524 (2014)
Branden et al. Introduction to Protein Structure "Prediction, Engineereing, and Design of Protein Structures" New York: Garland Publishing Inc., :247 (1991).

(Continued)

*Primary Examiner* — Paul J Holland
(74) *Attorney, Agent, or Firm* — Nicole Fortune

(57) ABSTRACT

Herein is reported a method for the enzymatic production of a polypeptide comprising the step of incubating i) a first polypeptide comprising the amino acid sequence LPXTG (SEQ ID NO: 01, wherein X can be any amino acid residue) or LPXTA (SEQ ID NO: 41, wherein X can be any amino acid residue), ii) a second polypeptide that has i) a glycinyl, an alaninyl, or a cysteinyl compound at its N-terminus, or ii) an oligoglycine, or oligoalanine, or a cysteine amino acid residue followed by one to three glycine or alanine amino acid residues at its N-terminus, or iii) a lysine amino acid residue within its 5 N-terminal amino acid residues, and iii) a third polypeptide with sortase A activity, in a deep eutectic solvent and thereby producing a polypeptide.

10 Claims, 18 Drawing Sheets

Specification includes a Sequence Listing.

(56) References Cited

OTHER PUBLICATIONS

Clancy et al., "Sortase transpeptidases: Insights into mechanism, substrate specificity, and inhibition" Biopolymers 94(4): 385-396 (2010).
Dai et al. Natural Deep Eutectic Solvents and Their Application in Natural Product Research and Development, Dissertation "3" Universiteit Leiden, (2013).
Frankel et al., "*Staphylococcus aureus* Sortase Transpeptidase SrtA: Insight into the Kinetic Mechanism and Evidence for a Reverse Protonation Catalytic Mechanism" Biochemistry 44(33):11188-11200 (2005).
Gaspar et al., "Baccillus anthracis Sortase A (SrtA) Anchors LPXTG Motif-Containing Surface Proteins to the Cell Wall Envelope" J of Bacteriology:4646-4655 (2005).
Heck et al., "Continuous Monitoring of Enzymatic Reactions on Surfaces by Real-Time Flow Cytometry: Sortase A Catalyzed Protein Immobilization as a Case Study" Bioconjugate Chemistry 25(8):1492-1500 (2014).
Hess et al., "M13 Bacteriophage Display Framework that Allows Sortase-Mediated Modification of Surface-Accessible Phage Proteins" Bioconjugate Chemistry 23:1478-1487 (2012).
International Search Report for PCT/EP2015/079692 dated Mar. 16, 2016.
International Search Report of PCT/EP2015/079615 dated Mar. 14, 2016.
ISR and Written Opinion of PCT/EP2016/072512 (dated Nov. 17, 2016).
ISR for PCT/EP2017/052318 (dated May 4, 2017).
Levary et al., "Protein-Protein Fusion Catalyzed by Sortase A" PLoS ONE 6(4 SUPPL e18342):1-6 (2011).
Li et al., "A novel reporter system monitoring Sortase A catalyzed protein ligation efficiency" Chinese Journal of Biotechnology 30(2):284-293 (2014).
Li et al., "Irreversible Site-Specific Hydrazinolysis of Proteins by Use of Sortase" Angewandte Chemie International Edition in English 53:2198-2202 (2014).
Ling et al., "Protein Thioester Synthesis Enabled by Sortase" J. Am. Chem. Soc. 134:10749-10752 (2012).
Madej et al., "Engineering of an Anti-Epidermal Growth Factor Receptor Antibody to Single Chain format and Labeling by Sortase A-Mediated Protein Ligation" Biotechnology and Bioengineering 109(6):1461-1470 (2012).
Marraffini et al., "Anchoring of Surface Proteins to the Cell Wall of *Staphylococcus aureus*" Journal of Biological Chemistry 279(36):37763-37770 (Sep. 3, 2004).
Marraffini et al., "Sortases and the Art of Anchoring Proteins to the Envelopes of Gram-Positive Bacteria" Microbiology and Molecular Biology Reviews 70:192-221 (2006).
Marvin et al., "Recombinant approaches to IgG-like bispecific antibodies" Acta Pharmacologica Sinica 26(6):649-658 (Jun. 2005).
Matsumoto et al., "Site-Specific Tetrameric Streptavidin-Protein Conjugation Using Sortase A" Journal of Biotechnology 152:37-42 (2011).
Matsumoto et al., "Sortase A-Catalyzed Site-Specific Coimmobilization on Microparticles via Streptavidin" Langmuir 28(7):3553-3557 (2012).
Meissner, P. et al. et al., "Transient gene expression: recombinant protein production with suspension-adapted HEK293-EBNA cells" Biotechnol. Bioeng 75:197-203 (2001).
NCBI Database, 002984641.1, (sortase SrtA [*Streptococcus pyogenes*]) pp. PN 171203 May 2013.
NCBI Database, 031862293.1, (sortase A [*Staphylococcus aureus*]), pp. PN 171203 Sep. 2014.
Oteng-Pabi et al., "Continuous enzyme-coupled assay for microbial transglutaminase activity" Analytical Biochemistry 441(2):169-173 (2013).
Popp et al., "Making and Breaking Peptide Bonds: Protein Engineering Using Sortase" Agnew. Chem. Int. Ed. 50:5024-5032 (2011).
Popp et al., "Sortase-catalyzed transformations that improve the properties of cytokines" PNAS 108:3169-3174 (2011).

Sadowski et al., "The sequence-structure relationship and protein function prediction" Current Opinion in Structural Biology 19:357-362 (2009).
Seffernick, J. et al., "Melamine Deaminases and Atrazine Chlorohydrolase: 98 Percent Indentical but Functionally Different" Journal of Bacteriology 183(8):2405-2410 (2001).
Smith et al., "Deep Eutectic Solvents (DESs) and Their Applications" Chemical Reviews 114:11060-11082 (2014).
Strijbis, K. et al., "Protein Ligation in Living Cells Using Sortase" Traffic 13:780-789 (2012).
Ta et al., "Enzymatic Single-Chain Antibody Tagging A Universal Approach to Targeted Molecular Imaging and Cell Homing in Cardiovascular Disease" Circulation Research 109:365-373 (2011).
Tan et al., "Applications of Transpeptidase Sortase A for Protein Modifications" Progress in Chemsitry 26(10):1741-1751 (2014).
Tang et al., "Identification of Dehalobacter reductive dehalogenases that catalyse dechlorination of chloroform, 1,1,1-trichloroethlane and 1,1-dichloroethane" Philosophical Transactions of The Royal Society B 368:1-10 (2013).
Ton-That et al., "Anchoring of Surface Proteins to the Cell Wall of *Staphylococcus aureus*" Journal of Biological Chemistry 277(9):7447-7452 (2002).
Ton-That et al., "Anchoring of surface proteins to the cell wall of *Staphylococcus aureus*. Sortase catalyzed in vitro transpeptidation reaction using LPXTG peptide and NH(2)-Gly(3) substrates" The Journal of biological chemistry 275(13):9876-81 (2000).
Ton-That et al., "Purification and Characterization for Sortase, the Transpeptidase that Cleaves Surface Proteins of *Staphylococcus aureus* at the LPXTG Motif" PNAS 96(22):12424-12429 (Oct. 26, 1999).
Tsukiji et al., "Sortase-Mediated Ligation: A Gift from Gram-Positive Bacteria to Protein Engineering" ChemBioChem 10:787-798 (2009).
Walsh, Christopher Antibiotics: actions, origins, resistance Washington D.C.: ASM Press, (2003).
Witkiowski, A. et al., "Conversion of a â- Ketoacyl Synthase to a Malonyl Decarbozylase by Replacement of the Active-Site Cysteine with Glutamine" Biochemistry 38:11643-11650 (1999).
Written Opinion for PCT/EP2017/052318.
Yamamura et al., "Enhancement of Sortase A-Mediated Protein Ligation by Inducing a beta-Hairpin Structure around the Ligation Site" Chem. Commun. 47:4742-4744 (2011).
Clancy et al., "Sortase Transpeptidases: Insights into mechanism, substrate specificity and inhibition" Peptide Science 94(4): 385-396 (2010).
Durand et al., "Deep eutectic solvents: Synthesis, application, and focus on lipase-catalyzed reactions" Eur. J. Lipid Sci. Technol. 115-379-385 (2013).
Garandeau et al., "The Sortase SrtA of Listeria monocytogenes Is Involved in Processing of Internalin and in Virulence" Infection and Immunity: 1382-1390 (Mar. 2002).
Garcia et al., "Deep Eutectic Solvents: Physiochemical Properties and Gas Seperation Applications" Energy & Fuels 29:2616-2644 (2015).
Guimaraes et al., "Site-Specific C-terminal and internal loop labeling of proteins using sortase-mediated reactions", Nature Protocols 8:1787-1799 (2013).
Hongyuan et al., "Sortase-Mediated Protein Ligation: A New Method for Protein Engineering" J. Am. Chem. Soc. 126-2670-2671 (2004).
Huang et al., "Deep eutectic solvents can be viable enzyme activators and stabilizers" Journal of Chem. Technol Biotechnol 89:1875-1981 (2014).
ISR for PCT/EP2016/072502 (dated Nov. 8, 2016).
Kyoui et al., "Genetic distance in the whole-genome perspective on Listeria monocytogenes strains F2-382 and NIHS-28 that show similar subtyping results" BMC Microbiology 14:309 (2014).
Lingberg et al., "Deep eutectic solvents (DESs) viable cosolvents for enzyme-catalyzed epoxide hyrolysis" Journal of Biotechnology 147:169-171 (2010).
Maugeri et al., "Chymotrypsin-Catalyzed Peptide Synthesis in Deep Eutectic Solvents" European Journal of Organic Chemistry: 4223-4228 (2013).

(56) References Cited

OTHER PUBLICATIONS

Nguyen et al., "Establishment of an experimental system allowing immobilization of proteins on the surface of Bacillus subtilis cells" Journal of Biotechnology 122:473-482 (2006).
Other Database, Database EBI accession No. UNIPROT:AOAOE1R5I2, (SubName: Full=Putative cysteine protease ywpE {ECO:0000313|EMBL:CCO63533.1}; EC=3.4.22.- {ECO:0000313|EMBL:CCO63533.1};) May 27, 2015.
Other Database, UNIPROT:A0A0B8RCN4,Database accession No. UNIPROT:A0A0B8RCN4 SubName: Full=Cysteine protease {ECO:0000313:EMBL:GAM94542.1}; SubName: Full=Sortase {ECO:00003131EMBL:AGR15336.1}; SubName: Full=Sortase A {ECO:0000313:EMBL:AKK25356.1} Sep. 16, 2015.
Other Database, UNIPROT:A9LY59, retrieved from EBI accession No. UNIPROT:A9LY59, SubName: Full=Sortase A {ECO:00003113:EMBL:ABX11549.1}; Flags: Fragment; Feb. 5, 2008.
Sutherland and Durand, Recent Results Cancer Res 95:24-49 (1984).
Tang et al., "Recent developments in deep eutectic solvents in chemical sciences" Monatsh Chem. 144:1427-1454 (2013).
Zhang et al., "Deep eutectic solvents: syntheses, properties and applications" Chem Soc Rev 41:7108-7146 (2012).
Zhao et al., "Choline-based deep eutectic solvents for enzymatic preparation of biodiesel from soybean oil" Journal of Molecular Catalysis B: Enzymatic 85-86:243-247 (2013).
Bierne et al., "Inactivation of the srtA gene in Listeria monocytogenes inhibits anchoring of surface proteins and affects virulence" Molecular Microbiology 43(4):869-881 (2002).
Bolken et al., "Inactivation of the srtA gene in *Streptococcus gordonii* inhibits cell wall anchoring of surface proteins and decreases in vitro and in vivo adhesion" Infection and Immunity 69(1):75-80 (2001).
Chan et al., "Covalent attachment of proteins to solid supports and surfaces via sortase-mediated ligation" PlosOne(11):e1164 (2007).
Dawson et al., "Synthesis of Native Proteins by Chemical Ligation" Annu. Rev. Biochem 69:923-60 (2000).
Dhar et al., "Anchor Structure of cell wall surface proteins in listeria monocytogenes" Biochemistry 39(13):3725-3733 (2000).
Fischetti et al., "Conservation of a hexapeptide sequence in the anchor region of surface proteins from Gram-positive cocci" Molecular Microbiology 4(9):1603-1605 (1990).
Glaser et al., "Comparative genomics of listeria species" Science 294:849-852 (2001).
Ilangovan et al., "Structure of sortase, the transpeptidase that anchors proteins to the cell wall of *Staphylococcus aureus*" Proceedings of the National Academy of Sciences 98(11):6056-6061 (2001).
Jiang et al., "Research Progress on Sortase and its Application in Biotechnology" Current Biotechnology 1(3):184-188 (2011).
Kruger et al., "Analysis of the substrate specificity of the *Staphylococcus aureus* sortase transpeptidase SrtA" Biochemistry 43(6):1541-1551 (2004).
Mao et al., "Sortase-Mediated protein ligation: A new method for protein engineering" Journal of American Chemical Society 126:2670-2671 (2004).
Mazmanian et al., "Sortase-catalysed anchoring of surface proteins to the cell wall of *Staphylococcus aureus*" Molecular Microbiology 40(5):1049-1057 (2001).
Mazmanian et al., "*Staphylococcus aureus* Sortase, an enzyme that anchors surface proteins to the cell wall" Science 285:760-763 (1999).
Pallen et al., "An Embarrassment of sortases—a richness of substrates?" Trends in Microbiology 9(3):97-101 (2001).
Parthasarathy et al., Bioconjugate Chem 18:469-476 (2007).
Samantaray et al., "Peptide-sugar ligation catalyzed by transpeptidase sortase: A facile approach to neoglycoconjugate synthesis" Journal Am. Chem. Soc. 130:2132-2133 (2008).
Yan et al., "Synthesis of Peptides and Proteins without Cysteine Residues by Native Chemical Ligation Combined with Desulfurization" Journal Am. Chem. Soc. 123:526-533 (2001).
Swee et al., "Sortase-mediated modification of αDEC205 affords optimization of antigen presentation and immunization against a set of viral epitopes" PNAS 110(4):1428-1433 (2013).
Tanaka et al., "Site-Specific Protein Modification on Living Cells Catalyzed by Sortase" ChemBioChem 9:802-807 (2008).
Witte et al., "Preparation of unnatural N-to-N and C-to-C protein fusions" PNAS 109(30):11993-11998 (2012).

* cited by examiner

SEQUENCE LISTING

```
<160> NUMBER OF SEQ ID NOS: 182

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      LPXTG sortase-motif
<220> FEATURE:
<221> NAME/KEY: MOD_RES
<222> LOCATION: (3)..(3)
<223> OTHER INFORMATION: Any amino acid

<400> SEQUENCE: 1

Leu Pro Xaa Thr Gly
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      cystein sortase motif 1

<400> SEQUENCE: 2

Cys Gly Gly Gly
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      cystein sortase motif 2

<400> SEQUENCE: 3

Cys Ala Ala Ala
1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      sortase motif

<400> SEQUENCE: 4

Leu Pro Glu Thr Gly
1               5

<210> SEQ ID NO 5
<211> LENGTH: 147
<212> TYPE: PRT
<213> ORGANISM: Artificial Sequence
```

```
<220> FEATURE:
<223> OTHER INFORMATION: Description of Artificial Sequence: Synthetic
      Staphylococcus aureus Sortase A shortened version N(1-59)

<400> SEQUENCE: 5

Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
                20                  25                  30

Ala Thr Pro Glu Gln Leu Asn Arg Gly Val Ser Phe Ala Glu Glu Asn
            35                  40                  45

Glu Ser Leu Asp Asp Gln Asn Ile Ser Ile Ala Gly His Thr Phe Ile
50                  55                  60

Asp Arg Pro Asn Tyr Gln Phe Thr Asn Leu Lys Ala Ala Lys Lys Gly
65                  70                  75                  80

Ser Met Val Tyr Phe Lys Val Gly Asn Glu Thr Arg Lys Tyr Lys Met
                85                  90                  95

Thr Ser Ile Arg Asp Val Lys Pro Thr Asp Val Gly Val Leu Asp Glu
            100                 105                 110

Gln Lys Gly Lys Asp Lys Gln Leu Thr Leu Ile Thr Cys Asp Asp Tyr
        115                 120                 125

Asn Glu Lys Thr Gly Val Trp Glu Lys Arg Lys Ile Phe Val Ala Thr
130                 135                 140

Glu Val Lys
145

<210> SEQ ID NO 6
<211> LENGTH: 168
<212> TYPE: PRT
<213> ORGANISM: Artificial Sequence
<220> FEATURE:
<223> OTHER INFORMATION: Description of Artificial Sequence: Synthetic
      Streptococcus pyogenes Sortase A shortened version

<400> SEQUENCE: 6

Val Leu Gln Ala Gln Met Ala Ala Gln Gln Leu Pro Val Ile Gly Gly
1               5                   10                  15

Ile Ala Ile Pro Glu Leu Gly Ile Asn Leu Pro Ile Phe Lys Gly Leu
                20                  25                  30

Gly Asn Thr Glu Leu Ile Tyr Gly Ala Gly Thr Met Lys Glu Glu Gln
            35                  40                  45

Val Met Gly Gly Glu Asn Asn Tyr Ser Leu Ala Ser His His Ile Phe
50                  55                  60

Gly Ile Thr Gly Ser Ser Gln Met Leu Phe Ser Pro Leu Glu Arg Ala
65                  70                  75                  80

Gln Asn Gly Met Ser Ile Tyr Leu Thr Asp Lys Glu Lys Ile Tyr Glu
                85                  90                  95

Tyr Ile Ile Lys Asp Val Phe Thr Val Ala Pro Glu Arg Val Asp Val
            100                 105                 110

Ile Asp Asp Thr Ala Gly Leu Lys Glu Val Thr Leu Val Thr Cys Thr
        115                 120                 125

Asp Ile Glu Ala Thr Glu Arg Ile Ile Val Lys Gly Glu Leu Lys Thr
130                 135                 140

Glu Tyr Asp Phe Asp Lys Ala Pro Ala Asp Val Leu Lys Ala Phe Asn
145                 150                 155                 160

His Ser Tyr Asn Gln Val Ser Thr
                165
```

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      Arg-tag

<400> SEQUENCE: 7

Arg Arg Arg Arg Arg
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      Arg-tag 2

<400> SEQUENCE: 8

Arg Arg Arg Arg Arg Arg
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      His-tag

<400> SEQUENCE: 9

His His His His His His
1               5

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 10

Lys Asp His Leu Ile His Asn Val His Lys Glu Phe His Ala His Ala
1               5                   10                  15

His Asn Lys

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 11

Asp Tyr Lys Asp Asp Asp Asp Lys
1               5

<210> SEQ ID NO 12
<211> LENGTH: 22
<212> TYPE: PRT
<213> ORGANISM: Artificial Sequence
<220> FEATURE:

```
<223> OTHER INFORMATION: Description of Artificial Sequence: Synthetic
      amino acid tag

<400> SEQUENCE: 12

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      amino acid tag#

<400> SEQUENCE: 13

Ala Trp Arg His Pro Gln Phe Gly Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 14

Trp Ser His Pro Gln Phe Glu Lys
1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 15

Met Asp Val Glu Ala Trp Leu Gly Ala Arg
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 16

Met Asp Val Glu Ala Trp Leu Gly Ala Arg Val Pro Leu Val Glu Thr
1               5                   10                  15

<210> SEQ ID NO 17
<211> LENGTH: 38
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 17

Met Asp Glu Lys Thr Thr Gly Trp Arg Gly Gly His Val Val Glu Gly
```

-continued

```
1               5                   10                  15
Leu Ala Gly Glu Leu Glu Gln Leu Arg Ala Arg Leu Glu His His Pro
            20                  25                  30

Gln Gly Gln Arg Glu Pro
                35
```

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 18

```
Glu Gln Lys Leu Ile Ser Glu Glu Asp Leu
1               5                   10
```

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 19

```
Lys Glu Thr Ala Ala Ala Lys Phe Glu Arg Gln His Met Asp Ser
1               5                   10                  15
```

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 20

```
Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25
```

<210> SEQ ID NO 21
<211> LENGTH: 47
<212> TYPE: PRT
<213> ORGANISM: Artificial Sequence
<220> FEATURE:
<223> OTHER INFORMATION: Description of Artificial Sequence: Synthetic
      amino acid tag

<400> SEQUENCE: 21

```
Pro Ala Thr Thr Thr Gly Ser Ser Pro Gly Pro Thr Gln Ser His Tyr
1               5                   10                  15

Gly Gln Cys Gly Gly Ile Gly Tyr Ser Gly Pro Thr Val Cys Ala Ser
            20                  25                  30

Gly Thr Thr Cys Gln Val Leu Asn Pro Tyr Tyr Ser Gln Cys Leu
        35                  40                  45
```

<210> SEQ ID NO 22
<211> LENGTH: 32
<212> TYPE: PRT
<213> ORGANISM: Butyrivibrio fibrisolvens

```
<400> SEQUENCE: 22

Met Asp Trp Asn Ala Asn Ile Ala Pro Gly Asn Ser Val Glu Phe Gly
1               5                   10                  15

Ile Gln Gly Ala Gly Ser Val Gly Asn Val Ile Asp Ile Thr Val Glu
                20                  25                  30

<210> SEQ ID NO 23
<211> LENGTH: 51
<212> TYPE: PRT
<213> ORGANISM: Artificial Sequence
<220> FEATURE:
<223> OTHER INFORMATION: Description of Artificial Sequence: Synthetic
      chitin-binding-domain

<400> SEQUENCE: 23

Thr Asn Pro Gly Val Ser Ala Trp Gln Val Asn Thr Ala Tyr Thr Ala
1               5                   10                  15

Gly Gln Leu Val Thr Tyr Asn Gly Lys Thr Tyr Lys Cys Leu Gln Pro
                20                  25                  30

His Thr Ser Leu Ala Gly Trp Glu Pro Ser Asn Val Pro Ala Leu Trp
            35                  40                  45

Gln Leu Gln
    50

<210> SEQ ID NO 24
<211> LENGTH: 209
<212> TYPE: PRT
<213> ORGANISM: Chondrus crispus

<400> SEQUENCE: 24

Met Pro Glu Ile Lys Leu Thr Tyr Phe Asp Met Arg Gly Arg Ala Glu
1               5                   10                  15

Ala Ser Arg Leu Ala Leu Val Val Gly Glu Ile Pro Phe Glu Asp Glu
                20                  25                  30

Arg Val Val Phe Asp His Trp Lys Glu Ala Lys Pro Lys Thr Pro Tyr
            35                  40                  45

Ala Ala Leu Pro Met Leu Thr Val Asp Gly Met Gln Val Ala Gln Ser
50                  55                  60

Asp Ala Ile Leu Arg Tyr Cys Gly Lys Leu Ala Gly Leu Tyr Pro Ser
65                  70                  75                  80

Asp Pro Leu Glu Ala Ala Lys Val Asp Glu Val Gly Val Ile Asp
                85                  90                  95

Asp Val Thr His Ala Met Tyr Arg Tyr Arg Gly Asp Asp Lys Asp Lys
                100                 105                 110

Leu Arg Glu Glu Arg Asp Lys Phe Ser Lys Val Asp Val Pro Arg Tyr
            115                 120                 125

Val Gly Ala Leu Glu Lys Arg Leu Glu Ala Phe Gly Asp Gly Pro Trp
    130                 135                 140

Ala Val Gly Gly Asn Met Thr Ile Ala Asp Leu His Ile Cys His Leu
145                 150                 155                 160

Val Thr Asn Ile Arg Cys Gly Met Leu Asp Phe Val Asp Lys Asp Leu
                165                 170                 175

Leu Glu Gly Tyr Val Arg Ile Val Lys Ser Tyr Ser Ala Val Met Glu
            180                 185                 190

His Pro Lys Val Thr Glu Trp Tyr Glu Lys Lys Pro Val Lys Met Phe
        195                 200                 205

Ser
```

<210> SEQ ID NO 25
<211> LENGTH: 396
<212> TYPE: PRT
<213> ORGANISM: Escherichia coli

<400> SEQUENCE: 25

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp

```
            370                 375                 380
Glu Ala Leu Lys Asp Ala Gln Thr Arg Ile Thr Lys
385                 390                 395

<210> SEQ ID NO 26
<211> LENGTH: 206
<212> TYPE: PRT
<213> ORGANISM: Staphylococcus aureus

<400> SEQUENCE: 26

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
    130                 135                 140

Lys Val Gly Asn Glu Thr Arg Lys Tyr Lys Met Thr Ser Ile Arg Asp
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
        195                 200                 205

<210> SEQ ID NO 27
<211> LENGTH: 222
<212> TYPE: PRT
<213> ORGANISM: Listeria monocytogenes

<400> SEQUENCE: 27

Met Leu Lys Lys Thr Ile Ala Ala Ala Leu Ala Ala Gly Leu Leu
1               5                   10                  15

Leu Ile Phe Ser Pro Phe Ile Lys Asn Gly Ile Val Lys Tyr Met Ser
            20                  25                  30

Gly His Glu Thr Ile Glu Gln Tyr Lys Ala Ser Asp Ile Lys Lys Asn
        35                  40                  45

Asn Glu Lys Asp Ala Thr Phe Asp Phe Glu Ser Val Gln Leu Pro Ser
    50                  55                  60

Met Thr Ser Val Ile Lys Gly Ala Ala Asn Tyr Asp Lys Asp Ala Val
65                  70                  75                  80

Val Gly Ser Ile Ala Val Pro Ser Val Asp Val Asn Leu Leu Val Phe
                85                  90                  95

Lys Gly Thr Asn Thr Ala Asn Leu Leu Ala Gly Ala Thr Thr Met Arg
```

```
              100                 105                 110
Ser Asp Gln Val Met Gly Lys Gly Asn Tyr Pro Leu Ala Gly His His
            115                 120                 125

Met Arg Asp Glu Ser Met Leu Phe Gly Pro Ile Met Lys Val Lys Lys
        130                 135                 140

Gly Asp Lys Ile Tyr Leu Thr Asp Leu Glu Asn Leu Tyr Glu Tyr Thr
145                 150                 155                 160

Val Thr Glu Thr Lys Thr Ile Asp Glu Thr Glu Val Ser Val Ile Asp
                165                 170                 175

Asn Thr Lys Asp Ala Arg Ile Thr Leu Ile Thr Cys Asp Lys Pro Thr
            180                 185                 190

Glu Thr Thr Lys Arg Phe Val Ala Val Gly Glu Leu Glu Lys Thr Glu
        195                 200                 205

Lys Leu Thr Lys Glu Leu Glu Asn Lys Tyr Phe Pro Ser Lys
210                 215                 220

<210> SEQ ID NO 28
<211> LENGTH: 2
<212> TYPE: PRT
<213> ORGANISM: Artificial Sequence
<220> FEATURE:
<223> OTHER INFORMATION: Description of Artificial Sequence: Synthetic
      oligogylcine

<400> SEQUENCE: 28

Gly Gly
1

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      oligoglycine

<400> SEQUENCE: 29

Gly Gly Gly
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      oligoglycine

<400> SEQUENCE: 30

Gly Gly Gly Gly
1

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      oligoglycine

<400> SEQUENCE: 31

Gly Gly Gly Gly Gly
1               5
```

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      hexa-histidine tag with linker

<400> SEQUENCE: 32

Met Arg Gly Ser His His His His His His Gly Ser
1               5                   10

<210> SEQ ID NO 33
<211> LENGTH: 249
<212> TYPE: PRT
<213> ORGANISM: Streptococcus pyogenes

<400> SEQUENCE: 33

Met Val Lys Lys Gln Lys Arg Lys Ile Lys Ser Met Ser Trp Ala
1               5                   10                  15

Arg Lys Leu Leu Ile Ala Val Leu Leu Ile Leu Gly Leu Ala Leu Leu
                20                  25                  30

Phe Asn Lys Pro Ile Arg Asn Thr Leu Ile Ala Arg Asn Ser Asn Lys
                35                  40                  45

Tyr Gln Val Thr Lys Val Ser Lys Lys Gln Ile Lys Lys Asn Lys Glu
    50                  55                  60

Ala Lys Ser Thr Phe Asp Phe Gln Ala Val Glu Pro Val Ser Thr Glu
65              70                  75                  80

Ser Val Leu Gln Ala Gln Met Ala Ala Gln Gln Leu Pro Val Ile Gly
                85                  90                  95

Gly Ile Ala Ile Pro Glu Leu Gly Ile Asn Leu Pro Ile Phe Lys Gly
                100                 105                 110

Leu Gly Asn Thr Glu Leu Ile Tyr Gly Ala Gly Thr Met Lys Glu Glu
                115                 120                 125

Gln Val Met Gly Gly Glu Asn Asn Tyr Ser Leu Ala Ser His His Ile
            130                 135                 140

Phe Gly Ile Thr Gly Ser Ser Gln Met Leu Phe Ser Pro Leu Glu Arg
145             150                 155                 160

Ala Gln Asn Gly Met Ser Ile Tyr Leu Thr Asp Lys Glu Lys Ile Tyr
                165                 170                 175

Glu Tyr Ile Ile Lys Asp Val Phe Thr Val Ala Pro Glu Arg Val Asp
                180                 185                 190

Val Ile Asp Asp Thr Ala Gly Leu Lys Glu Val Thr Leu Val Thr Cys
                195                 200                 205

Thr Asp Ile Glu Ala Thr Glu Arg Ile Ile Val Lys Gly Glu Leu Lys
                210                 215                 220

Thr Glu Tyr Asp Phe Asp Lys Ala Pro Ala Asp Val Leu Lys Ala Phe
225                 230                 235                 240

Asn His Ser Tyr Asn Gln Val Ser Thr
                245

<210> SEQ ID NO 34
<211> LENGTH: 178
<212> TYPE: PRT
<213> ORGANISM: Artificial Sequence
<220> FEATURE:
<223> OTHER INFORMATION: Description of Artificial Sequence: Synthetic
      Staphylococcus aureus Sortase A shortened version N(2-29)

-continued

<400> SEQUENCE: 34

Met Asp Asn Tyr Leu His Asp Lys Asp Lys Asp Glu Lys Ile Glu Gln
1               5                   10                  15

Tyr Asp Lys Asn Val Lys Glu Gln Ala Ser Lys Asp Lys Lys Gln Gln
            20                  25                  30

Ala Lys Pro Gln Ile Pro Lys Asp Ser Lys Val Ala Gly Tyr Ile
        35                  40                  45

Glu Ile Pro Asp Ala Asp Ile Lys Glu Pro Val Tyr Pro Gly Pro Ala
50                  55                  60

Thr Pro Glu Gln Leu Asn Arg Gly Val Ser Phe Ala Glu Glu Asn Glu
65                  70                  75                  80

Ser Leu Asp Asp Gln Asn Ile Ser Ile Ala Gly His Thr Phe Ile Asp
                85                  90                  95

Arg Pro Asn Tyr Gln Phe Thr Asn Leu Lys Ala Ala Lys Lys Gly Ser
            100                 105                 110

Met Val Tyr Phe Lys Val Gly Asn Glu Thr Arg Lys Tyr Lys Met Thr
        115                 120                 125

Ser Ile Arg Asp Val Lys Pro Thr Asp Val Gly Val Leu Asp Glu Gln
130                 135                 140

Lys Gly Lys Asp Lys Gln Leu Thr Leu Ile Thr Cys Asp Asp Tyr Asn
145                 150                 155                 160

Glu Lys Thr Gly Val Trp Glu Lys Arg Lys Ile Phe Val Ala Thr Glu
                165                 170                 175

Val Lys

<210> SEQ ID NO 35
<211> LENGTH: 222
<212> TYPE: PRT
<213> ORGANISM: Listeria monocytogenes

<400> SEQUENCE: 35

Met Leu Lys Lys Thr Ile Ala Ala Ala Leu Ala Ala Gly Leu Leu
1               5                   10                  15

Leu Ile Phe Ser Pro Phe Ile Lys Asn Gly Ile Val Lys Tyr Met Ser
            20                  25                  30

Gly His Glu Thr Ile Glu Gln Tyr Lys Ala Ser Asp Ile Lys Lys Asn
        35                  40                  45

Asn Glu Lys Asp Ala Thr Phe Asp Phe Glu Ser Val Gln Leu Pro Ser
    50                  55                  60

Met Thr Ser Val Ile Lys Gly Ala Ala Asn Tyr Asp Lys Asp Ala Val
65                  70                  75                  80

Val Gly Ser Ile Ala Val Pro Ser Val Asp Val Asn Leu Leu Val Phe
                85                  90                  95

Lys Gly Thr Asn Thr Ala Asn Leu Leu Ala Gly Ala Thr Thr Met Arg
            100                 105                 110

Ser Asp Gln Val Met Gly Lys Gly Asn Tyr Pro Leu Ala Gly His His
        115                 120                 125

Met Arg Asp Glu Ser Met Leu Phe Gly Pro Ile Met Lys Val Lys Lys
130                 135                 140

Gly Asp Lys Ile Tyr Leu Thr Asp Leu Glu Asn Leu Tyr Glu Tyr Thr
145                 150                 155                 160

Val Thr Glu Thr Lys Thr Ile Asp Glu Thr Glu Val Ser Val Ile Asp
                165                 170                 175

Asp Thr Lys Asp Ala Arg Ile Thr Leu Ile Thr Cys Asp Lys Pro Thr

```
                180             185                 190
Glu Thr Thr Lys Arg Phe Val Ala Val Gly Glu Leu Glu Lys Thr Glu
            195                 200                 205

Lys Leu Thr Lys Glu Leu Glu Asn Lys Tyr Phe Pro Ser Lys
            210                 215                 220

<210> SEQ ID NO 36
<211> LENGTH: 173
<212> TYPE: PRT
<213> ORGANISM: Artificial Sequence
<220> FEATURE:
<223> OTHER INFORMATION: Description of Artificial Sequence: Synthetic
      Listeria monocytogenes Sortase A shortened variant A

<400> SEQUENCE: 36

Glu Lys Asp Ala Thr Phe Asp Phe Glu Ser Val Gln Leu Pro Ser Met
1               5                   10                  15

Thr Ser Val Ile Lys Gly Ala Ala Asn Tyr Asp Lys Asp Ala Val Val
            20                  25                  30

Gly Ser Ile Ala Val Pro Ser Val Asp Val Asn Leu Leu Val Phe Lys
        35                  40                  45

Gly Thr Asn Thr Ala Asn Leu Leu Ala Gly Ala Thr Thr Met Arg Ser
    50                  55                  60

Asp Gln Val Met Gly Lys Gly Asn Tyr Pro Leu Ala Gly His His Met
65                  70                  75                  80

Arg Asp Glu Ser Met Leu Phe Gly Pro Ile Met Lys Val Lys Lys Gly
                85                  90                  95

Asp Lys Ile Tyr Leu Thr Asp Leu Glu Asn Leu Tyr Glu Tyr Thr Val
            100                 105                 110

Thr Glu Thr Lys Thr Ile Asp Glu Thr Glu Val Ser Val Ile Asp Asp
        115                 120                 125

Thr Lys Asp Ala Arg Ile Thr Leu Ile Thr Cys Asp Lys Pro Thr Glu
    130                 135                 140

Thr Thr Lys Arg Phe Val Ala Val Gly Glu Leu Glu Lys Thr Glu Lys
145                 150                 155                 160

Leu Thr Lys Glu Leu Glu Asn Lys Tyr Phe Pro Ser Lys
                165                 170

<210> SEQ ID NO 37
<211> LENGTH: 156
<212> TYPE: PRT
<213> ORGANISM: Artificial Sequence
<220> FEATURE:
<223> OTHER INFORMATION: Description of Artificial Sequence: Synthetic
      Listeria monocytogenes Sortase A shortened variant B

<400> SEQUENCE: 37

Ser Val Ile Lys Gly Ala Ala Asn Tyr Asp Lys Asp Ala Val Val Gly
1               5                   10                  15

Ser Ile Ala Val Pro Ser Val Asp Val Asn Leu Leu Val Phe Lys Gly
            20                  25                  30

Thr Asn Thr Ala Asn Leu Leu Ala Gly Ala Thr Thr Met Arg Ser Asp
        35                  40                  45

Gln Val Met Gly Lys Gly Asn Tyr Pro Leu Ala Gly His His Met Arg
    50                  55                  60

Asp Glu Ser Met Leu Phe Gly Pro Ile Met Lys Val Lys Lys Gly Asp
65                  70                  75                  80

Lys Ile Tyr Leu Thr Asp Leu Glu Asn Leu Tyr Glu Tyr Thr Val Thr
```

```
                85                  90                  95
Glu Thr Lys Thr Ile Asp Glu Thr Glu Val Ser Val Ile Asp Asp Thr
            100                 105                 110

Lys Asp Ala Arg Ile Thr Leu Ile Thr Cys Asp Lys Pro Thr Glu Thr
        115                 120                 125

Thr Lys Arg Phe Val Ala Val Gly Glu Leu Glu Lys Thr Glu Lys Leu
    130                 135                 140

Thr Lys Glu Leu Glu Asn Lys Tyr Phe Pro Ser Lys
145                 150                 155

<210> SEQ ID NO 38
<211> LENGTH: 150
<212> TYPE: PRT
<213> ORGANISM: Artificial Sequence
<220> FEATURE:
<223> OTHER INFORMATION: Description of Artificial Sequence: Synthetic
      Listeria monocytogenes Sortase A shortened variant C

<400> SEQUENCE: 38

Ala Asn Tyr Asp Lys Asp Ala Val Val Gly Ser Ile Ala Val Pro Ser
1               5                   10                  15

Val Asp Val Asn Leu Leu Val Phe Lys Gly Thr Asn Thr Ala Asn Leu
            20                  25                  30

Leu Ala Gly Ala Thr Thr Met Arg Ser Asp Gln Val Met Gly Lys Gly
        35                  40                  45

Asn Tyr Pro Leu Ala Gly His His Met Arg Asp Glu Ser Met Leu Phe
    50                  55                  60

Gly Pro Ile Met Lys Val Lys Lys Gly Asp Lys Ile Tyr Leu Thr Asp
65                  70                  75                  80

Leu Glu Asn Leu Tyr Glu Tyr Thr Val Thr Glu Thr Lys Thr Ile Asp
                85                  90                  95

Glu Thr Glu Val Ser Val Ile Asp Asp Thr Lys Asp Ala Arg Ile Thr
            100                 105                 110

Leu Ile Thr Cys Asp Lys Pro Thr Glu Thr Thr Lys Arg Phe Val Ala
        115                 120                 125

Val Gly Glu Leu Glu Lys Thr Glu Lys Leu Thr Lys Glu Leu Glu Asn
    130                 135                 140

Lys Tyr Phe Pro Ser Lys
145                 150

<210> SEQ ID NO 39
<211> LENGTH: 137
<212> TYPE: PRT
<213> ORGANISM: Artificial Sequence
<220> FEATURE:
<223> OTHER INFORMATION: Description of Artificial Sequence: Synthetic
      Listeria monocytogenes Sortase A shortened variant D

<400> SEQUENCE: 39

Ala Asn Tyr Asp Lys Asp Ala Val Val Gly Ser Ile Ala Val Pro Ser
1               5                   10                  15

Val Asp Val Asn Leu Leu Val Phe Lys Gly Thr Asn Thr Ala Asn Leu
            20                  25                  30

Leu Ala Gly Ala Thr Thr Met Arg Ser Asp Gln Val Met Gly Lys Gly
        35                  40                  45

Asn Tyr Pro Leu Ala Gly His His Met Arg Asp Glu Ser Met Leu Phe
    50                  55                  60

Gly Pro Ile Met Lys Val Lys Lys Gly Asp Lys Ile Tyr Leu Thr Asp
```

```
                65                  70                  75                  80

Leu Glu Asn Leu Tyr Glu Tyr Thr Val Thr Glu Thr Lys Thr Ile Asp
                85                  90                  95

Glu Thr Glu Val Ser Val Ile Asp Asp Thr Lys Asp Ala Arg Ile Thr
            100                 105                 110

Leu Ile Thr Cys Asp Lys Pro Thr Glu Thr Lys Arg Phe Val Ala
        115                 120                 125

Val Gly Glu Leu Glu Lys Thr Glu Lys
    130                 135

<210> SEQ ID NO 40
<211> LENGTH: 141
<212> TYPE: PRT
<213> ORGANISM: Artificial Sequence
<220> FEATURE:
<223> OTHER INFORMATION: Description of Artificial Sequence: Synthetic
      Listeria monocytogenes Sortase A shortened variant E

<400> SEQUENCE: 40

Gly Ser Ile Ala Val Pro Ser Val Asp Val Asn Leu Leu Val Phe Lys
1               5                   10                  15

Gly Thr Asn Thr Ala Asn Leu Leu Ala Gly Ala Thr Thr Met Arg Ser
            20                  25                  30

Asp Gln Val Met Gly Lys Gly Asn Tyr Pro Leu Ala Gly His His Met
        35                  40                  45

Arg Asp Glu Ser Met Leu Phe Gly Pro Ile Met Lys Val Lys Lys Gly
    50                  55                  60

Asp Lys Ile Tyr Leu Thr Asp Leu Glu Asn Leu Tyr Glu Tyr Thr Val
65                  70                  75                  80

Thr Glu Thr Lys Thr Ile Asp Glu Thr Glu Val Ser Val Ile Asp Asp
                85                  90                  95

Thr Lys Asp Ala Arg Ile Thr Leu Ile Thr Cys Asp Lys Pro Thr Glu
            100                 105                 110

Thr Thr Lys Arg Phe Val Ala Val Gly Glu Leu Glu Lys Thr Glu Lys
        115                 120                 125

Leu Thr Lys Glu Leu Glu Asn Lys Tyr Phe Pro Ser Lys
    130                 135                 140

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      LPXTA sortase-motif
<220> FEATURE:
<221> NAME/KEY: MOD_RES
<222> LOCATION: (3)..(3)
<223> OTHER INFORMATION: Any amino acid

<400> SEQUENCE: 41

Leu Pro Xaa Thr Ala
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      sortase-motif
```

```
<400> SEQUENCE: 42

Leu Pro Glu Thr Ala
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      sortase-motif

<400> SEQUENCE: 43

Leu Pro Lys Thr Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      sortase-motif

<400> SEQUENCE: 44

Leu Pro Lys Thr Ala
1               5

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala conjugated to LCR640-U

<400> SEQUENCE: 45

Ala Leu Pro Glu Thr Gly Gly Gly Arg Arg Cys
1               5                   10

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Gly Trp Trp
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Pro Thr Thr Gly
1               5
```

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ala Leu Pro Glu Thr Gly Glu Glu
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Pro Asp Thr Gly
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Pro Asn Thr Gly
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Pro Leu Ala Ala Gly
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Pro Lys Ala Gly
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 53

Leu Pro Gln Thr Gly
1               5

<210> SEQ ID NO 54
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Val Ala Gly His Val Asp Asn Ala Glu Gly Pro Ala Val Phe Tyr Arg
1               5                   10                  15

Leu Gly Ala Leu Glu Lys Gly Ser Ala Ile Glu Ile Asp Arg Arg Asp
            20                  25                  30

Gly Gly Val Ala Val Phe Thr Val Asp Ala Val Glu Val Tyr Ala Ala
        35                  40                  45

Asp Ala Phe Pro Asp Glu Lys Val Tyr Gly Ala Ala Asp Arg Pro Glu
    50                  55                  60

Leu Arg Val Ile Thr Cys Gly Pro Tyr Ser Arg Ser Thr Gly Tyr
65                  70                  75                  80

Gln Gly Asn Val Val
                85

<210> SEQ ID NO 55
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Val Val Gly His Val Asp Asn Gln Gln Gly Pro Ala Val Phe Tyr Gly
1               5                   10                  15

Leu Gly Ala Leu Lys Lys Gly Asn Lys Val Glu Val His Arg Gln Asp
            20                  25                  30

Gly Lys Thr Ala Val Phe Glu Ile Tyr Gly Ile Glu Val Phe Glu Lys
        35                  40                  45

Asn Asn Phe Pro Gly Asp Arg Val Tyr Gly Ser Lys Gly Ser Pro Glu
    50                  55                  60

Leu Arg Val Ile Thr Cys Gly Gly Phe Thr Lys Gln Asn Gly Tyr
65                  70                  75                  80

Asp Gly Asn Val Val
                85

<210> SEQ ID NO 56
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ile Ala Gly His Val Asp Thr Lys Thr Ser Ala Ala Val Phe Ala Arg
1               5                   10                  15

Leu Asp Gln Leu Asp Lys Gly Asp Lys Phe Gln Val Arg Arg Ala Asp
            20                  25                  30
```

Gly Arg Ser Ala Thr Phe Val Val Asp Gly Leu Glu Thr Phe Ala Lys
            35                  40                  45

Asp Glu Phe Pro Ser Asp Arg Val Tyr Gly Asp Ala Asp Arg Pro Glu
        50                  55                  60

Val Arg Leu Ile Thr Cys Ala Gly Asp Tyr Asp His Lys Val Lys Asp
65                  70                  75                  80

Tyr Thr Asp Asn Leu Val
                85

<210> SEQ ID NO 57
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Val Gly His Val Asp Thr Glu Thr Arg Pro Ala Val Phe Tyr Gln
1               5                   10                  15

Leu Ser Thr Leu Glu Pro Gly Gln Thr Ile Arg Val Ala Arg Asp Asp
            20                  25                  30

Asp Glu Val Ala Glu Phe Thr Val Asp Asp Val Gln Val Leu Thr Arg
        35                  40                  45

Asp Gly Phe Asp Ala Gln Gln Ala Tyr Gly Pro Arg Asp Thr Gly Arg
    50                  55                  60

Ser Glu Leu Arg Leu Ile Thr Cys Gly Gly Thr Phe Asp Gln Thr Thr
65                  70                  75                  80

Asp Ser Tyr Thr Ala Asn Val Val
                85

<210> SEQ ID NO 58
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Leu Ser Gly His Arg Asp Thr Val Phe Arg Asp Met Gly Lys Leu Glu
1               5                   10                  15

Ile Gly Asp Asp Leu Thr Val His Met Pro Tyr Gly Ser Tyr Thr Tyr
            20                  25                  30

Arg Ile Val Asp Thr Glu Ile Val Asp Ala Asn Asp Thr Ser Val Ile
        35                  40                  45

Arg Ser Thr Ala Pro Asp Glu Val Leu Thr Leu Ser Thr Cys Tyr Pro
    50                  55                  60

Phe Asn Phe Ile Gly Ser Ala Pro Glu Arg Tyr Ile Ile Tyr
65                  70                  75

<210> SEQ ID NO 59
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Leu Ser Gly His Arg Asp Thr Val Phe Arg Thr Gly Glu Leu Glu
1               5                   10                  15

Lys Gly Asp Gln Leu Arg Leu Leu Ser Tyr Gly Glu Phe Thr Tyr
            20                  25                  30

Glu Ile Val Lys Thr Lys Ile Val Asp Lys Asp Thr Ser Ile Ile
            35                  40                  45

Thr Leu Gln His Glu Lys Glu Leu Ile Leu Thr Thr Cys Tyr Pro
            50                  55                  60

Phe Ser Tyr Val Gly Asn Ala Pro Lys Arg Tyr Ile Ile Tyr
65                  70                  75
```

<210> SEQ ID NO 60
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Leu Ser Gly His Arg Asp Thr Val Phe Arg Glu Leu Gly Glu Val Gly
1               5                   10                  15

Val Gly Asp Leu Leu Ile Val Glu Thr Ala Thr Gly Thr His Thr Tyr
            20                  25                  30

Arg Val Arg Lys Val Arg Ile Val Asp Glu Asp Arg Thr Val Ile
            35                  40                  45

Val Pro Lys Pro Arg Ala Thr Leu Thr Val Ser Thr Cys Tyr Pro Phe
            50                  55                  60

Asp Phe Ile Gly Ser Ala Pro Glu Arg Tyr Ile Leu Glu
65                  70                  75
```

<210> SEQ ID NO 61
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

```
Leu Ser Gly His Arg Asp Thr Val Phe Thr Asp Leu Gly Gln Leu Lys
1               5                   10                  15

Glu Lys Asp Thr Leu Val Leu Glu Tyr Asp Asn Lys Thr Tyr Thr Tyr
            20                  25                  30

Glu Ile Gln Lys Ile Trp Ile Thr His Ala Asp Asp Arg Thr Val Ile
            35                  40                  45

Ile Lys Lys Glu Glu Pro Ile Leu Thr Leu Thr Thr Cys Tyr Pro Phe
            50                  55                  60

Asp Tyr Ile Gly Asp Ala Pro Asp Arg Tyr Ile Ile Glu
65                  70                  75
```

<210> SEQ ID NO 62
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ile Ala Ala His Arg Ser Arg Thr Tyr Gly Arg Gln Phe Asn Arg Leu

```
                1               5                   10                  15
Asp Glu Val Glu Val Gly Asp Val Ile Thr Val Thr Thr Asn Asn His
                20                  25                  30
Met Tyr Arg Tyr Thr Val Tyr Ser Ile Thr Val Glu Pro Thr Asn
                35                  40                  45
Ile Asp Ile Leu Gln His Asp Gly Thr Ala Pro Val Leu Thr Leu Ile
 50                  55                  60
Thr Cys Asp Pro Val Lys Asp Pro Thr His Arg Leu Ile Val Gln Ala
 65                  70                  75                  80
Glu Met
```

<210> SEQ ID NO 63
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Leu Ala Gly His Arg Ser Tyr Thr Phe Gly Glu Tyr Phe Asn Arg Leu
 1               5                   10                  15
Gly Glu Ile Gly Ser Gly Asp Glu Ile Asp Val Glu Thr Val Asn Gly
                20                  25                  30
Thr Phe Lys Tyr Lys Val Tyr Ser Thr Lys Val Val Leu Pro Ser Glu
                35                  40                  45
Val His Val Leu Asp Gln Thr Lys Asp Pro Thr Met Thr Leu Val Thr
 50                  55                  60
Cys Thr Pro Ile Arg Ile Ala Thr His Arg Leu Ile Ile Lys Ala Lys
 65                  70                  75                  80
Arg
```

<210> SEQ ID NO 64
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Leu Ala Gly His Arg Asn Thr His Gly Glu Pro Phe Arg Tyr Ile Asn
 1               5                   10                  15
Lys Leu Glu Pro Gly Asp Pro Ile Val Val Glu Thr Gln Asp Lys Tyr
                20                  25                  30
Phe Val Tyr Lys Met Ala Ser Ile Leu Pro Val Thr Ser Pro Ser Asn
                35                  40                  45
Val Ser Val Leu Asp Pro Val Pro Lys Gln Ser Gly Phe Lys Gly Pro
 50                  55                  60
Gly Arg Tyr Ile Thr Leu Thr Thr Cys Thr Pro Glu Phe Thr Ser Lys
 65                  70                  75                  80
Tyr Arg Met Ile Val Trp Gly Lys Met
                85
```

<210> SEQ ID NO 65
<211> LENGTH: 89
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 65

Leu Ala Ala His Arg Asp Gly His Gly Ala Arg Phe His Asn Ile Asp
1               5                   10                  15

Lys Ile Glu Lys Gly Asp Pro Ile Val Phe Glu Thr Lys Asp Thr Trp
            20                  25                  30

Tyr Val Tyr Lys Thr Tyr Ala Val Leu Pro Glu Thr Ser Lys Tyr Asn
        35                  40                  45

Val Glu Val Leu Gly Gly Ile Pro Lys Glu Ser Gly Lys Lys Lys Ala
    50                  55                  60

Gly His Tyr Ile Thr Leu Thr Thr Cys Thr Pro Val Tyr Thr Ser Arg
65                  70                  75                  80

Tyr Arg Tyr Val Val Trp Gly Glu Leu
                85

<210> SEQ ID NO 66
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ile Thr Gly His Arg Gly Leu Ala Glu Ala Thr Met Phe Thr Asn Leu
1               5                   10                  15

Asp Lys Val Lys Thr Gly Asp Ser Leu Ile Val Glu Val Phe Gly Glu
            20                  25                  30

Val Leu Thr Tyr Arg Val Thr Ser Thr Lys Val Val Glu Pro Glu Glu
        35                  40                  45

Thr Glu Ala Leu Arg Val Glu Glu Gly Lys Asp Leu Leu Thr Leu Val
    50                  55                  60

Thr Cys Thr Pro Leu Gly Ile Asn Thr His Arg Ile Leu Leu Thr Gly
65                  70                  75                  80

Glu Arg

<210> SEQ ID NO 67
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ile Thr Ala His Arg Gly Leu Ala Glu Ala Thr Met Phe Thr Asn Leu
1               5                   10                  15

Asn Lys Val Gly Val Gly Asp Arg Phe Thr Ile Glu Val Met Gly Glu
            20                  25                  30

Val Leu Thr Tyr Glu Val Arg Glu Thr Arg Val Val Ser Pro Glu Asp
        35                  40                  45

Thr Arg Phe Leu Gln Thr Gln Asp Asp Arg Asp Leu Val Thr Leu Val
    50                  55                  60

Thr Cys Thr Pro Leu Gly Ile Asn Thr His Arg Ile Leu Val Thr Ala
65                  70                  75                  80

Glu Arg

<210> SEQ ID NO 68
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ile Thr Ala His Thr Gly Leu Pro Thr Ala Lys Met Phe Thr Asp Leu
1               5                   10                  15

Thr Lys Leu Lys Val Gly Asp Lys Phe Tyr Val His Asn Ile Lys Glu
            20                  25                  30

Val Met Ala Tyr Gln Val Asp Gln Val Lys Val Ile Glu Pro Thr Asn
        35                  40                  45

Phe Asp Asp Leu Leu Ile Val Pro Gly His Asp Tyr Val Thr Leu Leu
    50                  55                  60

Thr Cys Thr Pro Tyr Met Ile Asn Thr His Arg Leu Leu Val Arg Gly
65                  70                  75                  80

His Arg

<210> SEQ ID NO 69
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ile Thr Ala His Arg Gly Leu Pro Thr Ala Glu Leu Phe Ser Gln Leu
1               5                   10                  15

Asp Lys Met Lys Lys Gly Asp Ile Phe Tyr Leu His Val Leu Asp Gln
            20                  25                  30

Val Leu Ala Tyr Gln Val Asp Gln Ile Val Thr Val Glu Pro Asn Asp
        35                  40                  45

Phe Glu Pro Val Leu Ile Gln His Gly Glu Asp Tyr Ala Thr Leu Leu
    50                  55                  60

Thr Cys Thr Pro Tyr Met Ile Asn Ser His Arg Leu Leu Val Arg Gly
65                  70                  75                  80

Lys Arg

<210> SEQ ID NO 70
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ile Ser Gly His Arg Gly Leu Pro Gln Ala Lys Leu Phe Thr Asp Leu
1               5                   10                  15

Pro Glu Leu Lys Lys Gly Asp Glu Phe Tyr Ile Glu Val Asn Gly Lys
            20                  25                  30

Thr Leu Ala Tyr Gln Val Asp Gln Ile Lys Thr Val Glu Pro Thr Asp
        35                  40                  45

Thr Lys Asp Leu His Ile Glu Ser Gly Gln Asp Leu Val Thr Leu Leu
    50                  55                  60

Thr Cys Thr Pro Tyr Met Ile Asn Ser His Arg Leu Leu Val Arg Gly
65                  70                  75                  80

His Arg

<210> SEQ ID NO 71
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ile Ser Gly His Arg Gly Leu Pro Ser Ala Lys Leu Phe Thr Asn Ile
1               5                   10                  15

Asp Lys Leu Arg Ile Asn Asp Thr Phe Thr Ile Thr Ser Leu Asn Arg
                20                  25                  30

Thr Met Thr Tyr Gln Val Asp Lys Ile Ala Thr Val Leu Pro Asp Asp
            35                  40                  45

Val Ser Leu Leu Arg Ile Glu Glu Gly Lys Asp Leu Val Thr Leu Val
        50                  55                  60

Thr Cys Thr Pro Tyr Gly Val Asn Thr His Arg Leu Leu Val Arg Gly
65                  70                  75                  80

His Arg

<210> SEQ ID NO 72
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ile Ser Ala His Arg Gly Leu Pro Ser Ala Glu Met Phe Thr Asn Leu
1               5                   10                  15

Asn Leu Val Lys Lys Gly Asp Thr Phe Tyr Phe Arg Val Leu Asn Lys
                20                  25                  30

Val Leu Ala Tyr Lys Val Asp Gln Ile Leu Thr Val Glu Pro Asp Gln
            35                  40                  45

Val Thr Ser Leu Ser Gly Val Met Gly Lys Asp Tyr Ala Thr Leu Val
        50                  55                  60

Thr Cys Thr Pro Tyr Gly Val Asn Thr Lys Arg Leu Leu Val Arg Gly
65                  70                  75                  80

His Arg

<210> SEQ ID NO 73
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ile Thr Gly His Ser Gly Leu Ala Asn Ala Thr Leu Phe Asp Asn Leu
1               5                   10                  15

Glu Asp Val Lys Glu His Asp Pro Ile Tyr Ile Thr Val Gln Gly Glu
                20                  25                  30

Thr Leu Lys Tyr Glu Val Asp Ala Ile Asn Val Val Leu Pro Glu Asp

```
                35                  40                  45
Thr Lys Leu Leu Ala Pro Asp Pro Asn Lys Asp Gln Ile Thr Leu Ile
 50                  55                  60
Thr Cys Thr Pro Tyr Ala Val Asn Ser His Arg Leu Leu Val Arg Ala
 65                  70                  75                  80
His Arg

<210> SEQ ID NO 74
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Ile Thr Gly His Thr Gly Leu Ala Asn Ser Thr Met Phe Asp His Leu
 1               5                  10                  15
Asn Lys Ala Glu Lys Gly Asp Thr Phe Tyr Val Gln Val Ser Gly Glu
                20                  25                  30
Lys Leu Lys Tyr Val Val Asp Gln Ile Lys Val Leu Pro Thr Glu
                35                  40                  45
Thr Glu Asp Leu Arg Pro Glu Gln Gly Lys Asp Tyr Ile Thr Leu Ile
 50                  55                  60
Thr Cys Thr Pro Tyr Gly Ile Asn Thr His Arg Leu Met Val Arg Gly
 65                  70                  75                  80
His Gln

<210> SEQ ID NO 75
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Leu Ser Ala His Thr Gly Leu Gln Asn Ala Thr Leu Trp Asp Asn Leu
 1               5                  10                  15
Ile Gln Ile Lys Lys Gly Asp Pro Val Tyr Val Ala Ala Gly Glu
                20                  25                  30
Lys Leu Lys Tyr Glu Val Arg Asn Ile Glu Val Val Thr Pro Asp Lys
                35                  40                  45
Thr Ser Leu Leu Arg Arg Thr Ser Asn Lys Asp Gln Val Thr Leu Ile
 50                  55                  60
Thr Cys Thr Pro Tyr Gly Ile Asn Thr His Arg Leu Ile Ile Thr Ala
 65                  70                  75                  80
Glu Arg

<210> SEQ ID NO 76
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Leu Thr Ala His Ser Gly Ile Gln Lys Ser Thr Phe Phe Asp Asn Leu
 1               5                  10                  15
```

Glu Lys Val Lys Lys Gly Asp Ala Ile Tyr Val Arg Asn Ile Gly Glu
            20                  25                  30

Thr Leu Lys Tyr Gln Val Arg Asp Ile Glu Ile Ile Arg Pro Ala Glu
            35                  40                  45

Ile Asp Arg Ile Gln Pro Ile Pro Asp Arg Asp Leu Ile Thr Leu Val
50                  55                  60

Thr Cys Thr Pro Tyr Gly Ile Asn Thr His Arg Leu Leu Val Thr Ala
65                  70                  75                  80

Glu Arg

<210> SEQ ID NO 77
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Ile Ala Gly His Arg Gly Tyr Arg Gly Asn Arg His Phe Ser Arg Leu
1               5                   10                  15

Pro Asp Val Thr Ile Gly Asp Glu Val Phe Leu His Thr Lys Glu Glu
            20                  25                  30

Thr Phe Val Tyr Lys Val Thr Asp Ile Ser Ile Ile Glu Pro Thr Asp
            35                  40                  45

Val Asp Val Leu Asp Asp Arg Asp Gly Lys His Glu Ile Thr Met Ile
50                  55                  60

Thr Cys Thr Arg Ser Gly Lys Gln Arg Val Ala Val Arg Gly Glu Leu
65                  70                  75                  80

<210> SEQ ID NO 78
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ile Ala Gly His Arg Gly Tyr Arg Gly Asn Arg His Phe Ser Arg Leu
1               5                   10                  15

Pro Asp Val Thr Ile Gly Asp Glu Val Phe Leu His Thr Lys Glu Glu
            20                  25                  30

Thr Phe Val Tyr Lys Val Thr Asp Ile Ser Ile Ile Glu Pro Thr Asp
            35                  40                  45

Val Asp Ile Leu Asp Asp Arg Asp Gly Lys His Glu Ile Thr Met Ile
50                  55                  60

Thr Cys Thr Arg Ser Gly Lys Gln Arg Val Ala Val Arg Gly Val Leu
65                  70                  75                  80

<210> SEQ ID NO 79
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Leu Ala Ser His His Val Phe Gly Met Thr Gly Ser Ser Gln Met Leu

```
              1               5                  10                  15
              Phe Ser Pro Leu Glu Arg Ala Lys Glu Gly Met Glu Ile Tyr Leu Thr
                          20                  25                  30

Asp Lys Asn Lys Val Tyr Thr Tyr Val Ile Ser Glu Val Lys Thr Val
                          35                  40                  45

Thr Pro Glu His Val Glu Val Ile Asp Asn Arg Pro Gly Gln Asn Glu
                          50                  55                  60

Val Thr Leu Val Thr Cys Thr Asp Ala Gly Ala Thr Ala Arg Thr Ile
              65                  70                  75                  80

Val His Gly Thr Tyr Lys
                                  85

<210> SEQ ID NO 80
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Leu Ala Ser His His Ile Phe Gly Ile Thr Gly Ser Ser Gln Met Leu
              1               5                  10                  15

Phe Ser Pro Leu Glu Arg Ala Gln Asn Gly Met Ser Ile Tyr Leu Thr
                          20                  25                  30

Asp Lys Glu Lys Ile Tyr Glu Tyr Ile Ile Lys Asp Val Phe Thr Val
                          35                  40                  45

Ala Pro Glu Arg Val Asp Val Ile Asp Asp Thr Ala Gly Leu Lys Glu
                          50                  55                  60

Val Thr Leu Val Thr Cys Thr Asp Ile Glu Ala Thr Glu Arg Ile Ile
              65                  70                  75                  80

Val Lys Gly Glu Leu Lys
                                  85

<210> SEQ ID NO 81
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Leu Ala Ser His His Ile Phe Gly Val Asp Asn Ala Asn Lys Met Leu
              1               5                  10                  15

Phe Ser Pro Leu Asp Asn Ala Lys Asn Gly Met Lys Ile Tyr Leu Thr
                          20                  25                  30

Asp Lys Asn Lys Val Tyr Thr Tyr Glu Ile Arg Glu Val Lys Arg Val
                          35                  40                  45

Thr Pro Asp Arg Val Asp Glu Val Asp Arg Asp Gly Val Asn Glu
                          50                  55                  60

Ile Thr Leu Val Thr Cys Glu Asp Leu Ala Ala Thr Glu Arg Ile Ile
              65                  70                  75                  80

Val Lys Gly Asp Leu Lys
                                  85

<210> SEQ ID NO 82
<211> LENGTH: 82
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 82

Leu Ala Ser His Arg Thr Glu Asp Gly Val Ser Leu Phe Ser Pro Leu
1               5                   10                  15

Glu Arg Thr Lys Lys Asp Glu Leu Ile Tyr Ile Thr Asp Leu Ser Thr
            20                  25                  30

Val Tyr Thr Tyr Lys Ile Thr Ser Val Glu Lys Ile Glu Pro Thr Arg
        35                  40                  45

Val Glu Leu Ile Asp Asp Val Pro Gly Gln Asn Met Ile Thr Leu Ile
    50                  55                  60

Thr Cys Gly Asp Leu Gln Ala Thr Thr Arg Ile Ala Val Gln Gly Thr
65                  70                  75                  80

Leu Ala

<210> SEQ ID NO 83
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Val Asp His His Glu Gly Phe Tyr Tyr Asp Thr Leu Tyr Asn Arg Tyr
1               5                   10                  15

Asp Val Glu Val Phe Ser Ala Tyr Val Thr Thr Thr Asp Phe Tyr Tyr
            20                  25                  30

Ile Glu Thr Glu Phe Pro Ser Lys Asp Tyr Lys Ala Phe Leu Asn
        35                  40                  45

Glu Leu Lys Lys Arg Ser Val Val Gln Thr Asn Val Glu Val Gly Glu
    50                  55                  60

Glu Asp Gln Ile Ile Thr Leu Ser Thr Cys Asp Tyr Arg Leu Asp Arg
65                  70                  75                  80

Asp Arg Gly Arg Leu Val Val His Gly Lys Leu
                85                  90

<210> SEQ ID NO 84
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Phe Met Ser His Arg Lys Leu Tyr Tyr Asp Thr Leu Phe Glu Gly Tyr
1               5                   10                  15

Asp Leu Glu Val Phe Ser Val Tyr Thr Thr Thr Thr Asp Phe Tyr Tyr
            20                  25                  30

Ile Glu Thr Asp Phe Ser Ser Asp Thr Glu Tyr Thr Ser Phe Leu Glu
        35                  40                  45

Lys Ile Gln Glu Lys Ser Leu Tyr Lys Thr Asp Thr Thr Val Thr Ala
    50                  55                  60

Gly Asp Gln Ile Val Thr Leu Ser Thr Cys Asp Tyr Ala Leu Asp Pro
65                  70                  75                  80
```

Glu Ala Gly Arg Leu Val Val His Ala Lys Leu
                85                  90

<210> SEQ ID NO 85
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Tyr Glu Lys His Lys Ile Ile Glu Phe Asp Asn Lys Tyr Gly Lys Tyr
1               5                   10                  15

Gln Leu Gln Val Phe Ser Ala Tyr Lys Thr Thr Lys Asp Asn Tyr
            20                  25                  30

Ile Arg Thr Asp Phe Glu Asn Asp Gln Asp Tyr Gln Gln Phe Leu Asp
            35                  40                  45

Glu Thr Lys Arg Lys Ser Val Ile Asn Ser Asp Val Asn Val Thr Val
50                  55                  60

Lys Asp Lys Ile Met Thr Leu Ser Thr Cys Glu Asp Ala Tyr Ser Glu
65                  70                  75                  80

Thr Thr Lys Arg Ile Val Val Ala Lys Ile
                85                  90

<210> SEQ ID NO 86
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Phe Asn Lys His Lys Glu Phe Ser Ile Glu Thr Lys Thr Lys Gln Lys
1               5                   10                  15

Leu Lys Ile Asn Ile Phe Ala Cys Ile Gln Thr Asp Ala Phe Asp Ser
            20                  25                  30

Leu Leu Phe Asn Pro Ile Asp Val Asp Ile Ser Ser Lys Asn Glu Phe
            35                  40                  45

Leu Asn His Ile Lys Gln Lys Ser Val Gln Tyr Arg Glu Ile Leu Thr
50                  55                  60

Thr Asn Glu Ser Arg Phe Val Ala Leu Ser Thr Cys Glu Asp Met Thr
65                  70                  75                  80

Thr Asp Gly Arg Ile Ile Val Ile Gly Gln Ile
                85                  90

<210> SEQ ID NO 87
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Phe Asn Lys His Asn Lys Ala Ile Ile Glu Thr Lys Glu Arg Lys Lys
1               5                   10                  15

Leu Thr Val Thr Ile Phe Ala Cys Leu Lys Thr Asp Ala Phe Asp Gln
            20                  25                  30

Leu Val Phe Asn Pro Asn Ala Ile Thr Asn Gln Asp Gln Gln Lys Gln

```
                35                  40                  45
Leu Val Asp Tyr Ile Ser Lys Arg Ser Lys Gln Phe Lys Pro Val Lys
 50                  55                  60

Leu Lys His His Thr Lys Phe Val Ala Phe Ser Thr Cys Glu Asn Phe
 65                  70                  75                  80

Ser Thr Asp Asn Arg Val Ile Val Val Gly Thr Ile
                 85                  90
```

<210> SEQ ID NO 88
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Ile Ala Gly His Arg Ala Glu Pro Ser His Val Phe Phe Arg His Leu
 1               5                  10                  15

Asp Gln Leu Lys Val Gly Asp Ala Leu Tyr Tyr Asp Asn Gly Gln Glu
                 20                  25                  30

Ile Val Glu Tyr Gln Met Met Asp Thr Glu Ile Ile Leu Pro Ser Glu
             35                  40                  45

Trp Glu Lys Leu Glu Ser Val Ser Ser Lys Asn Ile Met Thr Leu Ile
 50                  55                  60

Thr Cys Asp Pro Ile Pro Thr Phe Asn Lys Arg Leu Leu Val Asn Phe
 65                  70                  75                  80

Glu Arg
```

<210> SEQ ID NO 89
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Leu Ala Gly His Asn Met Ser Lys Lys Gly Val Leu Phe Ser Asp Ile
 1               5                  10                  15

Ala Ser Leu Lys Lys Gly Asp Lys Ile Tyr Leu Tyr Asp Asn Glu Asn
                 20                  25                  30

Glu Tyr Glu Tyr Ala Val Thr Gly Val Ser Glu Val Thr Pro Asp Lys
             35                  40                  45

Trp Glu Val Val Glu Asp His Gly Lys Asp Glu Ile Thr Leu Ile Thr
 50                  55                  60

Cys Val Ser Val Lys Asp Asn Ser Lys Arg Tyr Val Val Ala Gly Asp
 65                  70                  75                  80

Leu
```

<210> SEQ ID NO 90
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Leu Ala Gly His His Leu Lys Gln Lys Asn Leu Leu Phe Gly Pro Leu

```
1               5                   10                  15
Glu Asn Ile Lys Thr Gly Ala Gln Ile Val Ile Thr Asp Phe Lys Lys
            20                  25                  30

Asp Tyr Ile Tyr Ser Val Thr Ser Lys Asp Ile Ile Ser Glu Met Asp
            35                  40                  45

Ala Asp Val Val Glu Glu Thr Asn Lys Lys Glu Ile Thr Leu Ile Thr
    50                  55                  60

Cys Asp Lys Ala Val Lys Thr Glu Gly Arg Leu Val Val Lys Gly Glu
65                  70                  75                  80

Leu

<210> SEQ ID NO 91
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Leu Ala Ser His Asn Ala Gly Tyr Glu Gly Leu Leu Phe Thr Ser Leu
1               5                   10                  15

Asn Lys Val Ser Val Gly Asp Leu Val Lys Leu Asn Asp Arg Glu Gly
            20                  25                  30

His Ser Phe Ile Tyr Lys Val Lys Glu Gln Lys His Val Asp Met Thr
            35                  40                  45

Asp Thr Thr Met Leu Asn Leu Thr Arg Lys Pro Thr Leu Thr Leu Ile
    50                  55                  60

Thr Cys Asp Gln Ala Thr Lys Thr Thr Gly Arg Ile Ile Val Ile Ala
65                  70                  75                  80

Glu Leu

<210> SEQ ID NO 92
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Ile Ala Gly His Thr Phe Ile Asp Arg Pro Asn Tyr Gln Phe Thr Asn
1               5                   10                  15

Leu Lys Ala Ala Lys Lys Gly Ser Met Val Tyr Phe Lys Val Gly Asn
            20                  25                  30

Glu Thr Arg Lys Tyr Lys Met Thr Ser Ile Arg Asp Val Lys Pro Thr
            35                  40                  45

Asp Val Gly Val Leu Asp Glu Gln Lys Gly Lys Asp Lys Gln Leu Thr
    50                  55                  60

Leu Ile Thr Cys Asp Asp Tyr Asn Glu Lys Thr Gly Val Trp Glu Lys
65                  70                  75                  80

Arg Lys Ile Phe

<210> SEQ ID NO 93
<211> LENGTH: 82
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 93

Ile Ala Gly His Arg Asp Thr His Phe Ala Ile Leu Lys Gly Met Thr
1               5                   10                  15

Val Gly Arg Arg Leu Ala Leu Gln Thr Ala Ala Gly Lys Glu Ile Val
            20                  25                  30

Tyr Gln Val Val Ala Thr Lys Val His Glu Ser Gln Thr Glu Leu
        35                  40                  45

Met Ala Pro Ser Asp Asp Asn Arg Leu Thr Leu Ile Thr Cys Tyr Pro
    50                  55                  60

Phe Asp Ala Leu Gln Gly Val Ala Glu Leu Arg Phe Val Val Gln Ala
65                  70                  75                  80

Val Pro

<210> SEQ ID NO 94
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Val Leu Gly His Val Thr Val Gly Arg Tyr Asp Gly Val Phe Arg His
1               5                   10                  15

Leu Ala Gly Arg Arg Gly Glu Arg Ile Glu Ala Arg Glu Asn Gly Thr
            20                  25                  30

Thr Ala Glu Phe Thr Thr Ala Val Arg Thr Val Ala Lys Asp Phe Pro
        35                  40                  45

Thr Asp Asp Val Tyr Gly Val Ala Pro Glu Leu Arg Leu Ile Thr Cys
    50                  55                  60

Gly Pro Arg Asp Gly Gln Glu Tyr Arg Asp Asn Val Ile Val Ala Glu
65                  70                  75                  80

Leu

<210> SEQ ID NO 95
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ile Tyr Gly His Asn Met Lys Asn Lys Thr Met Phe Asn Asn Leu Asn
1               5                   10                  15

Lys Phe Lys Asp Ala Asp Phe Phe Lys Lys Asn Asn Lys Ile Lys Ile
            20                  25                  30

Thr Leu Asn Gly Lys Glu Phe Leu Tyr Asp Val Phe Ser Ala Tyr Ile
        35                  40                  45

Val Glu Ser Asp Tyr Asp Tyr Leu Lys Thr Asn Phe Asn Asn Glu Ser
    50                  55                  60

Asp Tyr Gln Asn Tyr Ile Asn Asp Ile Thr Ser Lys Ser Leu Tyr Lys
65                  70                  75                  80

Ser Pro Ile Lys Val Asn Ser Asn Asp Lys Ile
                85                  90

```
<210> SEQ ID NO 96
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ile Leu Gly His Arg Thr Thr Tyr Ser Gly Pro Phe Arg Lys Ile Gly
1               5                   10                  15

Ala Leu Arg Lys Gly Asp Arg Val Ile Ile Glu Asp Ala Ser Ser Ser
            20                  25                  30

Ile Arg Tyr Ile Tyr Thr Val Thr Ser Asn Gly Asp Asp Ile Arg Trp
        35                  40                  45

Asp Tyr Arg Thr Asn Pro Val Arg Phe Ser Gln Ser Gly Asp Ala Arg
    50                  55                  60

Leu Met Leu Ile Thr Cys Tyr Pro Pro Gly Gln Lys Lys Ala Ala Trp
65              70                  75                  80

Ile Thr His Cys Lys Leu
                85

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Leu Pro Ile Thr Gly
1               5

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Leu Pro Asp Thr Ala
1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Pro Lys Thr Gly
1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 100

Leu Ala Glu Thr Gly
1               5

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Ala Ala Thr Gly
1               5

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Leu Ala His Thr Gly
1               5

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Leu Ala Ser Thr Gly
1               5

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Leu Pro Leu Thr Gly
1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Ser Arg Thr Gly
1               5

<210> SEQ ID NO 106
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 106

Val Pro Asp Thr Gly
1               5

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ile Pro Gln Thr Gly
1               5

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Tyr Pro Arg Thr Gly
1               5

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Leu Pro Met Thr Gly
1               5

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Leu Ala Leu Thr Gly
1               5

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Leu Gly Asn Thr Gly
1               5
```

```
<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Leu Ala Phe Thr Gly
1               5

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Leu Pro Gln Thr Ser
1               5

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 114

Thr Leu Xaa Thr Cys
1               5

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Met Pro Gln Thr Asn
1               5

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asn Pro Gln Thr Asn
1               5

<210> SEQ ID NO 117
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Abz
<220> FEATURE:
<221> NAME/KEY: MOD_RES
<222> LOCATION: (7)..(7)
<223> OTHER INFORMATION: Dap(Dnp)

<400> SEQUENCE: 117

Xaa Leu Pro Glu Thr Gly Xaa
1               5

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid except Pro or Cys

<400> SEQUENCE: 118

Leu Pro Xaa Thr Gly
1               5

<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Met
<220> FEATURE:
<221> NAME/KEY: MOD_RES
<222> LOCATION: (3)..(3)
<223> OTHER INFORMATION: Any amino acid except Pro or Cys
<220> FEATURE:
<221> NAME/KEY: MOD_RES
<222> LOCATION: (4)..(4)
<223> OTHER INFORMATION: Ala, Leu, Ser, Thr or Val

<400> SEQUENCE: 119

Xaa Pro Xaa Xaa Gly
1               5

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ile Pro Lys Thr Gly
1               5

<210> SEQ ID NO 121
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ile Pro Ala Leu Gly
1               5

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Leu Ala Ala Ser Ser
1               5

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Leu Pro Ala Thr Gly
1               5

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Leu Pro Ile Ser Ser
1               5

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Leu Pro Lys Thr Ser
1               5

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Leu Pro Glu Thr Gly Gly His His His His His His
```

```
                1               5                   10
```

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Tyr Ala Leu Pro Glu Thr
1               5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Tyr Ala Leu Pro Met Thr Gly Lys
1               5

<210> SEQ ID NO 129
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 129

Leu Pro Xaa Thr
1

<210> SEQ ID NO 130
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 130

Leu Pro Xaa Ala
1

<210> SEQ ID NO 131
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

```
<400> SEQUENCE: 131

Ser Pro Xaa Thr
1

<210> SEQ ID NO 132
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 132

Leu Ala Xaa Thr
1

<210> SEQ ID NO 133
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 133

Leu Ser Xaa Thr
1

<210> SEQ ID NO 134
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 134

Asn Pro Xaa Thr
1

<210> SEQ ID NO 135
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 135

Val Pro Xaa Thr
1

<210> SEQ ID NO 136
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 136

Ile Pro Xaa Thr
1

<210> SEQ ID NO 137
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 137

Leu Gly Xaa Thr
1

<210> SEQ ID NO 138
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 138

Tyr Pro Xaa Arg
1

<210> SEQ ID NO 139
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Leu Pro Ser Thr
1

<210> SEQ ID NO 140
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Leu Pro Lys Thr
1
```

<210> SEQ ID NO 141
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Leu Pro Ile Thr
1

<210> SEQ ID NO 142
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Leu Pro Asp Thr
1

<210> SEQ ID NO 143
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ser Pro Lys Thr
1

<210> SEQ ID NO 144
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Leu Ala Glu Thr
1

<210> SEQ ID NO 145
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Leu Ala Ala Thr
1

<210> SEQ ID NO 146
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Leu Ala Ser Thr
1

<210> SEQ ID NO 147
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Leu Pro Leu Thr
1

<210> SEQ ID NO 148
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Leu Ser Arg Thr
1

<210> SEQ ID NO 149
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Leu Pro Glu Thr
1

<210> SEQ ID NO 150
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Val Pro Asp Thr
1

<210> SEQ ID NO 151
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ile Pro Gln Thr
1

<210> SEQ ID NO 152
<211> LENGTH: 4

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Tyr Pro Arg Arg
1

<210> SEQ ID NO 153
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Leu Pro Met Thr
1

<210> SEQ ID NO 154
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Leu Ala Phe Thr
1

<210> SEQ ID NO 155
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Leu Pro Gln Thr
1

<210> SEQ ID NO 156
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Ile, Val or Met
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Thr, Ser or Ala

<400> SEQUENCE: 156

Xaa Pro Xaa Xaa
1
```

```
<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Tyr Pro Arg Arg Gly
1               5

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 158

Leu Pro Xaa Ala Gly
1               5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Leu Pro Asn Ala Gly
1               5

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Leu Pro Asn Thr Ala
1               5

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 161

Leu Gly Xaa Thr Gly
1               5
```

```
<210> SEQ ID NO 162
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Leu Gly Ala Thr Gly
1               5

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 163

Ile Pro Xaa Thr Gly
1               5

<210> SEQ ID NO 164
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ile Pro Asn Thr Gly
1               5

<210> SEQ ID NO 165
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ile Pro Glu Thr Gly
1               5

<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Glu, Ala, Asn, Gln, Lys or Arg

<400> SEQUENCE: 166

Leu Pro Xaa Thr Gly
1               5

<210> SEQ ID NO 167
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Glu, Ala, Asn, Gln, Lys or Arg

<400> SEQUENCE: 167

Leu Pro Xaa Thr
1

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Glu, Asn, Gln or Ala

<400> SEQUENCE: 168

Leu Pro Xaa Thr Gly
1               5

<210> SEQ ID NO 169
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys, Glu, Asn, Gln or Ala

<400> SEQUENCE: 169

Leu Pro Xaa Thr
1

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Glu, Ala, Asn, Gln, Lys or Arg
<220> FEATURE:
<221> NAME/KEY: MOD_RES
<222> LOCATION: (5)..(5)
<223> OTHER INFORMATION: Ala or Gly

<400> SEQUENCE: 170

Leu Pro Xaa Thr Xaa
1               5

<210> SEQ ID NO 171
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Glu, Ala, Asn, Gln, Lys or Arg

<400> SEQUENCE: 171

Leu Pro Xaa Thr Ala
1               5

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (3)..(3)
<223> OTHER INFORMATION: This sequence may encompass 1-10 residues

<400> SEQUENCE: 172

Gly Gly Gly Gly Gly Gly Gly Gly Gly Gly
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Leu Pro Glu Thr Gly His His His His His
1               5                   10

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 174

Ala Leu Pro Glu Thr Gly Gly Arg Arg
1               5

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 175

Ala Leu Pro Glu Thr Gly Gly Arg Arg Cys
```

```
1               5               10
```

<210> SEQ ID NO 176
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 176

```
Ala Leu Pro Glu Thr Gly Gly Gly Trp Trp
1               5               10
```

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

```
Leu Pro Glu Thr Gly Gly Arg Arg Cys
1               5
```

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

```
Gly Gly Trp Trp Lys
1               5
```

<210> SEQ ID NO 179
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

```
Gly Gly Arg Arg
1
```

<210> SEQ ID NO 180
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

```
Leu Pro Glu Thr Cys
1               5
```

<210> SEQ ID NO 181
<211> LENGTH: 4

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Ala Ala Ala
1

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala

<400> SEQUENCE: 182

Ala Leu Pro Glu Thr Gly Gly Gly Gly
1               5
```

TRANSAMIDATION REACTION IN DEEP EUTECTIC SOLVENTS

Herein is reported a transamidation reaction using sortase in deep eutectic solvents.

SEQUENCE LISTING

This application contains a Sequence Listing which has been submitted via EFS-Web and is hereby incorporated by reference in its entirety. Said ASCII copy, created on Oct. 21, 2019, is named P33091-US_SL.txt and is 92,510 bytes in size.

BACKGROUND OF THE INVENTION

Deep eutectic solvents (DESs) are water free solutions with melting points below 100° C. DESs are based on hydrogen bonds. In DES the properties of water and organic solvents are combined. Most DESs are liquid at suitable temperatures for biocatalysis. DESs are more hydrophobic than water however in some cases they do not lead to hydrophobicity induced inactivation of the biocatalyst (Gorke, J., et al., Biotechnol. Bioprocess E 15 (2010) 40-53). Additionally deep eutectics solvents can be produced water free and are therefore inert for hydrolysis. Ionic liquids have similar properties as DES, but are more difficult to produce and more harmful to the environment. Proteases have shown activity in DES (Zhao, H., et al., J. Mol. Catal. B-Enzym 72 (2011) 163-167).

Additionally, some studies suggest that DES are more enzyme compatible solvents than the conventional organic ones (Gorke, J. T., et al., Chem. Commun. (2008) 1235-1237; Lindberg, D., et al., J. Biotechnol 147 (2010) 169-171).

The DES which showed the best performance for several enzyme catalyzed reactions is a mixture of choline chloride and glycerol in the molar ratio of 1:2 (Gorke, J. T., et al., Chem. Commun. (2008) 1235-1237; Zhao, H., et al., J. Mol. Catal. B-Enzym 72 (2011) 163-167). Sortase A (SrtA) is a membrane bound enzyme which attaches proteins covalently to the bacterial cell wall. The specific recognition motif on the SrtA substrate is LPXTG (SEQ ID NO: 1), whereby the enzyme cleaves between the residues threonine and glycine. The recognition motif on the peptidoglycan is a pentaglycine motif (SEQ ID NO: 31). It has been shown that a triglycine (SEQ ID NO: 29) and even a diglycine motif (SEQ ID NO: 28) on the N-terminus is sufficient to support the SrtA reaction (Clancy, K. W., et al., Peptide science 94 (2010) 385-396). The reaction proceeds through a thioester acyl-enzyme intermediate, which is resolved by the attack of an amine nucleophile from the oligoglycine, covalently linking peptidoglycan to a protein substrate and regenerating SrtA. SrtA can be used to covalently conjugate chemically synthesized peptides to recombinantly expressed proteins.

Applicable Sortases for technical bioconjugation are limited. The most wildly used *Staphylococcus aureus* Sortase A (St.au. SrtA) shows suitable conversion kinetics for technical application but has a limited substrate spectrum, only recognizing LPXTG sortase-motives (SEQ ID NO: 1). The St.au. SrtA, that lacks the N-terminal membrane-anchoring motif, has been used for cell-surface protein labeling, covalent protein immobilization and incorporation of novel functionality into proteins. For orthogonal/dual labeling strategies, sortases with new substrate spectra are needed. The same holds true for standard sortase mediated bioconjugation approaches where a LPXTG motive (SEQ ID NO: 1) in the product has e.g. negative effects on its structure and/or function. Therefore sortases with recognition sequences different from LPXTG (SEQ ID NO: 1) would be of high value. The *Staphylococcus pyogenes* SrtA (St.py. SrtA) recognizes a LPXTA sortase-motives (SEQ ID NO: 41), however the conversion kinetic parameter of the enzyme turn it in to a not suitable sortase on a technical scale.

Sortases that accept sortase-motives different from LPXTG (SEQ ID NO: 1) are reported in literature. Thereunder are wild-types e.g. Sortase A from *Streptococcus pyogenes* (St.py. SrtA) and Sortase A from *Clostridium difficile* (Cl.di. SrtA) as well as engineered sortase. Beside the St.py. SrtA none of the reported sortase recognizes a LPXTA motif (SEQ ID NO: 41) (see e.g. van Leeuwen, H. C., et al., FEBS Lett. 588 (2014) 4325-4333; Don, B. M., et al., Proc. Natl. Acad. Sci. USA 111 (2014) 13343-13348; Bentley, M. L., et al., J. Biol. Chem. 282(2007) 6571-6581; Race, P. R., et al., J. Biol. Chem. 284 (2009) 6924-33; Antos, J. M., et al., J. Am. Chem. Soc. 131 (2009) 10800-10801).

Sortase reactions are performed in aquatic solutions which has several drawbacks. One is that many compounds have a low solubility in water—this is especially true for many fluorophores. Additionally sortases have a very low Km making hydrophobic substrate not accessible for sortase reactions (Chen, I., et al., Proc. Natl. Acad. Sci. USA 108 (2011) 11399-11404). However, antibody/binding-proteins linked to a fluorophore are probably the most important application in bioconjugation (Shreve, P. and Aisen, A. M., Magnetic resonance in medicine: official journal of the Society of Magnetic Resonance in Medicine/Society of Magnetic Resonance in Medicine 3 (1986) 336-340; Drapkin, R. L., et al., Am. J. Hematol. 7 (1979) 163-172). Another issue is the enzyme intermediate which is formed during the reaction. It can be hydrolyzed which leads to product loss. This makes water free and organic solvents an interesting alternative to water. However sortases are not stable in organic solvents e.g. more than 20% Dimethyl sulfoxide (DMSO) diminishes sortase activity (Pritz, S. (2008) Enzymatische Ligation von Peptiden, Peptidnucleinsauren and Proteinen).

In WO 2010/087994 methods for ligation and uses thereof are reported. Recombinant approaches to IgG-like bispecific antibodies are reported by Marvin, J. S., et al. (Acta Pharmacol. Sinica 26 (2005) 649-658). In WO 2013/003555 the use of sortases to install click chemistry handles for protein ligation is reported.

Strijbis, K. et al (Traffic 13 (2012) 780-789) report protein ligation in living cells using sortase. It has been stated by them that the $Ca^{2+}$-dependent *S. aureus* sortase A is not functional intracellularly, but that the $Ca^{2+}$-independent *S. pyogenes* sortase A is functional in the cytosol and endoplasmic reticulum (ER) lumen of both *Saccharomyces cerevisiae* and mammalian HEK293T cells.

Levary, D. A., et al., report protein-protein fusion catalyzed by Sortase A (PLOS ONE 6 (2011)). Engineering of an anti-epidermal growth factor receptor antibody to single chain format and labeling by sortase A-mediated protein ligation is reported by Madej, M. P., et al. (Biotechnol. Bioeng. 109 (2012) 1461-1470). Ta, H. T., et al., report enzymatic single-chain antibody tagging as a universal approach to targeted molecular imaging and cell homing in cardiovascular diseases (Cir. Res. 109 (2011) 365-373). Popp, M., et al., report making and breaking peptide bonds—protein engineering using sortase (Angew. Chem. Int. Ed. Eng. 50 (2011) 5024-5032). Engineered proteins with high affinity for DOTA chelates are reported in WO 2010/099536.

Different efforts to block the reverse reactions of Sortase have been reported. Yamamura, Y., et al. (Chem. Commun. 47 (2011) 4742-4744) reported enhancement of sortase A-mediated protein ligation by inducing a beta-hairpin structure around the ligation site by introducing a β-hairpin around the recognition site of the substrate. Sorting of LPXTG (SEQ ID NO: 1) peptides by archetypal sortase A, role of invariant substrate residues in modulating the enzyme dynamics and conformational signature of a productive substrate was reported by Biswas, T., et al. (Biochem. 53 (2014) 2515-2524).

Li, Y. M., et al. report irreversible site-specific hydrazinolysis of proteins by use of Sortase (Angew. Chem. Int. Ed. Engl. 53 (2014) 2198-2202).

Ling and co-workers showed the introduction of a thioester via a sortase (Ling, J. J. J., et al., J. Am. Chem. Soc. 134 (2012) 10749-10752).

Lindberg, D., et al. (J. Biotechnol. 147 (2010) 169-171) reported deep eutectic solvents (DESs) are viable co-solvents for enzyme-catalyzed epoxide hydrolysis. Gorke, J. T., et al. reported hydrolase-catalyzed biotransformations in deep eutectic solvents (Chem. Commun. (2008) 1235-1237).

In U.S. Pat. No. 8,247,198 enzymatic processing in deep eutectic solvents is reported.

Bellucci, J. J., et al. report the use of lysine as nucleophile (Angew. Chem. Int. Ed. Engl. 53 (2014) 1-6).

WO 2013/016653 provides methods for detecting the concurrent presence of at least two targets within a biological sample. The method includes contacting said biological sample with a first binding agent, said first binding agent operably linked to a first sortase molecule, wherein said first binding agent specifically binds to a first target; contacting said biological sample with a second binding agent, said second binding agent operably linked to a first sortase recognition sequence peptide, wherein said second binding agent specifically binds to a second target; adding a sortase substrate under conditions where a first sortase-mediated ligation of the sortase substrate to the first sortase recognition sequence will produce a ligation product, and detecting the ligation product, wherein detection of said ligation product indicates the concurrent presence of the first target and the second target in the biological sample.

Schmohl, L. and Schwarzer, D., reported about sortase-mediated ligations for the site-specific modification of proteins (Curr. Opin. Chem. Biol. 22 (2014) 122-128).

SUMMARY OF THE INVENTION

It has been found that a transpeptidation reaction can be performed in deep eutectic solvents. It has further been found that the reduction or even absence of water is not detrimental to the reaction but suppresses hydrolysis side reaction.

One aspect as reported herein is a method for the enzymatic production of a polypeptide comprising the following step incubating
i) a first polypeptide (optionally comprising within the 100 C-terminal amino acid residues) the amino acid sequence LPXTG (SEQ ID NO: 01, wherein X can be any amino acid residue) or LPXTA (SEQ ID NO: 41, wherein X can be any amino acid residue),
ii) a second polypeptide comprising i) a glycinyl, an alaninyl, or a cysteinyl compound at its N-terminus (i.e. a compound that comprises a cysteine amino acid residue with free alpha amino group, e.g. as $NH_2$ or $NH_{3+}$, and a carboxy group, which is part of a peptide bond, at position 1, or a compound that comprises an alanine amino acid residue with free alpha amino group, e.g. as $NH_2$ or $NH_{3+}$, and a carboxy group, which is part of a peptide bond, at position 1, or a compound that comprises a glycine amino acid residue with free alpha amino group, e.g. as $NH_2$ or $NH_{3+}$, and a carboxy group, which is part of a peptide bond), at position 1, or ii) an oligoglycine, or oligoalanine, or a cysteine amino acid residue followed by one to three glycine or alanine amino acid residues at its N-terminus, or iii) a lysine amino acid residue within its 5 N-terminal amino acid residues, and
iii) a third polypeptide with sortase A activity (i.e. a third polypeptide that is a sortase A or a catalytically active fragment thereof, i.e. that has sortase A activity), in a deep eutectic solvent
and thereby producing a polypeptide.

In one embodiment the third polypeptide with sortase A activity is derived from *Staphylococcus aureus* sortase A, or from *Streptococcus pyogenes* Sortase A, or from *Listeria monocytogenes* Sortase A.

In one embodiment the third polypeptide is derived from *Staphylococcus aureus* sortase A, or from *Streptococcus pyogenes* Sortase A, or from *Listeria monocytogenes* Sortase A.

In one embodiment the third polypeptide with sortase A activity is derived from *Staphylococcus aureus* sortase A, or from *Streptococcus pyogenes* Sortase A, from *Listeria monocytogenes* Sortase A, or a catalytically active fragment thereof.

In one embodiment the third polypeptide comprises the amino acid sequence of SEQ ID NO: 05, SEQ ID NO: 06, or SEQ ID NO: 38. In one preferred embodiment the third polypeptide comprises the amino acid sequence of SEQ ID NO: 38.

In one embodiment the third polypeptide comprises additionally a tag at its N- or C-terminus either conjugated directly or via an intervening linker. In one embodiment the third polypeptide is consisting of the amino acid sequence of SEQ ID NO: 38 and the C-terminal tag of SEQ ID NO: 32. In one embodiment the third polypeptide is consisting of the amino acid sequence of SEQ ID NO: 38.

In one embodiment the method is for the enzymatic conjugation of two polypeptides. In one embodiment the method is for the enzymatic transpeptidation of two polypeptides. In one embodiment the first or the second or both polypeptides are insoluble in water (100% (v/v)).

In one embodiment the deep eutectic solvent comprises choline chloride. In one embodiment the deep eutectic solvent is a mixture of choline chloride with glycerol at a molar ratio of 1:2. In one embodiment the deep eutectic solvent comprises an aqueous co-solvent. In one embodiment the deep eutectic solvent comprises up to 30% (v/v) aqueous co-solvent. In one embodiment the deep eutectic solvent comprises from (and including) 20% (v/v) aqueous co-solvent to (and including) 30% (v/v) aqueous co-solvent. In one preferred embodiment the deep eutectic solvent comprises about 25% (v/v) aqueous co-solvent. In one embodiment the deep eutectic solvent comprises up to 15% (v/v) aqueous co-solvent. In one embodiment the deep eutectic solvent is a mixture of choline chloride with glycerol at a molar ratio of 1:2 comprising up to 5% (v/v) aqueous co-solvent. In one embodiment the deep eutectic solvent is a mixture of choline chloride with glycerol at a molar ratio of 1:2 comprising up to 30% (v/v) aqueous co-solvent.

In one embodiment the incubating is at a temperature of from 30° C. to 40° C. In one embodiment the incubating is at a temperature of about 37° C.

In one embodiment the second polypeptide has at its N-terminus the amino acid sequence GGG (SEQ ID NO: 29), AAA, CGG, CAA, KGG or KAA.

In one embodiment the first polypeptide comprises at its C-terminus the amino acid sequence LPXTG (SEQ ID NO: 01, wherein X can be any amino acid residue) or LPXTA (SEQ ID NO: 41, wherein X can be any amino acid residue). In one embodiment the first polypeptide comprises at its C-terminus the amino acid sequence LPETG (SEQ ID NO: 04) or LPETA (SEQ ID NO: 42).

In one embodiment the first polypeptide and the second polypeptide are independently of each other selected from an antibody variable domain, an antibody heavy chain Fab-fragment, an antibody Fc-region, a tag, a peptide comprising the amino acid sequence LPXTG (SEQ ID NO: 01, wherein X can be any amino acid residue) or LPXTA (SEQ ID NO: 41, wherein X can be any amino acid residue), a linker, and a non-sortase motif moiety.

One aspect as reported herein is the use of a deep eutectic solvent comprising choline chloride and glycerol at a molar ratio of 1:2, and further comprising up to 5% (v/v) aqueous co-solvent as solvent in an enzymatic transamidation reaction catalyzed by a sortase, preferably by a Sortase A.

DETAILED DESCRIPTION OF THE INVENTION

The invention is at least in part based on the finding that deep eutectic solvents can be used to conduct transamidation reactions, especially sortase catalyzed reactions.

The invention is at least in part based on the finding that hardly water soluble substrates can be conjugated by sortase (in low water content) deep eutectic solvents.

I. Definitions

The term "derived from" denotes that the respective amino acid sequence comprises the same amino acid sequence, or contains 1 to 10 amino acid sequence changes, or is a shortened variant or a fused variant of a parent amino acid sequence.

The term "comprising" when used herein expressly includes the term "consisting of".

The term "a glycinyl, an alaninyl, or a cysteinyl compound" denotes a compound that comprises a glycine or an alanine or a cysteine amino acid residue with free alpha amino group, e.g. as $NH_2$ or $NH_{3+}$, and a carboxy group that is in/part of a peptide bond with another moiety at position 1, whereby the moiety can be any amino group containing moiety, such as an isolated amino acid residue, a peptide, a polypeptide, a protein, a small molecule, a dye, or a (synthetic or natural) linker.

In the present specification and claims the numbering of the residues in an immunoglobulin heavy chain Fc-region is that of the EU index of Kabat (Kabat, E. A., et al., Sequences of Proteins of Immunological Interest, 5th ed., Public Health Service, National Institutes of Health, Bethesda, Md. (1991), NIH Publication 91-3242, expressly incorporated herein by reference).

The term "alteration" denotes the mutation, addition, or deletion of one or more amino acid residues in a parent amino acid sequence, e.g. of an antibody or fusion polypeptide comprising at least an FcRn binding portion of an Fc-region, to obtain a variant antibody or fusion polypeptide.

The term "amino acid mutation" denotes a modification in the amino acid sequence of a parent amino acid sequence. Exemplary modifications include amino acid substitutions, insertions, and/or deletions. In one embodiment the amino acid mutation is a substitution. The term "amino acid mutations at the position" denotes the substitution or deletion of the specified residue, or the insertion of at least one amino acid residue adjacent the specified residue. The term "insertion adjacent to a specified residue" denotes the insertion within one to two residues thereof. The insertion may be N-terminal or C-terminal to the specified residue.

The term "amino acid substitution" denotes the replacement of at least one amino acid residue in a predetermined parent amino acid sequence with a different "replacement" amino acid residue. The replacement residue or residues may be a "naturally occurring amino acid residue" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile); leucine (Leu); lysine (Lys); methionine (Met); phenylalanine (Phe); proline (Pro); serine (Ser); threonine (Thr); tryptophan (Trp); tyrosine (Tyr); and valine (Val). In one embodiment the replacement residue is not cysteine. Substitution with one or more non-naturally occurring amino acid residues is also encompassed by the definition of an amino acid substitution herein. A "non-naturally occurring amino acid residue" denotes a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, alpha-amino isobutyric acid and other amino acid residue analogues such as those described in Ellman, et al., Meth. Enzym. 202 (1991) 301-336. To generate such non-naturally occurring amino acid residues, the procedures of Noren, et al. (Science 244 (1989) 182) and/or Ellman, et al. (supra) can be used. Briefly, these procedures involve chemically activating a suppressor tRNA with a non-naturally occurring amino acid residue followed by in vitro transcription and translation of the RNA. Non-naturally occurring amino acids can also be incorporated into peptides via chemical peptide synthesis and subsequent fusion of these peptides with recombinantly produced polypeptides, such as antibodies or antibody fragments.

The term "amino acid insertion" denotes the incorporation of at least one additional amino acid residue into a predetermined parent amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as defined above.

The term "amino acid deletion" denotes the removal of at least one amino acid residue at a predetermined position in an amino acid sequence.

Within this application whenever an amino acid alteration is mentioned it is a deliberated amino acid alteration and not a random amino acid modification.

The term "tag" denotes a sequence of amino acid residues connected to each other via peptide bonds that has specific binding properties. In one embodiment the tag is an affinity or purification tag. In one embodiment the tag is selected from Arg-tag, His-tag, Flag-tag, 3×Flag-tag, Strep-tag, HA-tag, Nano-tag, SBP-tag, c-myc-tag, S-tag, SNUT-Tag, NusA, T7, thioredoxin, calmodulin-binding-peptide, cellulose-binding-domain, chitin-binding-domain, GST-tag, or MBP-tag (see, e.g., Amau, J., et al., Prot. Expr. Purif. 48 (2006) 1-13).

In one embodiment the tag is selected from SEQ ID NO: 07 (RRRRR), or SEQ ID NO: 08 (RRRRRR), or SEQ ID NO: 09 (HHHHHH), or SEQ ID NO: 10 (KDHLIHNVH-KEFHAHAHNK), or SEQ ID NO: 11 (DYKDDDDK), or SEQ ID NO: 12 (DYKDHDGDYKDHDIDYKDDDDK), or SEQ ID NO: 13 (AWRHPQFGG), or SEQ ID NO: 14 (WSHPQFEK), or SEQ ID NO: 15 (MDVEAWLGAR), or SEQ ID NO: 16 (MDVEAWLGARVPLVET), or SEQ ID NO: 17 (MDEKTTGWRGGHVVEGLAGELEQLRAR-LEHHPQGQREP), or SEQ ID NO: 18 (EQKLISEEDL), or SEQ ID NO: 19 (KETAAAKFERQHMDS), or SEQ ID NO: 20 (KRRWKKNFIAVSAANRFKKISSSGAL), or SEQ ID NO: 21 (cellulose binding domain), or SEQ ID NO: 22 (cellulose binding domain), or SEQ ID NO: 23 (TNPGV-SAWQVNTAYTAGQLVTYNGKTYKCLQPHT-SLAGWEP SNVPALWQLQ), or SEQ ID NO: 24 (GST-tag), or SEQ ID NO: 25 (MBP-tag), or SEQ ID NO: 32 (MRGSHHHHHHGS).

An "effective amount" of an agent, e.g., a pharmaceutical formulation, refers to an amount effective, at dosages and for periods of time necessary, to achieve the desired therapeutic or prophylactic result.

The term "individual" or "subject" denotes a mammal. Mammals include, but are not limited to, domesticated animals (e.g. cows, sheep, cats, dogs, and horses), primates (e.g., humans and non-human primates such as monkeys), rabbits, and rodents (e.g., mice, rats, and hamsters). In certain embodiments, the individual or subject is a human.

The term "pharmaceutical formulation" refers to a preparation which is in such a form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "position" denotes the location of an amino acid residue in the amino acid sequence of a polypeptide. Positions may be numbered sequentially, or according to an established format, for example the EU index of Kabat for antibody numbering.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "sortase A enzymatic activity" as used herein denotes a polypeptide that shows transpeptidation activity in a Reporter immobilization assay (i.e. an assay according to Example 6; and as reported in WO 2016/096740 (incorporated herein by reference).

II. Deep Eutectic Solvents

Deep eutectic solvents (DESs) are mixtures comprising polar components (liquids or solids) that when combined have decreased melting temperatures. DESs can be produced by mixing choline chloride (ChCl) with an organic hydrogen donor, e.g. an amine, amide, alcohol, or carboxylic acid (see e.g. Abbott, A. P., et al., J. Am. Chem. Soc. 126 (2004) 9142-9147; ibid. Chem. Commun. (2003) 70-71). The DES comprises anions, cations and neutral components so that a DES has both, ionic and organic solvent properties (Zhang et al., Angew. Chem. Int. Ed. 48 (2009) 3486-3490).

Proteases have shown activity in DES (Zhao, H., et al., J. Mol. Catal. B-Enzym 72 (2011) 163-167). Likewise lipases have shown activity in DES at 50° C. with 1% (v/v) water (Zhao, H., et al., J. Mol. Catal. B-Enzymatic 85-86 (2013) 243-247) or in a solution comprising 0.135 mL 2-propanol, 1.215 mL Tris-HCl buffer (50 mmol L−1, pH 8.0) and 0-1.2 mol L−1 of DES at 37° C. or combining 0.4-0.5 ml oil, 2.1 mL DES, 0.9 mL methanol, and 300 mg enzyme powder without addition of extra water at 50° C. (Huang, Z.-L., et al., J. Chem. Technol. Biotechnol. 89 (2014) 1975-1981) or at 40° C. to 60° C. (U.S. Pat. No. 8,247,198).

Generally DES can be made by simply warming and stirring the components for a certain time, optionally with a successive drying step. For example, DES can be prepared by a thermal treatment of the previously mixed components (see Abbott (2003) supra; Abbott, A. P., et al., ChemPhysChem 7 (2006) 803) or by a freeze-drying procedure (Gutierrez, M. C., et al., Langmuir 25 (2009) 5509; ibid Angew. Chem. Int. Ed. 49 (2010) 2158).

For example, choline chloride is mixed with an H-bond donor (e.g., glycerol) at elevated temperature (e.g. at 80° C.) in the required molar ratio with agitation for half an hour. To remove traces of water drying with phosphor pentoxide can be performed afterwards (e.g. for two weeks at 45° C.).

Also for example, choline chloride and the hydrogen-bond donor (glycerol or ethylene glycol) are mixed at the intended ratio (i.e. 1:2 or 1:3, respectively) and mixed, using e.g. a magnetic stirrer, at 80° C. for 1-2 hours. After a colorless clear liquid had formed the mixture is cooled down to room temperature and dried over phosphor pentoxide in a desiccator (e.g. at room temperature, 2 weeks)

Another exemplary method is reported in U.S. Pat. No. 8,247,198: nitrogen salt (0.05 mol) and hydrogen bond donor (0.1 mol for choline chloride mixtures, 0.075 mol for ethyl ammonium chloride mixtures) were added to a 20-ml vial and heated at 80° C., until a clear, homogenous liquid formed, typically one hour.

According to U.S. Pat. No. 8,247,198 the components within the DES's are surprisingly and significantly 20 to more than 600-fold less reactive for enzymes than expected. It is reported therein a method comprising enzymatic catalysis of a chemical reaction in a solution comprising a deep eutectic solvent. The reaction may be, e.g., transesterification, aminolysis, hydrolysis, perhydrolysis, and/or alcohol dehydrogenase activity. The reaction may be a polymerization reaction. The polymerization reaction may be catalyzed by an enzyme that is, e.g., a member of the group consisting of enzymes that catalyze transesterification, aminolysis, hydrolysis, perhydrolysis, alcohol dehydrogenation, oxidation-reduction, or dehydrogenation. The reaction may produce, e.g., an addition product or a condensation product.

The polymerization reaction may produce, e.g., a polyester or a polyamide. An enzyme that catalyzes the enzyme-catalyzed chemical reaction may be, e.g., a member of the group consisting of transesterase, hydrolase, lipase, amidase, and dehydrogenase (column 2, lines 4 to 19).

Deep eutectic solvents can comprise as first component a strong hydrogen bond donor and as second component a metal salt or a nitrogen salt. Organic or aqueous components as co-solvents can be present too. For example, in one embodiment, the deep eutectic solvent comprises between 10% and 99% (v/v) of deep eutectic solvent and the remainder is a non-deep eutectic solvent. In one embodiment the second component is a halide-containing salt of an amine or metals. In one embodiment the metal is a transition metal. In one embodiment the first component is selected from the group consisting of hydroxyl, amide, amine, aldehyde, and carboxylic acid. In one embodiment the first component is selected from the group consisting of organic acids, urea, thiourea, amide, hydroxyl groups, diols, glycerol, choline chloride, and combinations thereof. In one embodiment the first component is selected from the group comprising choline chloride, ethyl ammonium chloride, choline bromide, glycerol, tetra butyl ammonium chloride, triethyl benzyl ammonium chloride, zinc chloride, and acetylcholine chloride. In one embodiment the second component is selected from the group consisting of acetamide ethylene glycol, glycerol, urea, malonic acid, formamide, arabinose, glucose, and xylose. In one preferred embodiment the deep eutectic solvent comprises as first component choline chloride and as second component glycerol.

The terms "deep eutectic solvent" or "DES", which can be used interchangeably herein, denote mixtures comprising a nitrogen or metal salt and a hydrogen bond donor forming a eutectic point at the specific applied ratio.

In one embodiment the nitrogen salt is selected from compounds with a positively charged nitrogen atom. In one embodiment the nitrogen salt is selected from the group consisting of primary, secondary, tertiary, and quaternary nitrogen components. In one embodiment the nitrogen salt is an ammonium salt or a substituted ammonium compound. In one embodiment the nitrogen salt is a halide-nitrogen salt. In one embodiment the metal salt is a transition metal salt. In one embodiment the metal salt is a halide-metal salt. In one embodiment the hydrogen bond donor is selected from the group consisting of hydroxyl, amide, amine, aldehyde, and carboxylic acid. In one embodiment the hydrogen bond donor is selected from the group consisting of hydrogen halides, organic acids, urea, choline chloride, thiourea, glycerol, diols, and propane diols. Transition metals are the elements from the period table of the chemical elements that have a number of 21 to 30, 39 to 48, 71 to 80, and 103 to 112. Halides are fluoride (F—), chloride (Cl—), bromide (Br—), iodide (I—) and astatide (At—). In one embodiment the components of the DES have a specific ratio based on their used volume. In one embodiment the ratio is from about 1:3 parts to about 3:1 parts of nitrogen or metal salt to strong hydrogen bond donor. When used in an enzymatic reaction also other components will be present in the DES, such as e.g. an enzyme and its substrates. If the enzyme is not used a solid also the buffer in which the enzyme is dissolved will be present in the DES of a reaction mixture. In one embodiment the reaction mixture of the enzymatic reaction comprises at least 95% DES, at least 90% DES, at least 85% DES, at least 80% DES.

Due to the fact that some enzyme are not available in solid form (either conjugated to a solid support or as powder) a DES used in an enzymatic reaction will comprises to a certain percentage a co-solvent, in most cases water or an aqueous buffer. Thus, the DES accounts for at least 95%, at least 90%, at least 85%, or at least 80% of the volume of the enzymatic reaction mixture and the rest is made up of water or an aqueous buffer. In one preferred embodiment the enzymatic reaction mixture comprises at least 90% of DES, more preferably about 95% of DES.

Deep eutectic solvents useful for enzymatic reactions are, e.g., the mixtures of choline chloride and acetamide (ChCl: Acet), choline chloride and ethylene glycol (ChCl:EG), choline chloride and glycerol (ChCl:G), choline chloride and urea (ChCl:U), choline chloride and malonic acid (ChCl:MA), ethyl ammonium chloride and acetamide (EAC:Acet), ethyl ammonium chloride and ethylene glycol (EAC:EG), ethyl ammonium chloride and glycerol (EAC: Gly), choline bromide and glycerol (ChBr:Gly), tetra butyl ammonium chloride and glycerol (Bu4NCl:Gly), triethyl benzyl ammonium chloride and glycerol (Et3BzNCl:Gly), acetylcholine chloride and glycerol (AcChCl:Gly), choline chloride and formamide (ChCl:F), choline chloride and arabinose (ChCl:Ara), choline chloride and glucose (ChCl: Glc) and choline chloride and xylose (ChCl:Xyl).

Many reactions can be performed in DES, e.g. comprising an enzyme and a DES and optionally a co-solvent. The enzyme and its substrates are present in effective concentrations and at ratios useful to make the intended product. An effective concentration does not include concentrations that are not suitable to make the intended product in meaningful quantities and in a reasonable time. In one embodiment the enzyme is used/is present in an amount/concentration of at least about 0.1, at least about 1, at least about 5, at least about 10, or at least about 20 mg enzyme per ml of solvent, i.e. from about 0.1 to about 10 mg/ml. Similarly, the enzymatic substrates are in one embodiment present in a concentration of at least about 1%, at least about 5%, at least about 10%, at least about 20%, or at least about 30% wt substrate/wt of solvent, i.e. from about 1% to about 25%.

III. Enzymatic Conjugation Using Sortase A

A covalent conjugate (i.e. a fusion polypeptide) comprising two in vivo not covalently associated entities can be obtained in vitro by using the enzyme sortase, especially a Sortase A.

Transamidases in general catalyze the formation of a peptide bond (amide bond) between an acyl donor and a nucleophilic acyl acceptor. In order to form a peptide bond the acyl acceptor has to contain a NH2-CH2-moiety. Gram-positive bacteria include the following genera: *Actinomyces, Bacillus, Bifidobacterium, Cellulomonas, Clostridium, Corynebacterium, Micrococcus, Mycobacterium, Nocardia, Staphylococcus, Streptococcus* and *Streptomyces*.

Sortases have been classified into 4 classes, designated A, B, C, and D, based on sequence alignment and phylogenetic analysis of 61 sortases from gram-positive bacterial genomes (Dramsi, S., et al., Res. Microbiol. 156 (2005) 289-297). These classes correspond to the following subfamilies, into which sortases have also been classified by Comfort and Clubb (Comfort, D. and Clubb, R. T., Infect. Immun. 72 (2004) 2710-2722): Class A (Subfamily 1), Class B (Subfamily 2), Class C (Subfamily 3), Class D (Subfamilies 4 and 5). The aforementioned references disclose numerous sortases and recognition motifs (see also Pallen, M. J., et al., Trends Microbiol. 9 (2001) 97-101). With this information a person skilled in the art can assign a sortase to the correct class based on its sequence and/or other characteristics such as those described in Dramsi (supra).

Sortase A (SrtA) is a membrane bound enzyme has transamidase activity. It has been identified and isolated from gram-positive bacteria. In vivo Sortase A attaches proteins covalently to the bacterial cell wall. The specific recognition motif on the SrtA substrate is LPXTG (SEQ ID NO: 1), whereby the enzyme cleaves between the residues threonine and glycine. The recognition motif on the peptidoglycan is a pentaglycine motif (SEQ ID NO: 31). It has been shown that a triglycine (SEQ ID NO: 29) and even a diglycine motif (SEQ ID NO: 28) on the N-terminus is sufficient to support the SrtA reaction (Clancy, K. W., et al., Peptide Science 94 (2010) 385-396). The reaction proceeds through a thioester acyl-enzyme intermediate, which is resolved by the attack of an amine nucleophile from the oligoglycine, covalently linking peptidoglycan to a protein substrate and regenerating SrtA. SrtA can be used to covalently conjugate chemically synthetized peptides to recombinantly expressed proteins.

Many gram-positive bacteria use sortase to covalently anchor a variety of surface proteins including virulence factors to their cell wall (peptidoglycan). Sortases are membrane associated enzymes. The wild-type *Staphylococcus aureus* sortase A (SrtA) is a polypeptide of 206 amino acids with an N-terminal membrane-spanning region. In a first step, sortase A recognizes substrate proteins that contain a LPXTG (SEQ ID NO: 01) amino acid sequence motif and cleaves the amide bond between the Thr and Gly by means of an active-site Cys. This peptide cleaving reaction results in a sortase A-substrate thioester intermediate. In a second step the thioester acyl-enzyme intermediate is resolved by nucleophilic attack of an amino group of an oligoglycine containing second substrate polypeptide (corresponding to the pentaglycine unit (SEQ ID NO: 31) of peptidoglycan in *S. aureus*) leading to a covalently linked cell wall protein and the regeneration of sortase A. In the absence of oligoglycine nucleophiles, the acyl-enzyme intermediate can be hydrolyzed by a water molecule.

Sortase-mediated ligation/conjugation has begun to be applied for a variety of protein engineering and bioconjugation purposes. This technique enables the introduction of natural and synthetic functionalities into LPXTG-tagged (SEQ ID NO: 1) recombinant or chemically synthesized polypeptides. Examples include the covalent attachment of oligoglycine derivatized polymers (e.g. PEG), fluorophores, vitamins (e.g. biotin and folate), lipids, carbohydrates, nucleic acids, synthetic peptides and proteins (e.g. GFP) (see e.g. Tsukiji, S. and Nagamune, T., ChemBioChem 10 (2009) 787-798; Popp, M. W. L. and Ploegh, H. L., Angew. Chem. Int. Ed. Engl. 50 (2011) 5024-5032).

| year/citation | content |
|---|---|
| 1990 Fischetti et al. Mol. Microbiol. 4 (1990) 1603-1605 | LPETG sortase motif (SEQ ID NO: 4) |
| 1999 Mazmanian et al. Science 285 (1999) 760-763 | *Staphylococcus aureus* strain OS2<br>conserved Leu-Pro-X-Thr-Gly (LPXTG) motif (SEQ ID NO: 1)<br>srtA gene specifies a protein of 206 amino acids with a potential<br>NH2-terminal signal peptide/membrane anchor sequence and a<br>presumed active-site cysteine at position 184<br>srtA homologs are present in *Actinomyces naeslundii*, *Bacillus subtilis*, *Enterococcus faecalis*, *Staphylococcus aureus*, *Streptococcus mutans*, *Streptococcus pneumoniae*, and *Streptococcus pyogenes*<br>AF162687 discloses coding sequence (frame 1 reading)<br>MKKWTNRLMT IAGVVLILVA AYLFAKPHID NYLHDKDKDE KIEQYDKNVK<br>EQASKDKKQQ AKPQIPKDKS KVAGYIEIPD ADIKEPVYPG PATPEQLNRG<br>VSFAEENESL DDQNISIAGH TFIDRPNYQF TNLKAAKKGS MVYFKVGNET<br>RKYKMTSIRD VKPTDVGVLD EQKGKDKQLT LITCDDYNEK TGVWEKRKIF<br>VATEVK (SEQ ID NO: 26) |
| 1999 Ton-That et al. Proc. Natl. Acad. Sci. USA 96 (1999) 12424-12429 | *Staphylococcus aureus* strain OS2<br>*Staphylococcus aureus* Sortase A<br>residues 2-25 deleted (N-terminal signal sequence)<br>MW: 22139 Da<br>mutation C184S abolishes catalytic activity<br>sortase homologs from *Streptococcus pyogenes* (Spyo), *Enterococcus faecalis* (Efea), *Actinomyces naeslundii* (Anei), *Streptococcus mutans* (Smut), *Bacillus subtilis* (Bsub), and *Streptococcus pneumoniae* (SpnA, SpnB, and SpnC)<br>water can resolve acyl-enzyme intermediate |
| 2000 Dhar et al. Biochem. 39 (2000) 3725-3733 | *Listeria monocytogenes* has a peptidoglycan cross-bridge (m-Dpm) which is chemically distinct and much shorter than the pentaglycine (SEQ ID NO: 31) cross-bridge of *staphylococci*<br>*Listeria monocytogenes* Sortase A has the same sortase motif as *Staphylococcus aureus* Sortase A: LPXTG (SEQ ID NO: 1) (LPTTG (SEQ ID NO: 47)) |
| 2000 Ton-That et al. J. Biol. Chem. 275 (2000) 9876-9881 | purified recombinant *Staphylococcus aureus* Sortase A<br>hydrolyzes peptides with LPXTG motif (SEQ ID NO: 1)<br>triple G-motif (SEQ ID NO: 29)<br>in presence of H2N-GGG (SEQ ID NO: 29) exclusive transpeptidation<br>in the presence of amino-donors sortase mediated LPXTG motif (SEQ ID NO: 1) cleavage rate was increased<br>Sortase is a 206-amino acid polypeptide with an N-terminal signal |

| year/citation | content |
|---|---|
| | sequence/stop transfer domain, is anchored in the cytoplasmic membrane of *staphylococci*<br>residues 1-25 correspond to N-terminal signal sequence<br>reaction conditions: |
| | 5 mM amino group nucleophile<br>4.71 µM SrtADN<br>150 mM NaCl, 5 mM CaCl2, 50 mM Tris-HCl, pH 7.5)<br>volume of 520 µl<br>reaction conditions: |
| | 10 µM fluorescent peptide<br>5 mM amino group nucleophile H2N-GGG (SEQ ID NO: 29)<br>15 µM SrtADN<br>150 mM NaCl, 5 mM CaCl2, 50 mM Tris-HCl, pH 7.5)<br>volume of 520 µl<br>37° C., 16 h |

TABLE III
Kinetic analysis of $SrtA_{\Delta N}$
Kinetic constants $K_m$, $V_{max}$, and $k_{cat}$ were calculated from the curve fit for the Michaelis-Menten equation using the Lineweaver-Burk plot. Reaction conditions are described in the legend to FIG. 4.

| Nucleophile | $K_m$ µM | $V_{max}$ µM/s | $K_{cat}$ 1/s | $K_m/K_{cat}$ 1/µM · s |
|---|---|---|---|---|
| H$_2$O | 10.88 | $5.08 \times 10^{-5}$ | $1.06 \times 10^{-5}$ | $9.77 \times 10^{-7}$ |
| NH$_2$-Gly$_3$ (SEQ ID NO: 29) | 16.48 | $1.08 \times 10^{-4}$ | $2.27 \times 10^{-5}$ | $1.38 \times 10^{-6}$ |

TABLE IV
The effect of different nucleophiles on the rate of LPXTG (SEQ ID NO: 1) peptide cleavage by sortase ($SrtA_{\Delta N}$)

| Nucleophile | M $(S^{-1})^a$ |
|---|---|
| H$_2$O | 1.84 (±0.11) |
| NH$_2$OH | 1.91 (±0.07) |
| NH$_2$-Gly | 1.95 (±0.05) |
| NH$_2$-Gly$_2$ (SEQ ID NO: 28) | 2.03 (±0.13) |
| NH$_2$-Gly$_3$ (SEQ ID NO: 29) | 2.91 (±0.03) |

$^a$Slope of the kinetic curves as shown in FIG. 4. The substrate peptide d-QALPETGEE-e (SEQ ID NO: 48) was incubated with $SrtA_{\Delta N}$ and various nucleophiles. Substrate cleavage between the threonine and the glycine was measured as an increase in fluorescence. With the exception of water, all nucleophiles were added at a concentration of 5 mM. Averages were calculated from three independent experiments and standard deviations are reported (parentheses).

| year/citation | content |
|---|---|
| 2001 Bolken et al. Infect. Immun. 69 (2001) 75-80 | sortase A from *Streptococcus gordonii*<br>252 amino acid residues with N-terminal signal sequence<br>cysteine at position 210<br>12-amino-acid extension at the carboxy-terminus of the *S. gordonii* protein compared to *S. aureus* |
| 2001 Glaser et al. Science 294 (2001) 849-852 | *Listeria monocytogenes* genome contains 41 proteins containing an LPXTG (SEQ ID NO: 1)<br>Lm genome contains more LPXTG (SEQ ID NO: 1) proteins than any other gram-positive bacterium (*Strep. pyogenes*: 13; *St.au. aureus*: 18) |
| 2001 Ilangovan et al. Proc. Natl. Acad. Sci. USA 98 (2001) 6056-6061 | NMR structure of *St.au. aureus* Sortase A<br>unique b-barrel structure including two short helices and several loops<br>the active-site sulfhydryl of cysteine-184 is poised for ionization by histidine-120, presumably enabling the resultant thiolate to attack the LPXTG peptide (SEQ ID NO: 1)<br>conservation of H120 and C184<br>calcium binding near the active site stimulates catalysis<br>stimulation by about 2 mM calcium ions<br>magnesium and manganese ions can substitute for calcium ions<br>sortase with residues 1-29 deleted<br>sortase with residues 1-59 deleted<br>average mass of 16,595.12 Da observed |

| year/citation | content |
|---|---|
| | reaction conditions:<br>2 mM H2N-GGG (SEQ ID NO: 29)<br>5 µM sortase N-terminal deletion variant<br>150 mM NaCl, 5 mM CaCl2, 50 mM Tris*HCl pH 7.5<br>reaction volume 520 µL |
| 2001 Mazmanian et al. Mol. Microbiol. 40 (2001) 1049-1057 | *S. aureus* SrtA residues 26-59 display no amino acid conservation; core SrtA residues 60-206 present in all sortase homologs examined<br>*St. aureus* sorting motifs: LPETG (SEQ ID NO: 4), LPDTG (SEQ ID NO: 49), LPKTG (SEQ ID NO: 43), LPNTG (SEQ ID NO: 50), PLAAG (SEQ ID NO: 51), LPKAG (SEQ ID NO: 52), LPQTG (SEQ ID NO: 53)<br>*Actinomyces naeslundii, Bacillus anthracis, Bacillus subtilis, Clostridium acetabutylicum, Corynebacterium diphtheria, Enterococcus faecalis, Listeria monocytogenes, Streptococcus mutans, Streptococcus pneumoniae, Streptococcus pyogenes* |
| 2001 Pallen et al. TRENDS Microbiol. 9 (2001) 97-101 | LPXTG (SEQ ID NO: 1) like motif, followed shortly by a membrane-spanning hydrophobic domain and a charged carboxy-terminal tail |
| | SC7A8.19     VAGHVDNA--------EGPAVFYRLGALEKGSAIEIDRRDGGV-AVFTVDAVEVYAADAFPDEKVYGAAD---------RPELRVITCGGPYSR-----STGYQGNVV (SEQ ID NO: 54) |
| | SCM10.23     VVGHVDNQ--------QGPAVFYGLGALKKGNKVEVHRQDGKT-AVFEIYGIEVFEKNNFPGDRVYGSKG---------SPELRVITCGGGFTK-----QNGYDGNVV (SEQ ID NO: 55) |
| | SC5C11.07     IAGHVDTK--------TSAAVFARLDQLDKGDKFQVRRADGRS-ATFVVDGLETFAKDEFPSDRVYGDAD---------RPEVRLITCAGDYDH----KVKDYTDNLV (SEQ ID NO: 56) |
| | SCE20.15c     MVGHVDTE-------TRPAVFYQLSTLEPGQTIRVARDDDEV-AEFTVDDVQVLTRDGFDAQQAYGPRDTG-------RSELRLITCGGTFDQ----TTDSYTANVV (SEQ ID NO: 57) |
| | BH3596_bachd     LSGHRDT-------------VFRDMGKLEIGDDLTVHMPYGS--YTYRIVDTEIVDAN----DTSVIRSTAP-------DEVLTLSTCYPFNF----IGSAPERYIIY (SEQ ID NO: 58) |
| | yhcs_bacsu     LSGHRDT-------------VFRRTGELEKGDQLRLLLSYGE--FTYEIVKTKIVDKD----DTSIITLQHE-------KEELILTTCYPFSY----VGNAPKRYIIY (SEQ ID NO: 59) |
| | BH4010_bachd     LSGHRDT-------------VFRELGEVGVGDLLIVETATGT--HTYRVRKVRIVDED----DRTVIVPKP--------RATLTVSTCYPFDF----IGSAPERYILE (SEQ ID NO: 60) |
| | slp2_bacan     LSGHRDT-------------VFTDLGQLKEKDTLVLEYDNKT--YTYEIQKIWITHAD----DRTVIIKKE--------EPILTLTTCYPFDY----IGDAPDRYIIE (SEQ ID NO: 61) |
| | BH2127_bachd     IAAHRSR---------TYGRQFNRLDEVEVGDVITVTTNNHM--YRYTVYSITVVEPT----NIDILQHDG-------TAPVLTLITCDPVKDP----THRLIVQAEM (SEQ ID NO: 62) |
| | slp_cloab     LAGHRSY---------TFGEYFNRLGEIGSGDEIDVETVNGT--FKYKVYSTKVVLPS----EVHVLDQT--------KDPTMTLVTCTPIRIA----THRLIIKAKR (SEQ ID NO: 63) |
| | SCH69.20c     LAGHRN----------THGEPFRYINKLEPGDPIVVETQDKY--FVYKMASILPVTSPS---NVSVLDPVPKQSGFKGPGRYITLTTCTPEFTS----KYRMIVWGKM (SEQ ID NO: 64) |
| | SCH69.19c     LAAHRD----------GHGARFHNIDKIEKGDPIVFETKDTW--YVYKTYAVLPETSKY---NVEVLGGIPKESGKKKAGHYITLTTCTPVYTS----RYRYVVWGEL (SEQ ID NO: 65) |
| | fap2_actna     ITGHRGL---------AEATMFTNLDKVKTGDSLIVEVFGEV--LTYRVTSTKVVEPE----ETEALRVEE-------GKDLLTLVTCTPLGIN----THRILLTGER (SEQ ID NO: 66) |

-continued

| year/citation | content | |
|---|---|---|
| | slp4_cordi | ITAHRGL---------AEATMFTNLNKVGVGDRFTIEVMGEV--LTYEVRETRVVSPE----DTRFLQTQD-------DRDLVTLVTCTPLGIN----THRILVTAER (SEQ ID NO: 67) |
| | slp2_strpn | ITAHTGL---------PTAKMFTDLTKLKVGDKFYVHNIKEV--MAYQVDQVKVIEPT----NFDDLLIVP-------GHDYVTLLTCTPYMIN----THRLLVRGHR (SEQ ID NO: 68) |
| | slp4_strpn | ITAHRGL---------PTAELFSQLDKMKKGDIFYLHVLDQV--LAYQVDQIVTVEPN----DFEPVLIQH-------GEDYATLLTCTPYMIN----SHRLLVRGKR (SEQ ID NO: 69) |
| | slp2_enfae | ISGHRGL---------PQAKLFTDLPELKKGDEFYIEVNGKT--LAYQVDQIKTVEPT----DTKDLHIES-------GQDLVTLLTCTPYMIN----SHRLLVRGHR (SEQ ID NO: 70) |
| | slp_streq | ISGHRGL---------PSAKLFTNIDKLRINDTFTITSLNRT--MTYQVDKIATVLPD----DVSLLRIEE-------GKDLVTLVTCTPYGVN----THRLLVRGHR (SEQ ID NO: 71) |
| | slp2_strpy | ISAHRGL---------PSAEMFTNLNLVKKGDTFYFRVLNKV--LAYKVDQILTVEPD----QVTSLSGVM-------GKDYATLVTCTPYGVN----TKRLLVRGHR (SEQ ID NO: 72) |
| | slp1_cordi | ITGHSGL---------ANATLFDNLEDVKEHDPIYITVQGET--LKYEVDAINVVLPE----DTKLLAPDP-------NKDQITLITCTPYAVN----SHRLLVRAHR (SEQ ID NO: 73) |
| | slp2_cordi | ITGHTGL---------ANSTMFDHLNKAEKGDTFYVQVSGEK--LKYVVDQIKVVLPT----ETEDLRPEQ-------GKDYITLITCTPYGIN----THRLMVRGHQ (SEQ ID NO: 74) |
| | slp3_cordi | LSAHTGL---------QNATLWDNLIQIKKGDPVYVAAAGEK--LKYEVRNIEVVTPD----KTSLLRRTS-------NKDQVTLITCTPYGIN----THRLIITAER (SEQ ID NO: 75) |
| | slp5_cordi | LTAHSGI---------QKSTFFDNLEKVKKGDAIYVRNIGET--LKYQVRDIEIIRPA----EIDRIQPIP-------DRDLITLVTCTPYGIN----THRLVTAER (SEQ ID NO: 76) |
| | BH2015_bachd | IAGHRGYRGNR---------HFSRLPDVTIGDEVFLHTKEET--FVYKVTDISIIEPT----DVDVLDDRD-------GKHEITMITCTRSGK------QRVAVRGEL (SEQ ID NO: 77) |
| | BH0362_bachd | IAGHRGYRGNR---------HFSRLPDVTIGDEVFLHTKEET--FVYKVTDISIIEPT----DVDILDDRD-------GKHEITMITCTRSGK------QRVAVRGVL (SEQ ID NO: 78) |
| | slp_strmu | LASHHVFGMTG-----SSQMLFSPLERAKEGMEIYLTDKNV--YTYVISEVKTVTPE----HVEVIDNRP-------GQNEVTLVTCTDAGAT----ARTIVHGTYK (SEQ ID NO: 79) |
| | slp1_strpy | LASHHIFGITG-----SSQMLFSPLERAQNGMSIYLTDKEKI--YEYIIKDVFTVAPE----RVDVIDDTA-------GLKEVTLVTCTDIEAT----ERIIVKGELK (SEQ ID NO: 80) |
| | slp1_strpn | LASHHIFGVDN-----ANKMLFSPLDNAKNGMKIYLTDKNKV--YTYEIREVKRVTPD----RVDEVDDRD-------GVNEITLVTCEDLAAT----ERIIVKGDLK (SEQ ID NO: 81) |
| | slp1_enfae | LASHRTEDGVS---------LFSPLERTKKDELIYITDLSTV--YTYKITSVEKIEPT----RVELIDDVP-------GQNMITLITCGDLQAT----TRIAVQGTLA (SEQ ID NO: 82) |
| | BH3294_bachd | VDHHEGFYYDT-LYNRYDVEVFSAYVTTT--DFYYIETEFPS-KDDYKAFLNELKKRSV---VQTNVEVGE-------EDQIITLSTCDYRLRD---RGRLVVHGKL (SEQ ID NO: 83) |
| | slp3_bacan | FMSHRKLYYDT-LFEGYDLEVFSVYTTTT--DFYYIETDFSS-DTEYTSFLEKIQEEKSL---YKTDTTVTA-------GDQIVTLSTCDYALDPE---AGRLVVHAKL (SEQ ID NO: 84) |
| | slp_staau | YEKHKIIEFDN-KYGKYQLQVFSAYKTTT--KDNYIRTDFEN-DQDYQQFLDETKRKSV---INSDVNVTV-------KDKIMTLSTCEDAYSET---TKRIVVVAKI (SEQ ID NO: 85) |

| year/ citation | content | |
|---|---|---|
| | slp3_strpy | FNKHKEFSIETKTKQKLKINIFACIQTDAFDSLLFN PIDVDI--SSKNEFLNHIKQKSV---QYREILTTN------ -ESRFVALSTCEDMTT-----DGRIIVIGQI (SEQ ID NO: 86) |
| | slp4_strpy | FNKHNKAIIETKERKKLTVTIFACLKTDAFDQLVF NPNAITN--QDQQKQLVDYISKRSK-- QFKPVKLKH-------HTKFVAFSTCENFST----- DNRVIVVGTI (SEQ ID NO: 87) |
| | slp3_strpn | IAGHRAE--------- PSHVFFRHLDQLKVGDALYYDNGQEI-- VEYQMMDTEIILPS----EWEKLESVS------- SKNIMTLITCDPIPTFN----KRLLVNFER (SEQ ID NO: 88) |
| | slp1_bacan | LAGHNMS--------- KKGVLFSDIASLKKGDKIYLYDNENE-- YEYAVTGVSEVTPD----KWEVVEDHG--------- KDEITLITCVSVKDN----SKRYVVAGDL (SEQ ID NO: 89) |
| | ywpe_bacsu | LAGHHLK--------- QKNLLFGPLENIKTGAQIVITDFKKD-- YIYSVTSKDIISEM----DADVVEETN--------- KKEITLITCDKAVKT----EGRLVVKGEL (SEQ ID NO: 90) |
| | slp3_enfae | LASHNAG--------- YEGLLFTSLNKVSVGDLVKLNDREGHS- FIYKVKEQKHVDMT----DTTMLNLTR--------- KPTLTLITCDQATKT----TGRIIVIAEL (SEQ ID NO: 91) |
| | sortase_staau | IAGHTFID-------- RPNYQFTNLKAAKKGSMVYFKVGNET-- RKYKMTSIRDVKPT----DVGVLDEQKG------ KDKQLTLITCDDYNEK----TGVWEKRKIF (SEQ ID NO: 92) |
| | slp_shepu | IAGHRDT------------- HFAILKGMTVGRRLALQTAAGKE- IVYQVVATKVVHES----QTELMAPSD--------- DNRLTLITCYPFDALQGVAELRFVVQAVP (SEQ ID NO: 93) |
| | SCH22A.15c | VLGHVTVG--------RYDGVFRHLAGRR- GERIEARENGT---TAEFTTAVRTVAKDF--- PTDDVYGVA---------PELRLITCGPRDGQE--- YRDNVIVAEL (SEQ ID NO: 94) |
| | slp_clodi | IYGHNMKN---- KTMFNNLNKFKDADFFKKNNKIKITLNGKE-- FLYDVFSAYIVESDYDYLKTNFNNESD------- YQNYINDITSKSLYKSP----IKVNSNDKI (SEQ ID NO: 95) |
| | MTH1829_metth | ILGHRTT---------- YSGPFRKIGALRKGDRVIIEDASSSIRYIYTVTSNG DDIRWDY--RTNPVRFSQS------ GDARLMLITCYPPGQK----KAAWITHCKL (SEQ ID NO: 96) |
| | *St.au. aureus*: LPKTG (SEQ ID NO: 43) *St.au. pyogenes*: LPITG (SEQ ID NO: 97) *Bac. anthracis*: LPKTG (SEQ ID NO: 43) *Bac. subtilis*: LPDTA (SEQ ID NO: 98) *Clos. difficile*: SPKTG (SEQ ID NO: 99) *Clos. acetabutylicum*: LPKTG (SEQ ID NO: 43) *S. coelicolor*: LAETG (SEQ ID NO: 100), LAATG (SEQ ID NO: 101), LAHTG (SEQ ID NO: 102), LASTG (SEQ ID NO: 103) *Arthrobacter. sp.*: LASTG (SEQ ID NO: 103) *A. naeslundii*: LPLTG (SEQ ID NO: 104) *A. viscosus*: LPLTG (SEQ ID NO: 104), LSRTG (SEQ ID NO: 105) *S. pneumoniae*: LPETG (SEQ ID NO: 4), VPDTG (SEQ ID NO: 106), IPQTG (SEQ ID NO: 107), YPRTG (SEQ ID NO: 108) *C. diphtheria*: LPMTG (SEQ ID NO: 109), LALTG (SEQ ID NO: 110), LPKTG (SEQ ID NO: 43), LGNTG (SEQ ID NO: 111), LPLTG (SEQ ID NO: 104), LAFTG (SEQ ID NO: 112) *S. putrefasciens*: LPQTS (SEQ ID NO: 113) | |
| 2002 Garandeau et al. Infect. Immun. 70 (2002) 1382-1390 | in silico identification of sortase from *L. monocytogenes* 222 amino acid residues TLXTC (SEQ ID NO: 114) consensus motif for sortase active site MLKKTIAAAA LAAGLLLIFS PFIKNGIVKY MSGHETIEQY KASDIKKNNE KDATFDFESV QLPSMTSVIK GAANYDKDAV VGSIAVPSVD VNLLVFKGTN TANLLAGATT MRSDQVMGKG NYPLAGHHMR DESMLFGPIM KVKKGDKIYL TDLENLYEYT VTETKTIDET EVSVIDNTKD ARITLITCDK PTETTKRFVA VGELEKTEKL TKELENKYFP SK (SEQ ID NO: 27) | |
| 2002 Bierne et al. Mol. Microbiol. 43 (2002) 869-881 | *Listeria monocytogenes* BLAST analysis: one sequence that is 28% identical to *S. aureus* SrtA and encodes a protein of 222 amino acids with an expected molecular weight of 24.7 kDa contains a putative signal peptide/transmembrane region, the expected TLXTC sequence (SEQ ID NO: 114) and two stretches of 13 and 31 amino acids that are not present in SrtA | |
| 2004 | peptide with single aminoglycoside as nucleophile | |

| year/ citation | content |
| --- | --- |
| Mao et al. J. Am. Chem. Soc. 126 (2004) 2670-2671 | attack 50 times faster than water<br>yield not affected by number of glycine residues<br>30% yield after 30 min, 50% after 6 h, 90% after 24 h<br>conjugates D-amino acid containing peptide; rate half that for L-amino acid peptides<br>conjugation of small molecules coupled to triglycine (SEQ ID NO: 29) (folate)<br>branched peptide as efficiently coupled as linear peptide |
| 2004 Kruger et al. Biochem. 43 (2004) 1541-1551 | SrtA in Staphylococcus aureus, Streptococcus gordonii, Listeria monocytogenes, Streptomyces coelicolor, Streptococcus pyogenes, Streptococcus suis<br>S. aureus two sortase isoforms: SrtA, SrtB (MPQTN motif (SEQ ID NO: 115))<br>LPXTG motif (SEQ ID NO: 1) highly conserved among all gram-positive bacteria<br>NPQTN motif (SEQ ID NO: 116) appears to be conserved only among at least three bacteria containing the heme iron acquisition isd gene locus (Bacillus anthracis, Bacillus halodurans, and S. aureus)<br>Staphylococcus aureus Sortase A<br>residues 2-24 deleted<br>transpeptidase reaction conditions: |
| | 100 μL reaction volume<br>150 mM NaCl, 300 mM Tris, 5 mM CaCl2 (pH 7.5),<br>pentaglycine (SEQ ID NO: 31) (2 mM), SrtAΔN24 (840 nM),<br>and 0 to 10 mM Abz-LPETG-Dap(Dnp)-NH2 (SEQ ID NO: 117)<br>37° C., 30 min<br>transpeptidase reaction conditions: |
| | 100 μL reaction volume<br>150 mM NaCl, 300 mM Tris, 5 mM CaCl2 (pH 7.5)<br>SrtAΔN24 (15 μM), Gly5 (SEQ ID NO: 31) (2 mM), peptide (300 μM)<br>37° C. for 30 min<br>quenched by 1N HCl (50 μL)<br>transpeptidase reaction conditions: |
| | 100 μL reaction volume<br>150 mM NaCl, 300 mM Tris, 5 mM CaCl2 (pH 7.5)<br>SrtAΔN24 (60 μM), Gly5 (SEQ ID NO: 31) (2 mM), peptide (300 μM)<br>37° C. for 360 min<br>no reaction with inverted sortase motif or SrtB motif<br>initial velocity motif: LPXTG (X = any except P, C; X = M fastest (SEQ ID NO: 118))<br>end point motif: L/M-P-X-A/L/S/T/V-G (X = any except P, C; L better than M; T and A comparable, then S and V and L comparable) (SEQ ID NO: 119)<br>Table 3 sorting signals: LM: IPKTG (SEQ ID NO: 120), IPALG (SEQ ID NO: 121), LAASS (SEQ ID NO: 122), LPATG (SEQ ID NO: 123), LPKAG (SEQ ID NO: 52), LPISS (SEQ ID NO: 124), IPALG (SEQ ID NO: 121), LPKTS (SEQ ID NO: 125) |
| 2007 Parthasarathy et al. Bioconjug. Chem. 18 (2007) | conjugation to surface of non-protein species (polystyrene beads, PEG)<br>alkylamine as nucleophile<br>making of cyclic peptides<br>use of 159 amino acid sortase<br>transpeptidase reaction conditions: |
| 469-476 | 50 mM Tris, 150 mM NaCl, pH 8, 0.1% Tween-20, 6 mM CaCl2, 3 mM beta-mercaptoethanol<br>37° C., 3 h<br>15 μM eGFP, 10 μM sortase<br>add 10 mM EDTA to stop the reaction |

-continued

| year/citation | content |
|---|---|
| 2007<br>Chan et al.<br>PlosOne<br>11 (2007)<br>e1164 | transpeptidase reaction conditions:<br>50 mM Tris, 150 mM NaCl, pH 8<br>37° C., 3 h<br>12 µM eGFP-LPETG (SEQ ID NO: 4), 40 µM sortase, 36 µM<br>GGG-eGFP (SEQ ID NO: 29)<br>with beads higher concentration of sortase has to be used for<br>comparable yield<br>use of a cleavable upstream tag to protect nucleophile (GGG (SEQ<br>ID NO: 29))<br>enzyme displays a strong preference for glycine in the first position;<br>alanine and valine can apparently substitute for glycine in the second<br>position, although the reaction is not as efficient<br>conjugation to solid supports<br>tetraglycine (SEQ ID NO: 30) beads react faster than diglycine<br>(SEQ ID NO: 28) beads which react faster than monoglycine beads<br>reaction conditions:<br>85 µM eGFP-LPETGG-His6 (SEQ ID NO: 126)<br>40 nM His6-sortase (SEQ ID NO: 9)<br>50 mM Tris-HCl, 150 mM NaCl, 5 mM CaCl2, pH 7.5<br>sortase amplified for *S. aureus* genome<br>N-terminal membrane targeting sequence removed<br>30 kDa on SDS gel |
| 2008<br>Samantaray<br>et al.<br>J. Am.<br>Chem.<br>Soc. 130<br>(2008)<br>2132-2133 | peptide-sugar conjugation<br>6-aminohexoses<br>peptide antibiotic ligation (aminoglycosides)<br>conjugates between antibiotics and peptides with yields of 35 to<br>70% for kanamycin class, about 18-30% for ribostamycin class<br>YALPET-sugar adduct (SEQ ID NO: 127)<br>YALPMTGK- sugar adduct (SEQ ID NO: 128)<br>LPNTG motif (SEQ ID NO: 50) with *S. aureus* sortase and peptide |

For the enzymatic conjugation a soluble truncated sortase A lacking the membrane-spanning region (SrtA; amino acid residues 60-206 of *Staphylococcus aureus* SrtA) can be used (SEQ ID NO: 05; see also Ton-That, H., et al., Proc. Natl. Acad. Sci. USA 96 (1999) 12424-12429; Ilangovan, H., et al., Proc. Natl. Acad. Sci. USA 98 (2001) 6056-6061).

The sortase A-mediated reaction results in the ligation of species containing a sortase motif (sequence) with those bearing one or more N-terminal glycine residues. The sortase motif can be the amino acid sequence LPXTG (SEQ ID NO: 1), but can also different therefrom (see below). However, a drawback of using such sequences as acyl donors is that the transfer of the LPXT unit (SEQ ID NO: 129) to a nucleophilic acyl acceptor liberates a stoichiometric amount of a corresponding fragment containing at least one N-terminal glycine residue. The liberated glycine-containing fragment competes with the intended acyl acceptor for the enzymatic intermediate and works against the progress of the enzymatic ligation reaction. Additionally the hydrolytic cleavage of the enzymatic intermediate as well as the LPXTG (SEQ ID NO: 1) containing substrate, although a relatively slow process, compete with the reaction. In the beginning of the use of the sortase-mediated reaction useful levels of ligation could only be obtained using concentrations of at least 5 mM of the acyl donor comprising the sortase-motif.

The general sortase-motif has the amino acid sequence LPXT (SEQ ID NO: 129), wherein X can be any amino acid residue, i.e. a naturally occurring amino acid residue or a non-naturally occurring amino acid residue. In some embodiments, X is selected from the group of amino acid residues comprising or consisting of (in one letter code) D, E, A, N, Q, K, and R. In some embodiments, the sortase-motif is selected from the group comprising or consisting of the amino acid sequences LPXT (SEQ ID NO: 129), LPXA (SEQ ID NO: 130), SPXT (SEQ ID NO: 131), LAXT (SEQ ID NO: 132), LSXT (SEQ ID NO: 133), NPXT (SEQ ID NO: 134), VPXT (SEQ ID NO: 135), IPXT (SEQ ID NO: 136), LGXT (SEQ ID NO: 137), and YPXR (SEQ ID NO: 138). In some embodiments, the sortase motif is selected from the group of amino acid sequences consisting of LPST (SEQ ID NO: 139), LPKT (SEQ ID NO: 140), LPIT (SEQ ID NO: 141), LPDT (SEQ ID NO: 142), SPKT (SEQ ID NO: 143), LAET (SEQ ID NO: 144), LAAT (SEQ ID NO: 145), LAET (SEQ ID NO: 144), LAST (SEQ ID NO: 146), LAET (SEQ ID NO: 144), LPLT (SEQ ID NO: 147), LSRT (SEQ ID NO: 148), LPET (SEQ ID NO: 149), VPDT (SEQ ID NO: 150), IPQT (SEQ ID NO: 151), YPRR (SEQ ID NO: 152), LPMT (SEQ ID NO: 153), LPLT (SEQ ID NO: 147), LAFT (SEQ ID NO: 154), and LPQT (SEQ ID NO: 155). In certain embodiments in which sortase A is used, the sortase-motif comprises the amino acid sequence X1PX2X3 (SEQ ID NO: 156), wherein i) X1 is selected from the group consisting of the amino acid residues leucine, isoleucine, valine and methionine, ii) X2 is any amino acid, and iii) X3 is selected from the group consisting of threonine, serine and alanine. In specific embodiments, as noted above X1, is leucine and X3 is threonine. In certain embodiments X2 is selected from the group consisting of aspartate, glutamate, alanine, glutamine, lysine and methionine.

In some embodiments the sortase-motif is selected from the group of amino acid sequences comprising or consisting of LPKTG (SEQ ID NO: 43), LPITG (SEQ ID NO: 97), LPDTA (SEQ ID NO: 98), SPKTG (SEQ ID NO: 99), LAETG (SEQ ID NO: 100), LAATG (SEQ ID NO: 101), LAHTG (SEQ ID NO: 102), LASTG (SEQ ID NO: 103), LAETG (SEQ ID NO: 100), LPLTG (SEQ ID NO: 104), LSRTG (SEQ ID NO: 105), LPETG (SEQ ID NO: 4), VPDTG (SEQ ID NO: 106), IPQTG (SEQ ID NO: 107), YPRRG (SEQ ID NO: 157), LPMTG (SEQ ID NO: 109), LPLTG (SEQ ID NO: 104), LAFTG (SEQ ID NO: 112), and LPQTS (SEQ ID NO: 113). In some embodiments of the invention the sortase is a sortase A (SrtA). SrtA recognizes a sortase-motif with the amino acid sequence LPXTG (SEQ ID NO: 1). Common sortase-motif amino acid sequences are, e.g., LPKTG (SEQ ID NO: 43), LPATG (SEQ ID NO: 123), LPETG (SEQ ID NO: 4) and LPNTG (SEQ ID NO: 50). In some embodiments LPETG (SEQ ID NO: 4) is used. However, sortase-motifs not in line with this consensus sortase-motif amino acid sequence may also be recognized. For example, in some embodiments the sortase-motif comprises the amino acid residue A rather than the amino acid residue T at position 4, e.g. LPXAG (SEQ ID NO: 158) or LPNAG (SEQ ID NO: 159). In some embodiments the sortase-motif comprises the amino acid residue A rather than the amino acid residue G at position 5, e.g. LPXTA (SEQ ID NO: 41) or LPNTA (SEQ ID NO: 160). In some embodiments the sortase-motif comprises the amino acid residue G rather than the amino acid residue P at position 2, e.g. LGXTG (SEQ ID NO: 161) or LGATG (SEQ ID NO: 162). In some embodiments the sortase-motif comprises the amino acid residue I rather than the amino acid residue L at position 1, e.g., IPXTG (SEQ ID NO: 163) or IPNTG (SEQ ID NO: 164) or IPETG (SEQ ID NO: 165).

In some embodiments, where the sortase-motif is LPXTG (SEQ ID NO: 166) or LPXT (SEQ ID NO: 167), X is selected from the group consisting of D, E, A, N, Q, K, and R. In some embodiments X is selected from the group of amino acid residues consisting of K, E, N, Q, and A in an LPXTG (SEQ ID NO: 168) or LPXT (SEQ ID NO: 169) motif where the sortase is a sortase A. In one embodiment the sortase-motif is LPET (SEQ ID NO: 149) or LPETG (SEQ ID NO: 4) or LPETA (SEQ ID NO: 42).

In certain embodiments where sortase A from *Staphylococcus aureus* (St.au. SrtA) is used the sortase-motif has the amino acid sequence LPX1TX2 (SEQ ID NO: 170), wherein i) X1 is selected from the group of amino acid residues consisting of D, E, A, N, Q, K, and R, and ii) X2 is selected from the group of amino acid residues consisting of alanine and glycine. In certain embodiments the sortase-motif of St.au. SrtA is LPX1TA (SEQ ID NO: 171). In other embodiments the sortase-motif of St.au. SrtA is LPX1TG (SEQ ID NO: 166). X1 has the meaning as outlined before.

*Streptococcus pyogenes* sortase A (St.py. SrtA) will accept di-alanine based nucleophiles. This sortase will efficiently cleave the sortase-motif amino acid sequence LPXTA (SEQ ID NO: 41) between the threonine and the alanine residue and install modified alanine-based nucleophiles. St.py. SrtA will also recognize and cleave LPXTG motifs (SEQ ID NO: 1), albeit with reduced efficiency.

*Staphylococcus aureus* sortase A (St.au. SrtA) will not significantly cleave LPXTA motifs (SEQ ID NO: 41) or accept alanine based nucleophiles.

In one embodiment, a polypeptide is contacted with Strep. SrtA and an alanine-containing nucleophile. The polypeptide comprises a sortase-motif amino acid sequence that can be recognized by Strep. SrtA at or near its C-terminus and the nucleophile comprises one or more amino acids capable of serving as nucleophile for a St.au. SrtA-mediated reaction at or near its N-terminus (e.g., (G)n, where n is between 1 and 10, e.g., between 1 and 5 (SEQ ID NO: 172)). This leads to the formation of an LPXTA sequence (SEQ ID NO: 41) at the reactive site, a motif refractory to cleavage by St.au. SrtA. This allows for example St.au. SrtA to act on the N-terminus without affecting the C-terminal modification installed with Strep. SrtA.

Sortase fragments having sortase transamidation activity can be used in the methods as reported herein. Sortase fragments can be identified by producing fragments of sortase, for example, by recombinant techniques or proteolytic digestion of full length sortase, and determining the rate of peptide bond formation, i.e. ligation. The fragment can comprise about 80% of amino acid sequence of full-length sortase, about 70%, about 60%, about 50%, about 40% or about 30% of the amino acid sequence of full-length sortase such as that of *S. aureus* Sortase A (GenBank Accession number AAD48437). In some embodiments the fragment lacks an N-terminal portion of the full-length sortase amino acid sequence that is not essential to the catalytic activity of sortase, for example the fragment lacks the N-terminal portion extending to the end of the membrane anchor sequence. In some embodiments the fragment comprises the C-terminus of a full-length sortase amino acid sequence. In some embodiments, the fragment comprises the catalytic core region of a sortase. In one embodiment the core region is from about position 60 to about position 206 of SrtA, e.g., *S. aureus* SrtA, or about from position 82 to about position 249 of Strep. SrtA.

Sortases from other organisms also can be utilized in the processes as reported herein. Such sortases often are encoded by nucleotide sequences substantially identical or similar to the nucleotide sequences that encode SrtA. A similar or substantially identical nucleotide sequence may include modifications to the native sequence, such as substitutions, deletions, or insertions of one or more nucleotides. Included are nucleotide sequences that are at least 55%, 60%, 65%, 70%, 75%, 80%, or 85% or more identical to a native nucleotide sequence, and often are 90% or 95% or more identical to the native nucleotide sequence (each identity percentage can include a 1%, 2%, 3% or 4% variance). One test for determining whether two nucleic acids are substantially identical is to determine the percentage of identical nucleotide positions shared between two nucleic acids.

SrtA nucleotide sequences may be used as "query sequences" to perform a search against public databases to identify related sequences. Such searches can be performed using the NBLAST and XBLAST programs (version 2.0) of Altschul, et al. (J. Mol. Biol. 215 (1990) 403-410). BLAST nucleotide searches can be performed with the NBLAST program, score=100, word-length=12 to obtain homologous nucleotide sequences. To obtain gapped alignments for comparison purposes, gapped BLAST can be utilized as described in Altschul, et al. (Nuc. Acids Res. 25 (1997) 3389-3402). When utilizing BLAST and Gapped BLAST programs, default parameters of the respective programs (e.g., XBLAST and NBLAST) can be used (see e.g. www.ncbi.nlm.nih.gov).

A variant amino acid sequence departs from a native amino acid sequence. Amino acid substitutions may be made on the basis of similarity in polarity, charge, solubility, hydrophobicity, hydrophilicity, helix-forming properties and/or amphipathic properties and the resulting variants are screened for enzymatic activity with a suitable assay, such as that reported in European patent application EP14198535. For example, negatively charged amino acids include aspartic acid and glutamic acid; positively charged amino acids include lysine and arginine; and amino acids with uncharged polar or non-polar head groups having similar hydrophilicity values include leucine, isoleucine, valine, glycine, alanine, asparagine, glutamine, serine, threonine, phenylalanine, and tyrosine. In certain embodiments, conservative substitutions may be made, according to the following Table. Amino acids in the same block in the second column and in the same line in the third column may be substituted for one another other in a conservative substitution. Certain conservative substitutions are substituting an amino acid in one row of the third column corresponding to a block in the second column with an amino acid from another row of the third column within the same block in the second column.

| aliphatic amino acid residues | non-polar | G, A, P |
| --- | --- | --- |
| | | I, L, V |
| | polar, non-charged | C, S, T, M |
| | | N, Q |
| | polar, charged | D, E |
| | | K, R |
| aromatic | | H, F, W, Y |

In certain embodiments homologous substitution may occur, which is a substitution or replacement of like amino acids, such as basic for basic, acidic for acidic, polar for polar amino acids, and hydrophobic for hydrophobic, for example. Non-homologous substitutions can be introduced to a native sequence, such as from one class of residue to another (e. g. a non-hydrophobic to a hydrophobic amino acid), or substituting a naturally occurring amino acid with an unnatural amino acids or non-classical amino acid replacements.

In the methods as reported herein the sortase, the sortase-motif comprising polypeptide (i.e. the acyl donor), and the nucleophile (i.e. the acyl acceptor) are incubated together under conditions suitable to effect the formation of a peptide bond between the N-terminal part of the sortase-motif comprising polypeptide and the nucleophile. As used herein, the term "incubating" or grammatical equivalents thereof denotes that the components of the process are brought in close proximity to one another to allow contact between the molecules. Incubating can be done by adding them to one reaction vessel, for example. The components in the system may be mixed in a variety of manners, such as by oscillating a vessel, subjecting a vessel to a vortex generating apparatus, or repeated mixing with a pipette or pipettes, for example. The components may be added in any order to the system.

The sortase reaction may be performed in any convenient vessel (e.g., tubes such as microfuge tubes, flask, dish), microtiter plates (e.g., 96-well or 384-well plates), glass slides, silicon chips, filters, or any solid or semisolid support having surface (optionally coated) having molecules immobilized thereon and optionally oriented in an array (see, e.g., U.S. Pat. No. 6,261,776 and Fodor, Nature 364 (1993) 555-556), and microfluidic devices (see, e.g., U.S. Pat. Nos. 6,440,722; 6,429,025; 6,379,974; and 6,316,781).

The reaction mixture is generally cell free and further does not include bacterial cell wall components or intact bacterial cell walls. In some embodiments, the sortase-motif comprising polypeptide and/or the nucleophile are expressed by one or more recombinant nucleotide sequences in a cell, which nucleotide sequences are integrated into the cell genome or non-integrated (e.g., in a plasmid).

The reaction mixture is maintained at any convenient temperature at which the sortase reaction can be performed. In some embodiments, the sortase reaction is performed at a temperature between and including about 15° C. and about 50° C. In some embodiments, the sortase reaction is performed at a temperature between and including about 23° C. and about 37° C. In certain embodiments, the temperature is room temperature (i.e. about 20° C. to 25° C.). The temperature can be optimized by repetitively performing the same sortase reaction at different temperatures and determining ligation rates.

Any convenient volume and component ratio can be used.

In certain embodiments, a (molar) ratio of 1:1000 or greater of sortase enzyme to sortase-motif comprising polypeptide is utilized, or a (molar) ratio of 1:1000 or greater of sortase enzyme to nucleophile is utilized. In specific embodiments, ratios of sortase enzyme to sortase-motif comprising polypeptide or enzyme to nucleophile is about 1:1, including 1:2 or greater, 1:3 or greater, 1:4 or greater, 1:5 or greater, 1:6 or greater, 1:7 or greater, 1:8 or greater, and 1:9 or greater.

In some embodiments, the sortase-motif comprising polypeptide is present at a concentration ranging from about 10 µM to about 10 mM. In some embodiments, the sortase-motif comprising polypeptide is present at a concentration ranging from about 100 µM to about 1 mM. In some embodiments, the sortase-motif comprising polypeptide is present at a concentration ranging from about 100 µM to about 50 mM. In some embodiments, the sortase-motif comprising polypeptide is present at a concentration ranging from about 200 µM to about 1 mM. In some embodiments, the sortase-motif comprising polypeptide is present at a concentration ranging from about 200 µM to about 800 µM. In some embodiments, the sortase-motif comprising polypeptide is present at a concentration ranging from about 400 µM to about 600 µM.

In certain embodiments the nucleophile is present in excess with respect to the sortase-motif comprising polypeptide. In certain embodiments, the nucleophile is present in 10-fold excess with respect to the sortase-motif polypeptide. In certain embodiments, the nucleophile is present in 25-fold excess with respect to the sortase-motif polypeptide. In certain embodiments, the nucleophile is present in 50-fold excess with respect to the sortase-motif polypeptide. In certain embodiments, the nucleophile is present in 100-fold excess with respect to the sortase-motif polypeptide. In certain embodiments, the nucleophile is present in 250-fold excess with respect to the sortase-motif polypeptide.

In certain embodiments, the nucleophile is present at a concentration ranging from about 1 µM to about 50 mM. In certain embodiments, the nucleophile is present at a concentration ranging from about 15 µM to about 1500 µM. In certain embodiments, the nucleophile is present at a concentration ranging from about 25 µM to about 1000 µM. In certain embodiments, the nucleophile is present at a concentration ranging from about 40 µM to about 250 µM.

In certain embodiments, the sortase is present at a concentration ranging from about 1 µM to about 500 µM. In certain embodiments, the sortase is present at a concentration ranging from about 15 µM to about 150 µM. In certain embodiments, the sortase is present at a concentration ranging from about 25 µM to about 100 µM. In certain embodiments, the sortase is present at a concentration ranging from about 40 µM to about 60 µM.

In certain embodiments, the method is performed in a reaction mixture comprising an aqueous environment. Water with an appropriate buffer and/or salt content often may be utilized. An alcohol or organic solvent may be included in certain embodiments. The amount of an organic solvent often does not appreciably esterify a protein or peptide in the ligation process (e.g., esterified protein or peptide often increase only by 5% or less upon addition of an alcohol or organic solvent). Alcohol and/or organic solvent contents sometimes are 20% or less, 15% or less, 10% or less or 5% or less, and in embodiments where a greater amount of an alcohol or organic solvent is utilized, 30% or less, 40% or less, 50% or less, 60% or less, 70% or less, or 80% or less alcohol or organic solvent is present. In certain embodiments, the reaction mixture includes only an alcohol or an organic solvent, with only limited amounts of water if it is present.

In some embodiments, the reaction mixture comprises a buffer. A person skilled in the art will be familiar with a variety of buffers that could be used in accordance with the methods as reported herein. In some embodiments, the buffer solution comprises calcium ions. In certain embodiments, the buffer solution does not contain substances that precipitate calcium ions. In some embodiments, the buffer solution does not include phosphate ions. In some embodiments, the buffer solution does not contain chelating agents.

In some embodiments, the method is performed at a pH value in the range of from 6 to 8.5. In some embodiments, the method is performed at a pH value in the range of from 6 to 8. In some embodiments, the method is performed at a pH value in the range of from 6 to 7.5. In some embodiments, the method is performed at a pH value in the range of from 6.5 to 8.5. In some embodiments, the method is performed at a pH value in the range of from 7 to 8.5. In some embodiments, the method is performed at a pH value in the range of from 7.5 to 8.5. In some embodiments, the method is performed at a pH value in the range of from 7.0 to 8.5. In some embodiments, the method is performed at a pH value in the range of from 7.3 to 7.8.

One or more components of the reaction mixture or the product may be immobilized to a solid support. The attachment between the reaction mixture component and the solid support may be covalent or non-covalent (see, e.g., U.S. Pat. No. 6,022,688 for non-covalent attachments). The solid support may be one or more surfaces of the system, such as one or more surfaces in each well of a microtiter plate, a surface of a glass slide or silicon wafer, BIAcore chip, a surface of a particle, e.g., a bead (see e.g., Lam, Nature 354 (1991) 82-84) that is optionally linked to another solid support, or a channel in a microfluidic device, for example. Types of solid supports, linker molecules for covalent and non-covalent attachments to solid supports, and methods for immobilizing molecules to solid supports are known (see, e.g., U.S. Pat. Nos. 6,261,776; 5,900,481; 6,133,436; 6,022, 688; WO 2001/18234). Any material may be used, e.g., plastic (e.g., polystyrene), metal, glass, cellulose, gels (e.g., formed at least in part from organic polymers such as PDMS), etc. In some embodiments the solid support is semi-solid and/or gel-like, deformable, flexible, or the like.

Any polypeptide, eventually after introduction of a sortase-motif or an oligoglycine or -alanine, may be used as sortase-motif comprising polypeptide or nucleophile in the methods as reported herein.

Summarizing the above, the first substrate, also denoted as donor, comprises the sortase recognition motif. It is cleaved by the sortase after the threonine residue in the recognition motif. Thereby a C-terminal activated carboxyl group (acyl intermediate) is generated. The second substrate, also denoted as acceptor or nucleophile, provides a free N-terminal amino group. Between the free amino group and the activated carboxyl group a peptide bond is formed in the sortase catalyzed transpeptidation reaction.

Thus, for the enzymatic sortase mediated transpeptidation reaction it is only required that a donor comprising a sortase recognition motif and an acceptor comprising an N-terminal free glycine, alanine, cysteine or an equivalent functional group is incubated with a polypeptide having sortase A catalytic activity. The remainder of the donor as well as of the acceptor does not interfere with the reaction.

Thus, a sortase mediated transpeptidation reaction can be performed with virtually any protein or small molecule independently of each other as donor or acceptor as long as these comprise a pair of sortase recognition sequence and nucleophile.

This is confirmed by the art.

For example, Marraffini et al. (Microbiol. Mol. Biol. Rev. 70 (2006) 192-221) reported that sortase A can be used to incorporate chemicals containing glycine residues with a free amino group to the LPXTG motif (SEQ ID NO: 1) of recombinant proteins, i.e. without limitation of the protein. Presented examples are the conjugation of triglycyl-lysine-folate with (GFP or Cre or p27)-LPETG-His6 (SEQ ID NO: 173) with high efficiency, the incorporation of the branched peptide AT-P-022 into polypeptides, and the self-cleavage of chimeras of His6-sortase-LPETG-target protein ("His6" and "LPETG" disclosed as SEQ ID NOS 9 and 4, respectively) (the fusion cleaves itself once the enzyme has been activated by the addition of calcium and triglycine (SEQ ID NO: 29)).

Further, Antos et al. (J. Am. Chem. Soc. 131 (2009) 10800-10801) reported that the transpeptidation reaction catalyzed by sortase A allows site-specific derivatization of proteins with virtually any type of functional material. Target proteins are engineered to contain the recognition site (LPXTG (SEQ ID NO: 1)) near their C terminus, thus allowing a trans-acylation reaction in which the residues C-terminal to threonine are exchanged for a synthetic oligoglycine peptide. It is reported that the terminal G residue of the sortase recognition motif can be replaced by a methyl ester without imparting the reaction. In this document nucleophiles comprising either a fluorescent label or a protein were used for the conjugation to cholera toxin B subunit.

Further, Popp et al. (Proc. Natl. Acad. Sci. USA 108 (2011) 3169-3174) reported the use of Sortase for polypeptide cyclization and PEGylation. The method is general and applicable to a wide variety of proteins. The sortase transpeptidase reaction allows facile site-specific PEGylation of multiple distinct proteins, as exemplified using interferon a2, GCSF, and erythropoietin. In all cases tested, the site-specific C-terminal PEGylation proceeded efficiently.

In EP 2 990 423 a self-cleaving sortase construct is reported. In this construct the sortase recognition sequence LPETG (SEQ ID NO: 4) and the catalytic sortase domain have been combined in the same molecule. As protein comprising the sortase recognition sequence any protein, such as e.g. a protein selected from the group comprising polymer proteins, glycoproteins, cytokines, growth factor, blood preparations, vaccines, hormones, enzymes, antibodies and parts or fragments thereof (isolated light or heavy chains).

IV. Sortases

Full length *Streptococcus pyogenes* Sortase A (Uniprot Q1J6K9; catalytic core underlined; conserved histidine underlined) has the following amino acid sequence:

```
                                        (SEQ ID NO: 33)
MVKKQKRRKI KSMSWARKLL IAVLLILGLA LLFNKPIRNT

LIARNSNKYQ VTKVSKKQIK KNKEAKSTFD FQAVEPVSTE
```

-continued

```
SVLQAQMAAQ QLPVIGGIAI PELGINLPIF KGLGNTELIY

GAGTMKEEQV MGGENNYSLA SHHIFGITGS SQMLFSPLER

AQNGMSIYLT DKEKIYEYII KDVFTVAPER VDVIDDTAGL

KEVTLVTCTD IEATERIIVK GELKTEYDFD KAPADVLKAF

NHSYNQVST.
```

The amino acid sequence of the mature soluble sortase A derived from *Streptococcus pyogenes* is

```
                                         (SEQ ID NO: 06)
VLQAQMAAQQ LPVIGGIAIP ELGINLPIFK GLGNTELIYG

AGTMKEEQVM GGENNYSLAS HHIFGITGSS QMLFSPLERA

QNGMSIYLTD KEKIYEYIIK DVFTVAPERV DVIDDTAGLK

EVILVICTDI EATERIIVKG ELKTEYDFDK APADVLKAFN

HSYNQVST.
```

Full length *Staphylococcus aureus* Sortase A (see Mazmanian et al.; catalytic core underlined; conserved histidine underlined) has the following amino acid sequence:

```
                                         (SEQ ID NO: 26)
MKKWTNRLMT IAGVVLILVA AYLFAKPHID NYLHDKDKDE

KIEQYDKNVK EQASKDKKQQ AKPQIPKDKS KVAGYIEIPD

ADIKEPVYPG PATPEQLNRG VSFAEENESL DDQNISIAGH

TFIDRPNYQF TNLKAAKKGS MVYFKVGNET RKYKMTSIRD

VKPTDVGVLD EQKGKDKQLT LITCDDYNEK TGVWEKRKIF

VATEVK.
```

*Staphylococcus aureus* Sortase A without the N-terminal 28 amino acid residues (N(2-29) transmembrane domain) has the following amino acid sequence:

```
                                         (SEQ ID NO: 34)
MDNYLHDKDK DEKIEQYDKN VKEQASKDKK QQAKPQIPKD

KSKVAGYIEI PDADIKEPVY PGPATPEQLN RGVSFAEENE

SLDDQNISIA GHTFIDRPNY QFTNLKAAKK GSMVYFKVGN

ETRKYKMTSI RDVKPTDVGV LDEQKGKDKQ LTLITCDDYN

EKTGVWEKRK IFVATEVK.
```

*Staphylococcus aureus* Sortase A without the N-terminal 59 amino acid residues (transmembrane domain) has the following amino acid sequence:

```
                                         (SEQ ID NO: 05)
QAKPQIPKDK SKVAGYIEIP DADIKEPVYP GPATPEQLNR

GVSFAEENES LDDQNISIAG HTFIDRPNYQ FTNLKAAKKG

SMVYFKVGNE TRKYKMTSIR DVKPTDVGVL DEQKGKDKQL

TLITCDDYNE KTGVWEKRKI FVATEVK.
```

Full length Sortase A from *Listeria monocytogenes* has the following amino acid sequence (the catalytic center is underlined; the conserved histidine is underlined):

```
                                         (SEQ ID NO: 35)
MLKKTIAAAA LAAGLLLIFS PFIKNGIVKY MSGHETIEQY

KASDIKKNNE KDATFDFESV QLPSMTSVIK GAANYDKDAV

VGSIAVPSVD VNLLVFKGTN TANLLAGATT MRSDQVMGKG

NYPLAGHHMR DESMLFGPIM KVKKGDKIYL TDLENLYEYT

VTETKTIDET EVSVIDDTKD ARITLITCDK PTETTKRPVA

VGELEKTEKL TKELENKYFP SK.
```

The amino acid sequence of the mature soluble sortase A derived from *Listeria monocytogenes* Sortase A has the following amino acid sequence:

```
                                         (SEQ ID NO: 38)
ANYDKDAVVG SIAVPSVDVN LLVFKGTNTA NLLAGATTMR

SDQVMGKGNY PLAGHHMRDE SMLFGPIMKV KKGDKIYLTD

LENLYEYTVT ETKTIDETEV SVIDDTKDAR ITLITCDKPT

ETTKRPVAVG ELEKTEKLTK ELENKYFPSK.
```

With the assay as reported in Example 6 it is easily possible to determine which polypeptide or fragment of a sortase A (still) has sortase A enzymatic activity.

V. Sortases in Different Solvent Systems

Sortase A from *Staphylococcus aureus* was mixed with hexane, triethylamine, acetone, isopropanol, acetonitrile, dimethyl sulfoxide, DES (choline chloride:glycerol 1:2, choline chloride:ethylene glycol, choline chloride:glucose/fructose 1:1 and choline chloride:2,3-butanediol 2,3-butanediol 1:4) or water and analyzed for solubility. The Sa-SrtA is highly soluble in the DES and in water but not in the other solvents.

The activity of the Sa-SrtA in all mentioned solvents was tested. The water-soluble or water-based solvents were supplemented with 15% buffer to ensure the optimal pH and $Ca^{2+}$ concentration. The reaction mixture (0.1 mM Sa-SrtA and 1 mM of substrates (ULPETGGRR (SEQ ID NO: 174) and GGGG-PEG-Biotin (SEQ ID NO: 30))) was incubated (8 h, 37° C.), the reaction mixtures were analyzed by HPLC and the peaks were identified by Mass spectrometry.

In the following Table the solubility and activity of Sa-SrtA in different solvents is shown (+: completely soluble/significant amounts of ligation product were formation). The DES from fructose or glucose was nearly solid at RT and therefore not suitable for this approach. In the DES from ethylene glycol ligation product could be observed but Sa-SrtA is not stable over time.

| Solvent | Sa-SrtA solubility | Sa-SrtA activity |
|---|---|---|
| Hexane | − | − |
| Triethylamine | − | − |
| Acetone | − | − |
| Isopropanol | − | − |
| Acetonitrile | − | − |
| Dimethyl sulfoxide | − | − |

-continued

| Solvent | Sa-SrtA solubility | Sa-SrtA activity |
|---|---|---|
| ChCl:Glycerin 1:2 | + | + |
| ChCl:Ethylene glycol 1:3 | + | +/− (instable) |
| ChCl:Fructose 1:1 | DES is to viscous at mesophilic temperatures | |
| ChCl:Glucose/1:1 | | |
| ChCl:2,3-Butanediol 2,3-Butanediol 1:4 | + | − |
| Water | + | + |

Thus, Sa-SrtA is active in ChCl:Glycerol based DES containing aqueous co-solvent. To evaluate the influence of the amount of co-solvent on the Sortase reaction, varied ratios of water and DES were investigated. The reactions were analyzed for ligation product formation over time. The results are shown in FIG. 7.

To exclude stability issues of Sa-SrtA towards the DES, 0.1 mM Sortase was incubated for 24 h at room temperature in 90% DES and no loss of activity could be detected.

VI. The Method and Use as Reported Herein

One aspect as reported herein is a method for the enzymatic production of a polypeptide comprising the following step
incubating
i) a first polypeptide (optionally comprising within the 100 C-terminal amino acid residues) the amino acid sequence LPXTG (SEQ ID NO: 01, wherein X can be any amino acid residue) or LPXTA (SEQ ID NO: 41, wherein X can be any amino acid residue),
ii) a second polypeptide that has i) a glycinyl, an alaninyl, or a cysteinyl compound at its N-terminus, or ii) an oligoglycine, or oligoalanine, or a cysteine amino acid residue followed by one to three glycine or alanine amino acid residues at its N-terminus, or iii) a lysine amino acid residue within its 5 N-terminal amino acid residues, and
iii) a third polypeptide with sortase A activity,
in a deep eutectic solvent
and thereby producing a polypeptide.

In one embodiment the cysteinyl compound is a compound that comprises at position 1 a cysteine amino acid residue with free alpha amino group (in one embodiment a $NH_2$ or $NH_{3+}$), and a carboxy group, which is part of a peptide bond.

In one embodiment the alanyl compound is a compound that comprises at position 1 an alanine amino acid residue with free alpha amino group (in one embodiment a $NH_2$ or $NH_{3+}$), and a carboxy group, which is part of a peptide bond.

In one embodiment the glycinyl compound is a compound that comprises at position 1 a glycine amino acid residue with free alpha amino group (in one embodiment a $NH_2$ or $NH_{3+}$), and a carboxy group, which is part of a peptide bond.

In one embodiment the third polypeptide with sortase A activity is derived from *Staphylococcus aureus* sortase A, or from *Streptococcus pyogenes* Sortase A, or from *Listeria monocytogenes* Sortase A.

In one embodiment the third polypeptide is a sortase A or a sortase A fragment that has sortase A catalytical activity. In one embodiment sortase A catalytical activity is determined using a bond forming assay. In one embodiment the bond forming assay is the assay according to current example 6.

In one embodiment the third polypeptide comprises the amino acid sequence of SEQ ID NO: 05, SEQ ID NO: 06 or SEQ ID NO: 38. In one preferred embodiment the third polypeptide comprises the amino acid sequence of SEQ ID NO: 38.

In one embodiment the third polypeptide comprises additionally a tag at its N- or C-terminus either conjugated directly or via an intervening linker. In one embodiment the third polypeptide is consisting of the amino acid sequence of SEQ ID NO: 38 and the C-terminal tag of SEQ ID NO: 32. In one embodiment the third polypeptide is consisting of the amino acid sequence of SEQ ID NO: 38.

In one embodiment the method is for the enzymatic conjugation of two polypeptides.

In one embodiment the deep eutectic solvent comprises choline chloride. In one embodiment the deep eutectic solvent is a mixture of choline chloride with glycerol at a molar ratio of 1:2 (v/v). In one embodiment the deep eutectic solvent comprises an aqueous co-solvent. In one embodiment the deep eutectic solvent comprises up to 10% (v/v) co-solvent. In one embodiment the deep eutectic solvent comprises up to 5% (v/v) co-solvent. In one preferred embodiment the deep eutectic solvent is a mixture of choline chloride with glycerol at a molar ratio of 1:2 (v/v) comprising up to 5% (v/v) aqueous co-solvent.

In one embodiment the second polypeptide has at its N-terminus the amino acid sequence GGG (SEQ ID NO: 29), AAA, CGG, CAA, KGG, or KAA.

In one embodiment the first polypeptide comprises within the 250 C-terminal amino acid residues the amino acid sequence LPXTG (SEQ ID NO: 01, wherein X can be any amino acid residue) or LPXTA (SEQ ID NO: 41, wherein X can be any amino acid residue). In one embodiment the first polypeptide comprises within the 100 C-terminal amino acid residues the amino acid sequence LPXTG (SEQ ID NO: 01, wherein X can be any amino acid residue) or LPXTA (SEQ ID NO: 41, wherein X can be any amino acid residue). In one embodiment the first polypeptide comprises within the 25 C-terminal amino acid residues the amino acid sequence LPXTG (SEQ ID NO: 01, wherein X can be any amino acid residue) or LPXTA (SEQ ID NO: 41, wherein X can be any amino acid residue). In one embodiment the first polypeptide comprises within the 10 C-terminal amino acid residues the amino acid sequence LPXTG (SEQ ID NO: 01, wherein X can be any amino acid residue) or LPXTA (SEQ ID NO: 41, wherein X can be any amino acid residue).

In one embodiment the first polypeptide comprises at its C-terminus the amino acid sequence LPXTG (SEQ ID NO: 01, wherein X can be any amino acid residue) or LPXTA (SEQ ID NO: 41, wherein X can be any amino acid residue). In one embodiment the first polypeptide comprises at its C-terminus the amino acid sequence LPETG (SEQ ID NO: 04) or LPETA (SEQ ID NO: 42).

In one embodiment the first polypeptide and the second polypeptide are independently of each other selected from an antibody variable domain, an antibody heavy chain Fab-fragment, an antibody Fc-region, a tag, a peptide comprising the amino acid sequence LPXTG (SEQ ID NO: 01, wherein X can be any amino acid residue) or LPXTA (SEQ ID NO: 41, wherein X can be any amino acid residue), a linker, and a non-sortase motif moiety.

One aspect as reported herein is the use of a deep eutectic solvent comprising choline chloride and glycerol at a molar ratio of 1:2 (v/v) and further comprising up to 5% (v/v) aqueous co-solvent as solvent in an enzymatic transamidation reaction catalyzed by Sortase A.

One aspect as reported herein is a method for the Sortase A catalyzed production of a polypeptide comprising the following step incubating in a deep eutectic solvent comprising choline chloride and glycerol at a molar ratio of 1:2 (v/v) and further comprising up to 5% (v/v) aqueous co-solvent
i) a first polypeptide comprising (optionally within the 100 C-terminal amino acid residues) the amino acid sequence LPXTG (SEQ ID NO: 01, wherein X can be any amino acid residue) or LPXTA (SEQ ID NO: 41, wherein X can be any amino acid residue),
ii) a second polypeptide that has i) a glycinyl, an alaninyl, or a cysteinyl compound at its N-terminus, or ii) an oligoglycine, or oligoalanine, or a cysteine amino acid residue followed by one to three glycine or alanine amino acid residues at its N-terminus, or iii) a lysine amino acid residue within its 5 N-terminal amino acid, and
iii) a (soluble) sortase that has the amino acid sequence of SEQ ID NO: 05, or SEQ ID NO: 06, or SEQ ID NO: 38 and optionally comprising the C-terminal tag of SEQ ID NO: 32, and thereby producing a polypeptide.

The First or Second Polypeptide

The sortase-motif (amino acid sequence) may be conjugated to or incorporated in, if it is not directly comprised in one of these molecules, a therapeutic agent (drug), a cytotoxic agent (e.g. a toxin such as doxorubicin or pertussis toxin), a fluorophore such as a fluorescent dye like fluorescein or rhodamine, a chelating agent for an imaging or radiotherapeutic metal, a peptidyl or non-peptidyl label, a tag, or a clearance-modifying agent such as various isomers of polyethylene glycol, a peptide that binds to a third component, another carbohydrate or lipophilic agent, or a small molecule, such as e.g. a synthetic small molecule (e.g. acetyl salicylic acid). If the motif is incorporated via conjugation the conjugation can be either directly or via an intervening linker. Furthermore the first and/or second polypeptide can either be recombinantly produced or can be synthetic or semi-synthetic, i.e. recombinantly produced and thereafter chemically modified.

a) Therapeutic Agents

The therapeutic agent can be any compound, moiety or group which has a therapeutic effect, such as e.g. an antibody, a cytotoxic or cytostatic compound. The antibody can be a full length or complete antibody or an antigen-binding fragment thereof.

A number of therapeutic antibodies directed against cell surface molecules and their ligands are known, such as Rituxan/MabThera/Rituximab, 2H7/Ocrelizumab, Zevalin/Ibrizumomab, Arzerra/Ofatumumab (CD20), HLL2/Epratuzumab, Inotuzomab (CD22), Zenapax/Daclizumab, Simulect/Basiliximab (CD25), Herceptin/Trastuzumab, Pertuzumab (Her2/ERBB2), Mylotarg/Gemtuzumab (CD33), Raptiva/Efalizumab (Cd11a), Erbitux/Cetuximab (EGFR, epidermal growth factor receptor), IMC-1121B (VEGF receptor 2), Tysabri/Natalizumab (α4-subunit of α4ß1 and α4ß7 integrins), ReoPro/Abciximab (gpIIb-gpIIa and αvß3-integrin), Orthoclone OKT3/Muromonab-CD3 (CD3), Benlysta/Belimumab (BAFF), Tolerx/Oteliximab (CD3), Soliris/Eculizumab (C5 complement protein), Actemra/Tocilizumab (IL-6R), Panorex/Edrecolomab (EpCAM, epithelial cell adhesion molecule), CEA-CAM5/Labetuzumab (CD66/CEA, carcinoembryonic antigen), CT-11 (PD-1, programmed death-1 T-cell inhibitory receptor, CD-d279), H224G11 (c-Met receptor), SAR3419 (CD19), IMC-A12/Cixutumumab (IGF-1R, insulin-like growth factor 1 receptor), MEDI-575 (PDGF-R, platelet-derived growth factor receptor), CP-675, 206/Tremelimumab (cytotoxic T lymphocyte antigen 4), RO5323441 (placenta growth factor or PGF), HGS1012/Mapatumumab (TRAIL-R1), SGN-70 (CD70), Vedotin (SGN-35)/Brentuximab (CD30), and ARH460-16-2 (CD44).

The conjugates obtained with the method as reported herein can be used in the preparation of medicaments for the treatment of e.g. an oncologic disease, a cardiovascular disease, an infectious disease, an inflammatory disease, an autoimmune disease, a metabolic (e.g., endocrine) disease, or a neurological (e.g. neurodegenerative) disease. Exemplary non-limiting examples of these diseases are Alzheimer's disease, non-Hodgkin's lymphomas, B-cell acute and chronic lymphoid leukemias, Burkitt lymphoma, Hodgkin's lymphoma, hairy cell leukemia, acute and chronic myeloid leukemias, T-cell lymphomas and leukemias, multiple myeloma, glioma, Waldenstrom's macroglobulinemia, carcinomas (such as carcinomas of the oral cavity, gastrointestinal tract, colon, stomach, pulmonary tract, lung, breast, ovary, prostate, uterus, endometrium, cervix, urinary bladder, pancreas, bone, liver, gall bladder, kidney, skin, and testes), melanomas, sarcomas, gliomas, and skin cancers, acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

A number of cell surface markers and their ligands are known. For example cancer cells have been reported to express at least one of the following cell surface markers and or ligands, including but not limited to, carbonic anhydrase IX, alpha fetoprotein, alpha-actinin-4, A3 (antigen specific for A33 antibody), ART-4, B7, Ba-733, BAGE, BrE3-antigen, CA125, CAMEL, CAP-1, CASP-8/m, CCCL19, CCCL21, CD1, CD1a, CD2, CD3, CD4, CDS, CD8, CD1-1A, CD14, CD15, CD16, CD18, CD19, CD20, CD21, CD22, CD23, CD25, CD29, CD30, CD32b, CD33, CD37, CD38, CD40, CD40L, CD45, CD46, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, CXCR7, CXCL12, HIF-1-alpha, colon-specific antigen-p (CSAp), CEA (CEACAM5), CEACAM6, c-met, DAM, EGFR, EGFRvIII, EGP-1, EGP-2, ELF2-M, Ep-CAM, Flt-1, Flt-3, folate receptor, G250 antigen, GAGE, GROB, HLA-DR, HM1.24, human chorionic gonadotropin (HCG) and its subunits, HER2/neu, HMGB-1, hypoxia inducible factor (HIF-1), HSP70-2M, HST-2 or 1a, IGF-1R, IFN-gamma, IFN-alpha, IFN-beta, IL-2, IL-4R, IL-6R, IL-13R, IL-15R, IL-17R, IL-18R, IL-6, IL-8, IL-12, IL-15, IL-17, IL-18, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, pancreatic cancer mucin, placental growth factor, p53, PLAGL2, prostatic acid phosphatase, PSA, PRAME, PSMA, P1GF, ILGF, ILGF-1R, IL-6, IL-25, RS5, RANTES, T101, SAGE, 5100, survivin, survivin-2B, TAC, TAG-72, tenascin, TRAIL receptors, TNF-alpha, Tn-antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi, et al., Clin. Cancer Res. 12 (2006) 5023-5032; Parmiani, et al, J. Immunol. 178 (2007) 1975-1979; Novellino, et al., Cancer Immunol. Immunother. 54 (2005) 187-207).

Thus, antibodies recognizing specific cell surface receptors including their ligands can be used for specific and selective targeting and binding to a number/multitude of cell surface markers that are associated with a disease. A cell surface marker is a polypeptide located on the surface of a cell (e.g. a disease-related cell) that is e.g. associated with signaling event or ligand binding.

In one embodiment, for the treatment of cancer/tumors multispecific binding molecules/bispecific antibodies are produced that target tumor-associated antigens, such as those reported in Herberman, "Immunodiagnosis of Cancer", in Fleisher (ed.), "The Clinical Biochemistry of Cancer", page 347 (American Association of Clinical Chemists (1979)) and in U.S. Pat. Nos. 4,150,149; 4,361,544; and 4,444,744.

Reports on tumor associated antigens (TAAs) include Mizukami, et al., (Nature Med. 11 (2005) 992-997); Hatfield, et al., (Curr. Cancer Drug Targets 5 (2005) 229-248); Vallbohmer, et al., (J Clin. Oncol. 23 (2005) 3536-3544); and Ren, et al., (Ann. Surg. 242 (2005) 55-63), each incorporated herein by reference with respect to the TAAs identified.

Where the disease involves a lymphoma, leukemia or autoimmune disorder, targeted antigens may be selected from the group consisting of CD4, CD5, CD8, CD14, CD15, CD19, CD20, CD21, CD22, CD23, CD25, CD33, CD37, CD38, CD40, CD40L, CD46, CD54, CD67, CD74, CD79a, CD80, CD126, CD138, CD154, CXCR4, B7, MUC1 or 1a, HM1.24, HLA-DR, tenascin, VEGF, P1GF, ED-B fibronectin, an oncogene, an oncogene product (e.g., c-met or PLAGL2), CD66a-d, necrosis antigens, IL-2, T101, TAG, IL-6, MIF, TRAIL-R1 (DR4) and TRAIL-R2 (DR5).

A number of bispecific antibodies are known directed against two different targets, such as BCMA/CD3, different antigens of the HER family in combination (EGFR, HER2, HER3), CD19/CD3, IL17RA/IL7R, IL-6/IL-23, IL-1-beta/IL-8, IL-6 or IL 6R/IL-21 or IL-21R, first specificity directed to a glycoepitope of an antigen selected from the group consisting of Lewis x-, Lewis b- and Lewis y-structures, Globo H-structures, KH1, Tn-antigen, TF-antigen and carbohydrate structures of Mucins, CD44, glycolipids and glycosphingolipids, such as Gg3, Gb3, GD3, GD2, Gb5, Gm1, Gm2, sialyltetraosylceramide and a second specificity directed to an ErbB receptor tyrosine kinase selected from the group consisting of EGFR, HER2, HER3 and HER4, GD2 in combination with a second antigen binding site is associated with an immunological cell chosen from the group consisting of T lymphocytes NK cell, B-lymphocytes, dendritic cells, monocytes, macrophages, neutrophils, mesenchymal stem cells, neural stem cells, ANG2/VEGF, VEGF/PDGF-beta, Vascular Endothelial Growth Factor (VEGF) acceptor 2/CD3, PSMA/CD3, EPCAM/CD3, combinations of an antigen is selected from a group consisting of VEGFR-1, VEGFR-2, VEGFR-3, FLT3, c FMS/CSF1R, RET, c-Met, EGFR, Her2/neu, HER3, HER4, IGFR, PDGFR, c-KIT, BCR, integrin and MMPs with a water-soluble ligand is selected from the group consisting of VEGF, EGF, PIGF, PDGF, HGF, and angiopoietin, ERBB-3/C-MET, ERBB-2/C-MET, EGF receptor 1/CD3, EGFR/HER3, PSCA/CD3, C-MET/CD3, ENDOSIALIN/CD3, EPCAM/CD3, IGF-1R/CD3, FAPALPHA/CD3, EGFR/IGF-1R, IL 17A/F, EGF receptor 1/CD3, and CD19/CD16.

Toxic drug moieties include: (i) chemotherapeutic agents, which may function as microtubule inhibitors, mitosis inhibitors, topoisomerase inhibitors, or DNA intercalators; (ii) protein toxins, which may function enzymatically; and (iii) radioisotopes.

Exemplary toxic drug moieties include, but are not limited to, a maytansinoid, an auristatin, a dolastatin, a trichothecene, CC1065, a calicheamicin and other enediyne antibiotics, a taxane, an anthracycline, and stereoisomers, isosters, analogs or derivatives thereof.

Protein toxins include diphtheria-A chain, non-binding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, *Aleurites fordii* proteins, dianthin proteins, *Phytolaca americana* proteins (PAPI, PAPII, and PAP-5), *Momordica charantia* inhibitor, curcin, crotin, *Sapaonaria officinalis* inhibitor, gelonin, mitogellin, restrictocin, phenomycin, enomycin, and the tricothecenes (WO 93/21232).

Therapeutic radioisotopes include 32P, 33P, 90Y, 125I, 131I, 131In, 153Sm, 186Re, 188Re, 211At, 212B, 212Pb, and radioactive isotopes of Lu.

The radioisotope or other labels may be incorporated in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene triamine pentaacetic acid (MX-DTPA) is an exemplary chelating agent for conjugation of a radionuclide to the complex (WO 94/11026).

b) Labels

The non-sortase motif moiety can be a label. Any label moiety which can be covalently attached to the sortase amino acid sequence can be used (see e.g. Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The label may function to: (i) provide a detectable signal; (ii) interact with a second label to modify the detectable signal provided by the first or second label, e.g. to give FRET (fluorescence resonance energy transfer); (iii) affect mobility, e.g. electrophoretic mobility or cell-permeability, by charge, hydrophobicity, shape, or other physical parameters, or (iv) provide a capture moiety, e.g. to modulate ionic complexation.

Conjugates comprising a haptenylated label as reported herein may be useful in diagnostic assays, e.g., for detecting expression of an antigen of interest in specific cells, tissues, or serum. For diagnostic applications, a bispecific antibody will be used wherein the first binding specificity binds to a target and the second binding specificity binds to a haptenylated label. The hapten will typically be labeled with a detectable moiety. Numerous labels are available which can be generally grouped into the following categories:

(a) Radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi. Radioisotope labeled conjugates are useful in receptor targeted imaging experiments. The antigen (hapten) can be labeled with ligand reagents that bind, chelate or otherwise complex a radioisotope metal using the techniques described in Current Protocols in Immunology, (1991) Volumes 1 and 2, Coligen et al, Ed. Wiley-Interscience, New York, N.Y., Pubs. Chelating ligands which may complex a metal ion include DOTA, DOTP, DOTMA, DTPA and TETA (Macrocyclics, Dallas, Tex.). Radionuclides can be targeted via complexation with the complex as reported herein (Wu et al, Nature Biotechnology 23(9) (2005) 1137-1146). Receptor target imaging with radionuclide labeled complexes can provide a marker of pathway activation by detection and quantification of progressive accumulation of complexes or corresponding therapeutic antibodies in tumor tissue (Albert et al (1998) Bioorg. Med. Chem. Lett. 8:1207-1210).

Metal-chelate complexes suitable as labels for imaging experiments (US 2010/0111856; U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al., J. Nucl. Med. 21 (1994) 640-646; Ruegg et al., Cancer Res. 50 (1990) 4221-4226; Verel et al., J. Nucl. Med. 44 (2003) 1663-1670; Lee et al., Cancer Res. 61 (2001) 4474-4482; Mitchell, et al., J. Nucl. Med. 44 (2003) 1105-1112; Kobayashi et al., Bioconjugate Chem. 10 (1999) 103-111; Miederer et al., J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al., J. Nucl. Med. 39 (1998) 829-36; Mardirossian et al., Nucl. Med. Biol. 20 (1993) 65-74; Roselli et al., Cancer Biotherapy & Radiopharmaceuticals, 14 (1999) 209-20).

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to the antigen (hapten) using the techniques disclosed in Current Protocols in Immunology, supra, for example. Fluorescent dyes and fluorescent label reagents include those which are commercially available from Invitrogen/Molecular Probes (Eugene, Oreg., USA) and Pierce Biotechnology, Inc. (Rockford, Ill.).

Detection labels such as fluorescent dyes and chemiluminescent dyes (Briggs et al "Synthesis of Functionalised Fluorescent Dyes and Their Coupling to Amines and Amino Acids," J. Chem. Soc., Perkin-Trans. 1 (1997) 1051-1058) provide a detectable signal and are generally applicable for labeling, especially with the following properties: (i) the labeled conjugate should produce a very high signal with low background so that small quantities of conjugate can be sensitively detected in both cell-free and cell-based assays; and (ii) the labeled conjugate should be photostable so that the fluorescent signal may be observed, monitored and recorded without significant photo bleaching. For applications involving cell surface binding of labeled conjugates to membranes or cell surfaces, especially live cells, the labels should (iii) have good water-solubility to achieve effective conjugate concentration and detection sensitivity and (iv) are non-toxic to living cells so as not to disrupt the normal metabolic processes of the cells or cause premature cell death.

(c) Various enzyme-substrate labels are available or disclosed (see e.g. U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), (3-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to polypeptides are described in O'Sullivan et al "Methods for the Preparation of Enzyme-Antibody Conjugates for use in Enzyme Immunoassay", in Methods in Enzym. (ed. by J. Langone & IT Van Vunakis), Academic Press, New York, 73 (1981) 147-166.

Examples of enzyme-substrate combinations (U.S. Pat. Nos. 4,275,149; 4,318,980) include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB));

(ii) alkaline phosphatase (AP) with para-nitrophenyl phosphate as chromogenic substrate; and (iii) (3-D-galactosidase ((3-D-Gal) with a chromogenic substrate (e.g., p-nitro phenyl-(3-D-galactosidase) or fluorogenic substrate 4-methylumbelliferyl-(3-D-galactosidase.

The labeled conjugate as reported herein may be employed in any known assay method, such as ELISA, competitive binding assays, direct and indirect sandwich assays, and immunoprecipitation assays (Zola, Monoclonal Antibodies: A Manual of Techniques (1987) pp. 147-158, CRC Press, Inc.).

Labeled conjugates as reported herein are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Tinianow, J. et al, Nuclear Medicine and Biology, 37(3) (2010) 289-297; Chen et al, Bioconjugate Chem. 15 (2004) 41-49; US 2010/0111856 (v) bioluminescence; (vi) fluorescence; and (vii) ultrasound. Immunoscintigraphy is an imaging procedure in which conjugates labeled with radioactive substances are administered to an animal or human patient and a picture is taken of sites in the body where the conjugate localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 markers are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Peptide labeling methods are well known. See Haugland (2003) Molecular Probes Handbook of Fluorescent Probes and Research Chemicals, Molecular Probes, Inc.; Brinkley (1992) Bioconjugate Chem. 3:2; Garman, (1997) Non-Radioactive Labeling: A Practical Approach, Academic Press, London; Means (1990) Bioconjugate Chem. 1:2; Glazer et al Chemical Modification of Proteins. Laboratory Techniques in Biochemistry and Molecular Biology (T. S. Work and E. Work, Eds.) American Elsevier Publishing Co., New York; Lundblad, R. L. and Noyes, C. M. (1984) Chemical Reagents for Protein Modification, Vols. I and II, CRC Press, New York; Pfleiderer, G. (1985) "Chemical Modification of Proteins", Modern Methods in Protein Chemistry, H. Tschesche, Ed., Walter DeGruyter, Berlin and New York; and Wong (1991) Chemistry of Protein Conjugation and Crosslinking, CRC Press, Boca Raton, Fla.); DeLeon-Rodriguez et al, Chem. Eur. J. 10 (2004) 1149-1155; Lewis et al, Bioconjugate Chem. 12 (2001) 320-324; Li et al, Bioconjugate Chem. 13 (2002) 110-115; Mier et al Bioconjugate Chem. 16 (2005) 240-237.

c) Linker

The term "linker" denotes a bifunctional or multifunctional moiety which can be used to conjugate (link) a first moiety with a second moiety. Linked conjugates can be conveniently prepared using a linker having two reactive functionalities.

In one embodiment, a linker has a reactive site which has an electrophilic group that is reactive to a nucleophilic group present in the sortase amino acid sequence. Useful electrophilic groups include, but are not limited to, another thiol, maleimide and haloacetamide groups (see e.g. conjugation method at page 766 of Klussman et al, Bioconjugate Chemistry 15(4) (2004) 765-773).

Examples of thiol-reaction functional groups include, but are not limited to, thiol, maleimide, and alpha-haloacetyl.

The linker may comprise amino acid residues which link the sortase amino acid sequence to the non-sortase motif moiety. The amino acid residues may form a dipeptide, tripeptide, tetrapeptide, pentapeptide, hexapeptide, heptapeptide, octapeptide, nonapeptide, decapeptide, undecapeptide or dodecapeptide unit. Amino acid residues include those occurring naturally, as well as non-naturally occurring amino acid analogs, such as e.g. citrulline or β-amino acids, such as e.g. β-alanine, or ω-amino acids such as 4-aminobutyric acid.

In another embodiment, the linker has a reactive functional group which has a nucleophilic group that is reactive to an electrophilic group present in the sortase amino acid sequence. Useful electrophilic groups include, but are not limited to, aldehyde and ketone carbonyl groups. The heteroatom of a nucleophilic group of a linker can react with an electrophilic group in the sortase amino acid sequence and form a covalent bond to the sortase amino acid sequence. Useful nucleophilic groups on a linker include, but are not limited to, hydrazide, oxime, amino, hydrazine, hydrazine carboxylate, and arylhydrazide. The electrophilic group on an antigen (hapten) provides a convenient site for attachment to a linker.

Typically, peptide-type linkers can be prepared by forming a peptide bond between two or more amino acids and/or peptide fragments. Such peptide bonds can be prepared, for example, according to the liquid phase synthesis method (E. Schroder and K. Lubke "The Peptides", volume 1 (1965) 76-136, Academic Press) which is well known in the field of peptide chemistry.

In another embodiment, the linker may be substituted with groups which modulated solubility or reactivity. For example, a charged substituent such as sulfonate (SO3-) or ammonium or a polymer such as PEG, may increase water solubility of the reagent and facilitate the coupling reaction of the linker reagent with the antigen (hapten) or the drug moiety, or facilitate the coupling reaction depending on the synthetic route employed.

The conjugates comprising a non-sortase motif moiety as reported herein expressly contemplate, but are not limited to, complexes prepared with linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate), and including bis-maleimide reagents: DTME, BMB, BMDB, BMH, BMOE, BM(PEO) 3, and BM(PEO)4, which are commercially available from Pierce Biotechnology, Inc. Bis-maleimide reagents allow the attachment of e.g. a thiol group to a thiol-containing drug moiety, label, or linker intermediate, in a sequential or concurrent fashion. Other functional groups besides maleimide, which are reactive with e.g. a thiol group, include iodoacetamide, bromoacetamide, vinyl pyridine, disulfide, pyridyl disulfide, isocyanate, and isothiocyanate.

Exemplary linker include a valine-citrulline (val-cit or vc) dipeptide linker reagent having a maleimide stretcher and a para-aminobenzylcarbamoyl (PAB) self-immolative spacer, and a phe-lys (Mtr) dipeptide linker reagent having a maleimide Stretcher unit and a p-amino benzyl self-immolative spacer.

Cysteine thiol groups are nucleophilic and capable of reacting to form covalent bonds with electrophilic groups on linker reagents and the non-sortase motif moiety or the sortase amino acid sequence including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a haptenylated compound include, but are not limited to: amine, thiol, hydroxyl, hydrazide, oxime, hydrazine, hydrazine carboxylate, and arylhydrazide groups capable of reacting to form covalent bonds with electrophilic groups on linker moieties and linker reagents.

Coupling of Two Lipophilic Substrates

A DES comprising ChCl:Glycerol and 25% (v/v) of aqueous co-solvent was used for the conjugation of two both highly lipophilic compounds. Equimolar (0.15 mM) amounts of the substrates were employed and the reaction was analyzed over time. The time course is shown in FIG. 8. A conversion of 39% could be obtained in the DES comprising 25% aqueous co-solvent whereas in the 100% aqueous system no conversion could be detected.

Glycerol can Act as Nucleophile in the Deep Eutectic Solvents

A DES comprising ChCl:Glycerol and 25% (v/v) of aqueous co-solvent was used for the conjugation of two both highly lipophilic compounds.

It has been found that a second unexpected ligation product is formed. Mass spectroscopic analysis revealed the presence of a reaction product from the sortases intermediate (LCRed640-LPET-sortase (SEQ ID NO: 149)) with glycerol from the solvent. This high degree of promiscuity was unpredicted due to the fact that the substrate spectrum of the nucleophile is very narrow (Kruger, R. G., et al., Anal. Biochem. 326 (2004) 42-48; Baer, S., et al., Org. Biomol. Chem. 12 (2014) 2675-2685) and that even hydrolysis is rarely observed with wild type Sa-SrtA (Pritz, S. (2008) "Enzymatische Ligation von Peptiden, Peptidnucleinsauren and Proteinen"; Heck, T., et al., Bioconj. Chem. 25 (2014) 1492-1500).

Thus, one aspect as reported herein is a method for the enzymatic conjugation of a polypeptide with glycerol comprising the following step incubating
i) a polypeptide (optionally comprising within the 100 C-terminal amino acid residues) the amino acid sequence LPXTG (SEQ ID NO: 01, wherein X can be any amino acid residue) or LPXTA (SEQ ID NO: 41, wherein X can be any amino acid residue),
with
iii) a second polypeptide with sortase A activity,
in a deep eutectic solvent comprising choline chloride and glycerol
and thereby producing a polypeptide conjugated to glycerol.

In one embodiment the deep eutectic solvent is a mixture of choline chloride with glycerol at a molar ratio of 1:2 comprising about 25% (v/v) aqueous co-solvent.

VII. Recombinant Methods

Any polypeptide domain (e.g. a single chain antigen binding polypeptide such as a scFv, a scFab, or a darpin, or a multi chain antigen binding polypeptide such as a dsFv or a Fab) comprising an nucleophilic amino acid sequence at its N-terminus, such as e.g. an oligoglycine motif (GG (SEQ ID NO: 28), GGG (SEQ ID NO: 29), GGGG (SEQ ID NO: 30), GGGGG (SEQ ID NO: 31)) can be expressed and purified from the supernatant of eukaryotic cells (e.g. HEK293 cells, CHO cells). It does not matter if the polypeptide is an isolated polypeptide or comprised in a multimeric or heteromeric entity.

Suitable host cells for cloning or expression/secretion of polypeptide-encoding vectors include prokaryotic or eukaryotic cells described herein. For example, polypeptides may be produced in bacteria, in particular when glycosylation is not needed (see, e.g., U.S. Pat. Nos. 5,648,237, 5,789,199 and 5,840,523, Charlton, Methods in Molecular Biology 248 (2003) 245-254 (B. K. C. Lo, (ed.), Humana Press, Totowa, N.J.), describing expression of antibody fragments in *E. coli*). After expression, the polypeptide may be isolated from the bacterial cell paste in a soluble fraction or may be isolated from the insoluble fraction so called inclusion bodies which can be solubilized and refolded to bioactive forms. Thereafter the polypeptide can be further purified.

In addition to prokaryotes, eukaryotic microbes such as filamentous fungi or yeasts are suitable cloning or expression hosts for polypeptide-encoding vectors, including fungi and yeast strains whose glycosylation pathways have been "humanized", resulting in the production of a polypeptide with a partially or fully human glycosylation pattern (see e.g. Gerngross, Nat. Biotech. 22 (2004) 1409-1414, and Li, et al., Nat. Biotech. 24 (2006) 210-215).

Suitable host cells for the expression of glycosylated polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (see, e.g., U.S. Pat. Nos. 5,959,177, 6,040,498, 6,420,548, 7,125,978 and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are the COS-7 cell line (monkey kidney CV1 cell transformed by SV40); the HEK293 cell line (human embryonic kidney); the BHK cell line (baby hamster kidney); the TM4 mouse sertoli cell line (TM4 cells as described, e.g., in Mather, Biol. Reprod. 23 (1980) 243-251); the CV1 cell line (monkey kidney cell); the VERO-76 cell line (African green monkey kidney cell); the HELA cell line (human cervical carcinoma cell); the MDCK cell line (canine kidney cell); the BRL-3A cell line (buffalo rat liver cell); the W138 cell line (human lung cell); the HepG2 cell line (human liver cell); the MMT 060562 cell line (mouse mammary tumor cell); the TRI cell line (e.g. described in Mather, et al., Anal. N.Y. Acad. Sci. 383 (1982) 44-68); the MRCS cell line; and the FS4 cells-line. Other useful mammalian host cell lines include the CHO cell line (Chinese hamster ovary cell), including DHFR negative CHO cell lines (see e.g. Urlaub, et al., Proc. Natl. Acad. Sci. USA 77 (1980) 4216), and myeloma cell lines such as YO, NSO and Sp2/0 cell line. For a review of certain mammalian host cell lines suitable for polypeptide production, see, e.g., Yazaki, and Wu, Methods in Molecular Biology, Antibody Engineering 248 (2004) 255-268 (B. K. C. Lo, (ed.), Humana Press, Totowa, N.J.).

Figure 1:
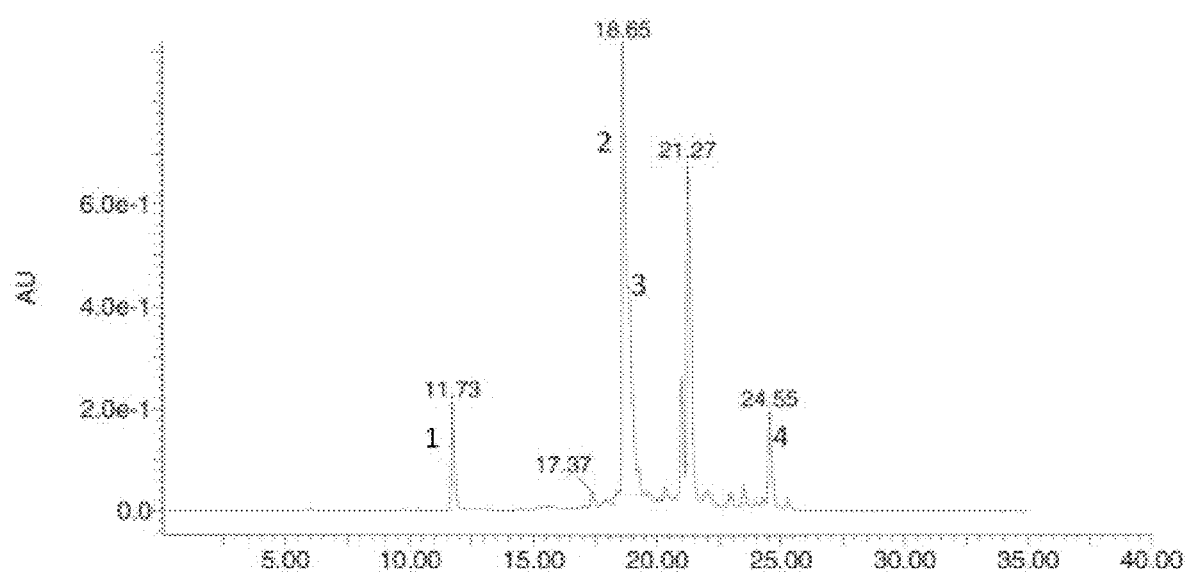
FIG. 1 Chromatogram of the reaction product of Example 3; 1: sortase; 2: GGGWW-BHQ2 (SEQ ID NO: 46); 3: LCR640-ULPETGGRRC (SEQ ID NO: 175)+B: GGGWW-BHQ2 (SEQ ID NO: 46); 4: LCR640-ULPETGGGWW-BHQ2 (SEQ ID NO: 176)
Figure 2A:
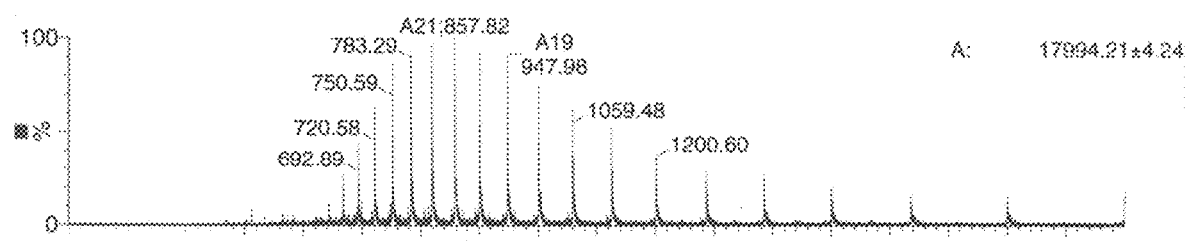
FIG. 2 Mass-spectrum of the peak of the chromatogram of FIG. 1; A:1, B:2, C:3, D:4.
Figure 2B:
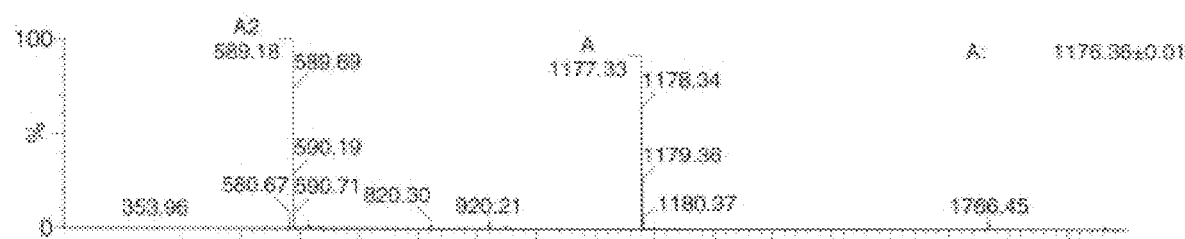
Figure 2C:
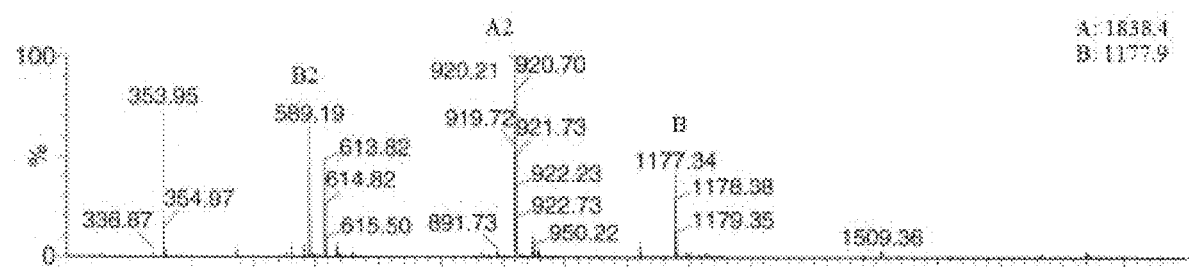
Figure 2D:
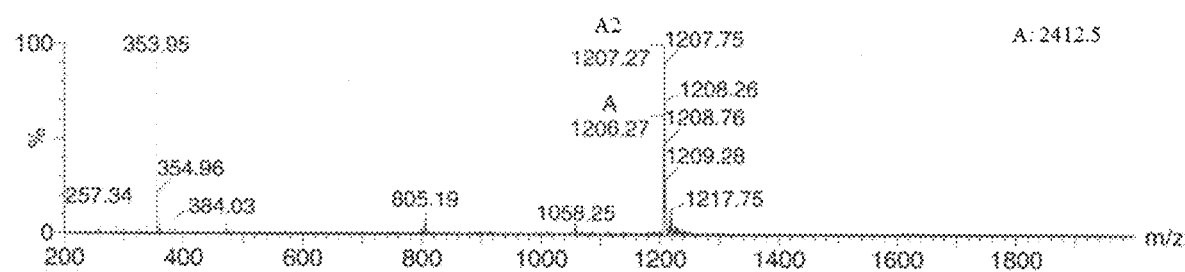

The following examples, figures and sequences are provided to aid the understanding of the present invention, the true scope of which is set forth in the appended claims. It is understood that modifications can be made in the procedures set forth without departing from the spirit of the invention.

EXAMPLES

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an E. coli plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Description of the Basic/Standard Mammalian Expression Plasmid

For the expression of a desired gene/protein (e.g. full length antibody heavy chain, full length antibody light chain, or an Fc-chain containing an oligoglycine at its N-terminus) a transcription unit comprising the following functional elements is used:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a gene/protein to be expressed (e.g. shortened Sortase A of *Staphylococcus aureus*), and
- the bovine growth hormone polyadenylation sequence (BGH pA).

Beside the expression unit/cassette including the desired gene to be expressed the basic/standard mammalian expression plasmid contains
- an origin of replication from the vector pUC18 which allows replication of this plasmid in *E. coli*, and
- a beta-lactamase gene which confers ampicillin resistance in *E. coli*.

Protein Determination

The protein concentration of purified polypeptides was determined by determining the optical density (OD) at 280 nm, using the molar extinction coefficient calculated on the basis of the amino acid sequence of the polypeptide.

Example 1

Generation of an Expression Plasmid for Sortase A

*Staphylococcus aureus* Derived Sortase A

The sortase gene encodes an N-terminally truncated *Staphylococcus aureus* sortase A (60-206) molecule (amino acid sequence of SEQ ID NO: 05).

The expression plasmid for the expression of sortase in *E. coli* cells comprised besides the sortase expression cassette an origin of replication from the vector pUC18, which allows replication of this plasmid in *E. coli*, and the URA3 gene as selectable marker, and the LacI gene to allow induction of transcription using IPTG.

The transcription unit of the sortase comprised the following functional elements:
- a T5 promoter,
- a purification tag,
- an N-terminally truncated *S. aureus* sortase A encoding nucleic acid, and
- the To and fd termination sequences.

The expression plasmid for the transient expression of sortase in HEK293 cells comprised besides the sortase expression cassette an origin of replication from the vector pUC18, which allows replication of this plasmid in *E. coli*, and a beta-lactamase gene which confers ampicillin resistance in *E. coli*.

The transcription unit of the sortase comprised the following functional elements:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a purification tag encoding nucleic acid,
- an N-terminally truncated *S. aureus* sortase A encoding nucleic acid, and
- the bovine growth hormone polyadenylation sequence (BGH pA).

The amino acid sequence of the mature sortase is

```
                                          (SEQ ID NO: 05)
QAKPQIPKDKSKVAGYIEIPDADIKEPVYPGPATPEQLNRGVSFAEENES

LDDQNISIAGHTFIDRPNYQFTNLKAAKKGSMVYFKVGNETRKYKMTSIR

DVKPTDVGVLDEQKGKDKQLTLITCDDYNEKTGVWEKRKIFVATEVK.
```

The purification tag has the amino acid sequence MRGSHHHHHHGS (SEQ ID NO: 32).

*Streptococcus pyogenes* Derived Sortase A

The sortase gene encodes an N-terminally truncated *Streptococcus pyogenes* sortase A molecule (amino acid sequence of SEQ ID NO: 06).

The expression plasmid for the expression of sortase in *E. coli* cells comprised besides the sortase expression cassette an origin of replication from the vector pUC18, which allows replication of this plasmid in *E. coli*, and the URA3 gene as selectable marker, and the LacI gene to allow induction of transcription using IPTG.

The transcription unit of the sortase comprised the following functional elements:
- a T5 promoter,
- a purification tag,
- an N-terminally truncated S. pyogenes sortase A encoding nucleic acid, and
- the To and fd termination sequences.

The expression plasmid for the transient expression of sortase in HEK293 cells comprised besides the sortase expression cassette an origin of replication from the vector pUC18, which allows replication of this plasmid in E. coli, and a beta-lactamase gene which confers ampicillin resistance in E. coli.

The transcription unit of the sortase comprised the following functional elements:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a purification tag encoding nucleic acid,
- an N-terminally truncated S. pyogenes sortase A encoding nucleic acid, and
- the bovine growth hormone polyadenylation sequence (BGH pA).

The amino acid sequence of the mature sortase is (SEQ ID NO: 06)
VLQAQMAAQQLPVIGGIAIPELGINLPIFKGLGNTELIVGAGTMKEEQVM

GGENNYSLASHHIFGITGSSQMLFSPLERAQNGMSIYLTDKEKIYEYIIK

DVFTVAPERVDVIDDTAGLKEVTLVTCTDIEATERIIVKGELKTEYDFDK

APADVLKAFNHSYNQVST.

The purification tag has the amino acid sequence MRGSHHHHHHGS (SEQ ID NO: 32).

Listeria monocytogenes Derived Sortase A

The sortase gene encodes an N-terminally truncated Listeria monocytogenes sortase A (73-222) molecule (amino acid sequence of SEQ ID NO: 38).

The expression plasmid for the expression of the truncated Listeria monocytogenes sortases in E. coli cells comprised besides the sortase expression cassette an origin of replication from the vector pUC18, which allows replication of this plasmid in E. coli, and the URA3 gene as selectable marker, and the Lad gene to allow induction of transcription using IPTG.

The transcription unit of the sortase comprised the following functional elements:
- a T5 promoter,
- a purification tag,
- the Listeria monocytogenes sortase A variant encoding nucleic acid, and
- the To and fd termination sequences.

The expression plasmid for the transient expression of truncated sortases in HEK293 cells comprised besides the sortase expression cassette an origin of replication from the vector pUC18, which allows replication of this plasmid in E. coli, and a beta-lactamase gene which confers ampicillin resistance in E. coli.

The expression plasmid for the transient expression of sortase in HEK293 cells comprised besides the sortase expression cassette an origin of replication from the vector pUC18, which allows replication of this plasmid in E. coli, and a beta-lactamase gene which confers ampicillin resistance in E. coli.

The transcription unit of the sortase comprised the following functional elements:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a purification tag encoding nucleic acid,
- an N-terminally truncated L. monocytogenes sortase A encoding nucleic acid, and
- the bovine growth hormone polyadenylation sequence (BGH pA).

The purification tag has the amino acid sequence MRGSHHHHHHGS (SEQ ID NO: 32).

Example 2

Transient Expression and Analytical Characterization

E. Coli:

The recombinant production of Sortase was performed by growing E. coli cells transformed with the respective Sortase expression plasmids to an OD578 of approx. 0.9 at 37° C. (pre-culture). At this OD578 of approx. 0.9 protein expression was induced by adding 2 mM IPTG and growing the cells for an additional 24 hours at 28° C. Thereafter, cells were harvested by centrifugation and lysed via high pressure using a homogenizer. Cell lysates were centrifuged to remove cell debris and subsequently the cell lysates were stored at reduced temperature (e.g. −80° C.) until purification. Soluble Sortase was purified using Ni-NTA chromatography followed by size exclusion chromatography. For depletion of endotoxins an anion exchange chromatography was performed in flow through mode. The protein concentration of sortase preparations was determined by measuring the optical density (OD) at 280 nm, using the molar extinction coefficient calculated on the basis of the amino acid sequence. Purity and integrity of sortase was determined by SDS-PAGE in the presence and absence of a reducing agent (5 mM 1,4-dithiothreitol) and staining with Coomassie brilliant blue.

The protein concentration was determined by measuring the optical density (OD) at 280 nm, using the molar extinction coefficient calculated on the basis of the amino acid sequence. Purity was analyzed by SDS-PAGE in the presence and absence of a reducing agent (5 mM 1,4-dithiothreitol) and staining with Coomassie brilliant blue.

HEK:

The recombinant production was performed by transient transfection of HEK293 cells (human embryonic kidney cell line 293-derived) cultivated in F17 Medium (Invitrogen Corp.). For transfection "293-Fectin" Transfection Reagent (Invitrogen) was used. Transfection was performed as specified in the manufacturer's instructions. Cell culture supernatants were harvested three to seven (3-7) days after transfection. Supernatants were stored at reduced temperature (e.g. −80° C.).

General information regarding the recombinant expression of human immunoglobulins in e.g. HEK293 cells is given in: Meissner, P. et al., Biotechnol. Bioeng. 75 (2001) 197-203.

The protein concentration was determined by measuring the optical density (OD) at 280 nm, using the molar extinction coefficient calculated on the basis of the amino acid sequence. Purity was analyzed by SDS-PAGE in the presence and absence of a reducing agent (5 mM 1,4-dithiotreitol) and staining with Coomassie brilliant blue.

Example 3

Sortase Mediated Transamidation in Deep Eutectic Solvents

DES-1 in this example is choline chloride mixed with glycerol at a molar ratio of 1:2.

As substrates the following components were used:
sortase-motif containing compound: LCR640-ULPETG-GRRC (SEQ ID NO: 175)
nucleophile: GGGWW-BHQ2 (SEQ ID NO: 46)

The two substrates which have a low solubility in water but good in DES were incubated with two different sortases and the activity determined.

Sortase 1: soluble *Staphylococcus aureus* Sortase A (SEQ ID NO: 05)
Sortase 2: soluble *Listeria monocytogenes* Sortase A (SEQ ID NO: 38)

The educts were dissolved in DES-1 (glycerol and choline chloride 2:1) to a final concentration of 0.5 mM. 1 mM Sortase 1 was stored in 50 mM Tris*HCl pH 7.5, 150 mM NaCl and 10 mM CaCl. This two solutions where mixed 19:1 (v/v) and incubated for 18 hours at 37° C.

Reaction mixture (10 µl) was injected on a Vydac C18 column of an LC-Ms system and separated with a 30 min. linear gradient to 100% buffer B (buffer A (v/v): 95% water, 5% acetonitrile, 0.1% trifluoro acetic acid (TFA); buffer B (v/v): 5% water, 95% Acetonitrile, 0.1% TFA). The respective chromatogram is shown in FIG. 1.

The Analysis of the reaction mixture with LC-MS shows in peak 4 the product of the sortase reaction.

Example 4

Sortase Mediated Transamidation in Aqueous Solution

A reaction mixture comprising 0.5 mM of the polypeptide LCR640-ULPETGGGRRC (LCR640 fluorophore conjugated to beta alanine (U); SEQ ID NO: 45) Fc-region fragment comprising a LPETG sortase motif (SEQ ID NO: 04), 1.5 mM of an N-terminal biotinylated N-terminal cysteine comprising peptide with the C-terminally biotinylated amino acid sequence CAAA (SEQ ID NO: 03) and 50 µM *Staphylococcus aureus* Sortase A in 50 mM Tris pH 7.5, 150 mM NaCl, 10 mM CaCl$_2$ was incubated at 37° C. for 18 h hours.

The reaction was analyzed without stopping.

Figure 3:
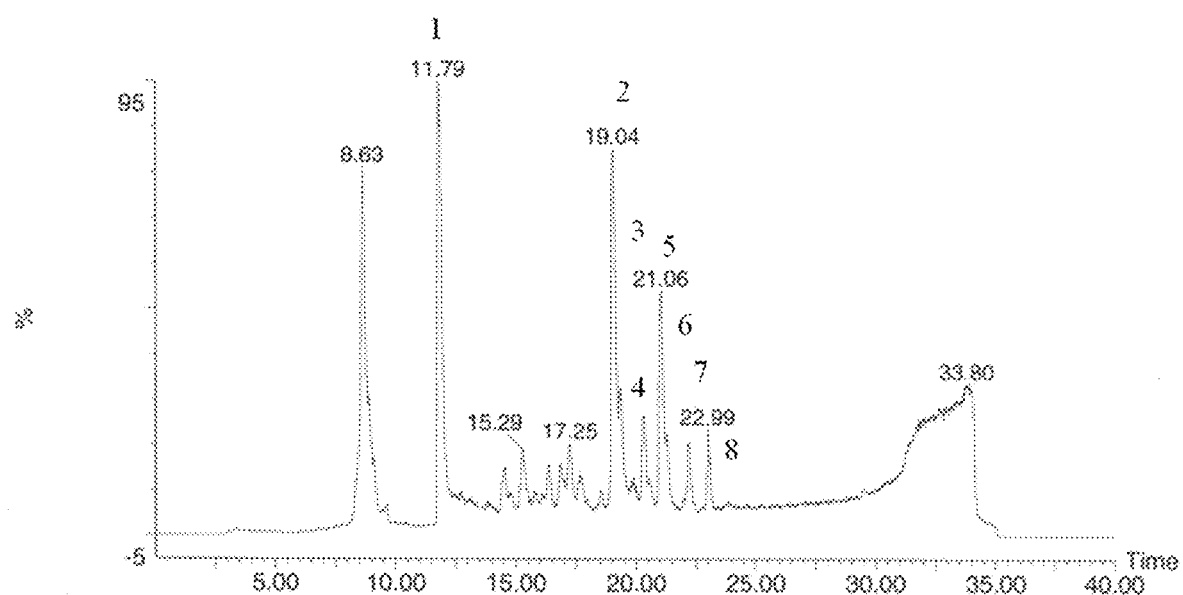
FIG. 3 Chromatogram of the reaction product of Example 4.
Figure 4A:
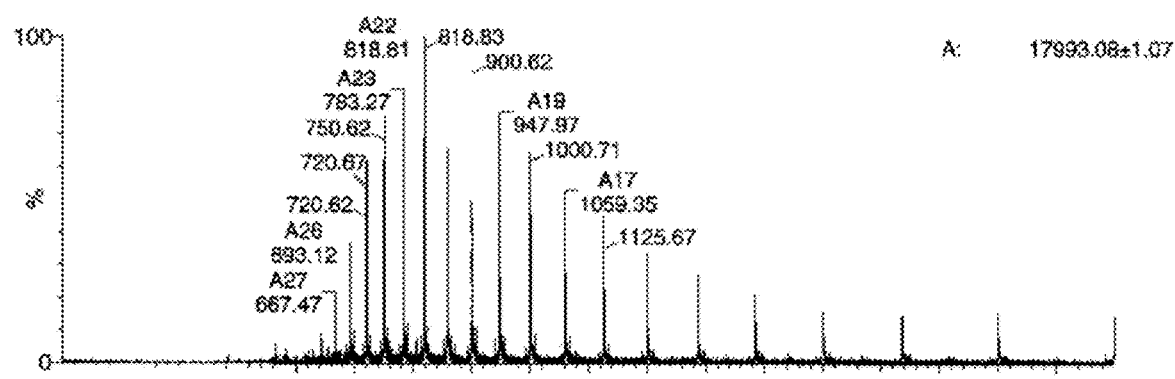
FIG. 4 Mass-spectrum of the peak of the chromatogram of FIG. 3; A:1, B:2, C:3, D:4, E:5, F:6, G:7, H:8.
Figure 4B:
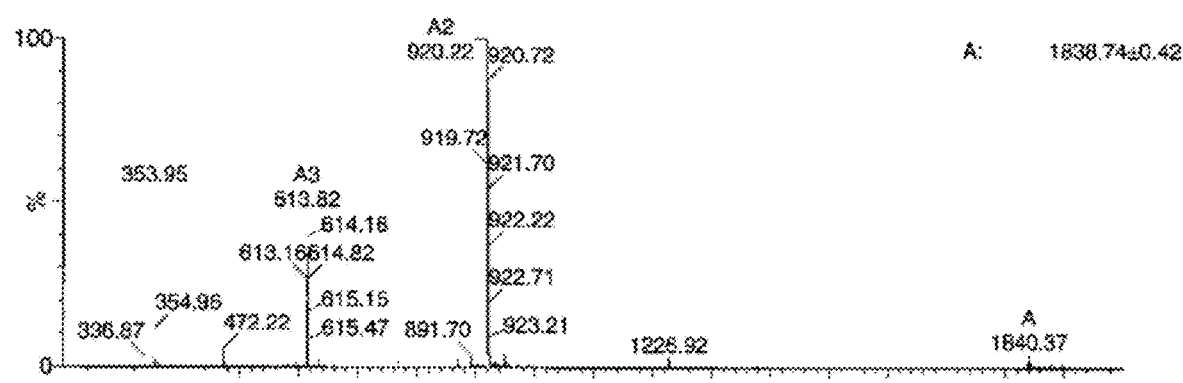
Figure 4C:
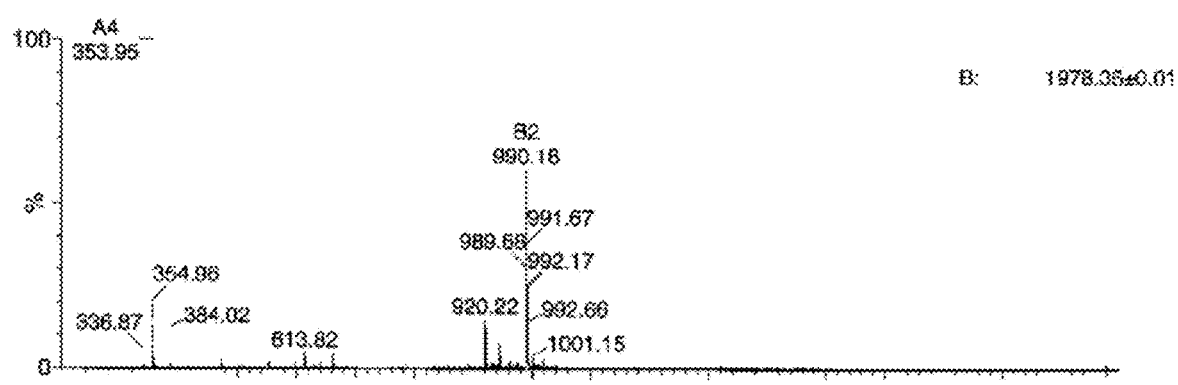
Figure 4D:
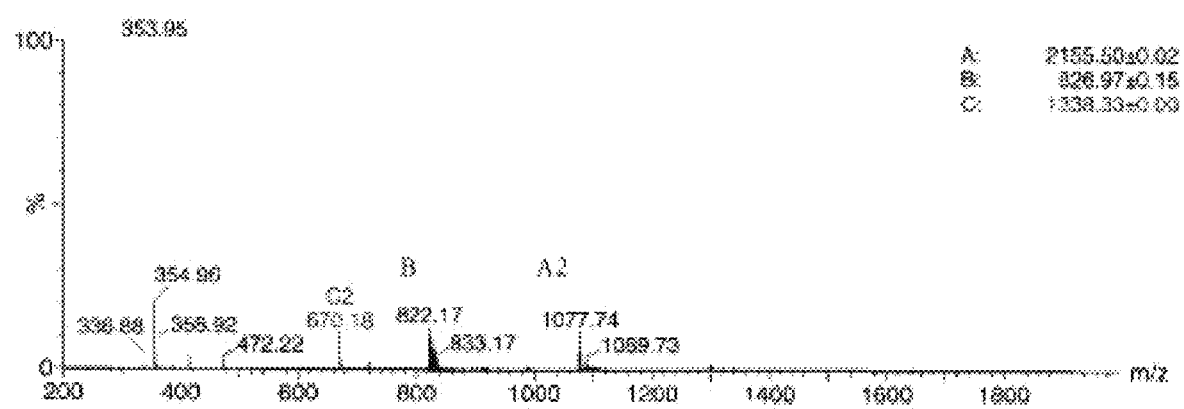
Figure 4E:
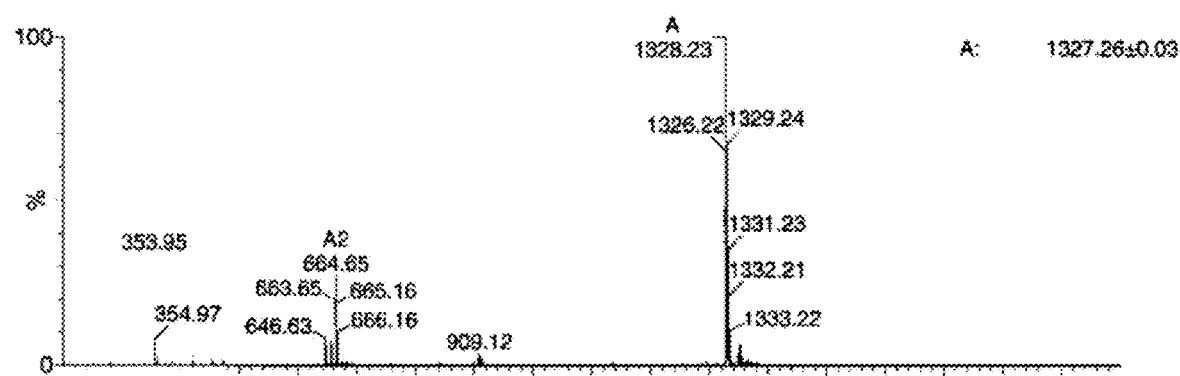
Figure 4F:
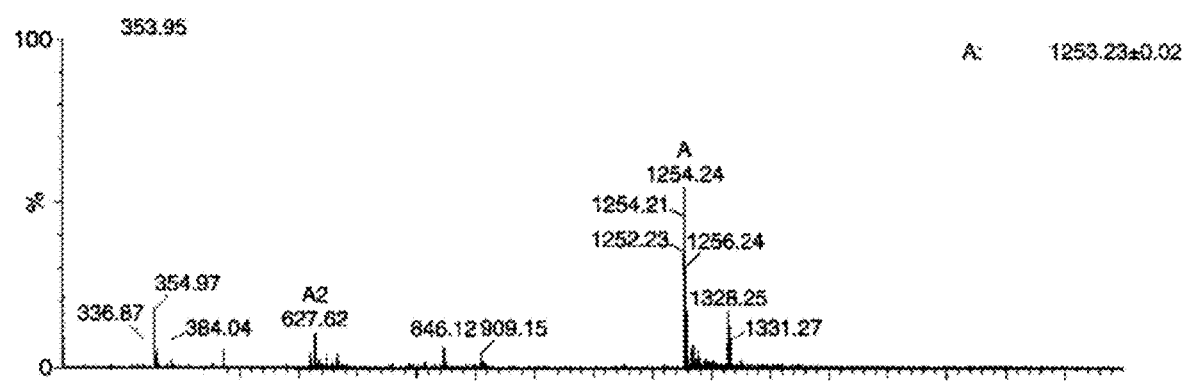
Figure 4G:
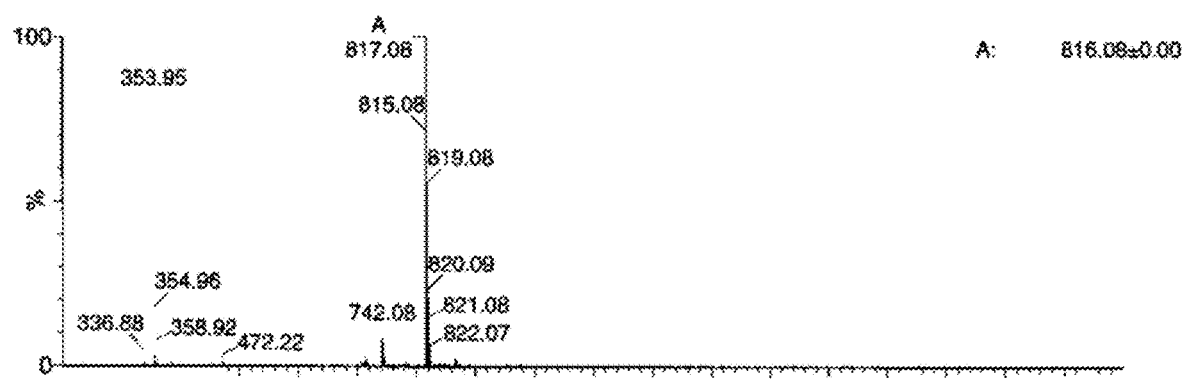
Figure 4H:
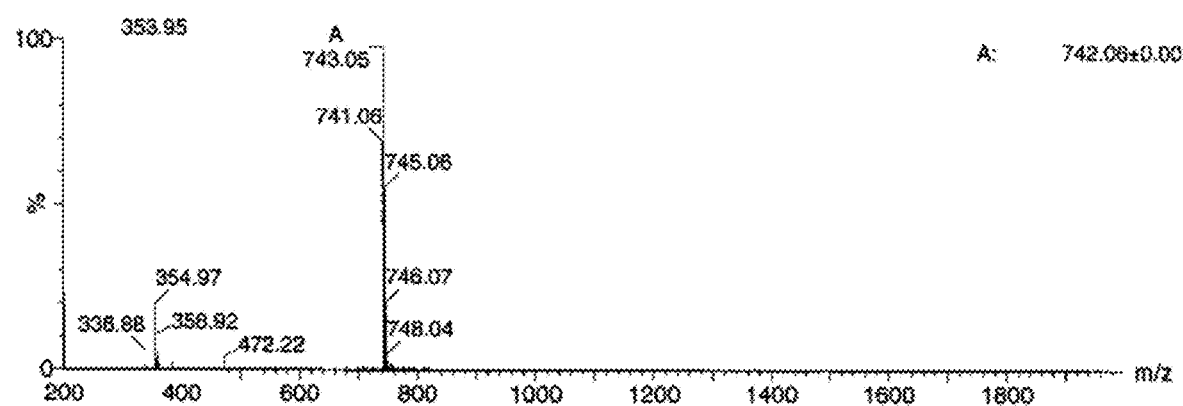

The samples (10 µl) were injected on a Vydac C18 column of an LC-Ms system and separated with a 30 min. linear gradient to 100% buffer B (buffer A (v/v): 95% water, 5% acetonitrile, 0.1% trifluoro acetic acid (TFA); buffer B (v/v): 5% water, 95% Acetonitrile, 0.1% TFA). The respective chromatogram is shown in FIG. 3.

The Analysis of the reaction mixture with LC-ESI-TOF MS in positive ion mode shows in peak 4 the product of the native chemical ligation reaction with the mass of 2155 Da.

The respective fragment pattern and masses are shown in the following Table. Table discloses SEQ ID NOS 45, 4, 179, 4, 4, and 180, respectively, in order of appearance.

| LCR-----U--------L------P-----E----T-------G----G----G----R-----R---C-NH |
|---|
| 1840 |
| 726 | 1114 |
| 1237 (1254) | 603 |
| 726 | 512 | 603 |

| | | |
|---|---|---|
| 1 | Educt: LPETG | 1840 |
| 2 | LCR-GGRR | 1329 |
| 3 | Educt: LPETG dimer | 3676 |
| 4 | Educt: G-Bio | 830 |
| 5 | Educt: C-Bio | 919 |
| 6 | LCR-LPETG-Bio | 2067 |
| 7 | LCR-LPETC-Bio | 2156 |

Example 5

Kinetic Assays

Two deep eutectic solvents have been tested in this example. DES-1 is choline chloride mixed with glycerol at a molar ratio of 1:2. DES-2 is choline chloride mixed with ethylene glycol at a molar ratio of 1:3.

The mixture comprising the 2 compounds was heated slowly over a flame and shaken until a clear, uniform solution was formed.

The liquid was then allowed to cool to room temperature. The yield was quantitative and the product had a melting point lower than room temperature.

Reaction 1:

| Ratio | Components |
|---|---|
| 1 | 1 mM St. au. SrtA (SEQ ID NO: 05), 50 mM Tris*HCl, pH 7.5, 200 mM NaCl, 10 mM CaCl$_2$ in water |
| 33 | 60 µM C-terminally biotinylated oligoglycine (GGGG, SEQ ID NO: 30) in DES |

| Ratio | Components |
|---|---|
| 16.5 | 60 µM glucose dehydrogenase (containing one of the substrates of the sortase reaction (LPXTG; SEQ ID NO: 04) in 50 mM Tris*HCl, pH 7.5, 200 mM NaCl, 10 mM CaCl$_2$ in water. |
| 49.5 | DES |

Reaction 2:

| Ratio | Components |
|---|---|
| 10 | 1 mM Listeria monocytogenes SrtA (SEQ ID NO: 38), 50 mM Tris*HCl pH 7.5, 200 mM NaCl, 10 mM CaCl$_2$ in water |
| 33 | 60 µM C-terminally biotinylated oligoglycine (GGGG, SEQ ID NO: 30) in DES |
| 16.5 | 60 µM glucose dehydrogenase (containing one of the substrates of the sortase reaction (LPXTG; SEQ ID NO: 04)) in 50 mM Tris*HCl, pH 7.5, 200 mM NaCl, 10 mM CaCl$_2$ in water. |
| 40.5 | DES |

The reaction mixture was incubated at 37° C. for 1, 2, 3 and up to 4 hours. The reaction was stopped by addition of a 20-fold excess of inhibition buffer (50 mM Tris, pH 7.5, 200 mM NaCl, 10 mM CaCl$_2$, 5 mM iodoacetamide). The stopped reaction mixture was centrifuged for 10 min at 5000×g. The supernatant (50 µL) was added to 100 µL of 50 mM Tris buffer (pH 7.5) comprising 200 mM NaCl, 10 mM CaCl$_2$ and Streptavidin coated magnetic beads. The mixture was incubated for 30 min at 30° C. with shaking at 200 rpm. Thereafter the magnetic beads were washed five times with 300 µL washing buffer each (50 mM Tris, pH 7.5, 200 mM NaCl, 10 mM CaCl$_2$, 5 mg/mL BSA, 0.1% Triton X-100) in V-bottom micro-titer-plates using a magnet and a vacuum pump. Afterwards the beads were resuspended in 100 µL citrate buffer (200 mM, pH 5.8) and 50 µL thereof are transferred to a new well. Thereto 150 µL test buffer (0.2 M sodium citrate, pH 5.8, 0.3 g/L 4-nitrosoanilin, 1 mM CaCl$_2$, 30 mM glucose) were added. The kinetic of the reporter enzyme was measured over a time period of 5 min at 620 nm.

In comparison the same reaction has been performed in an aqueous buffer system.

Figure 5:
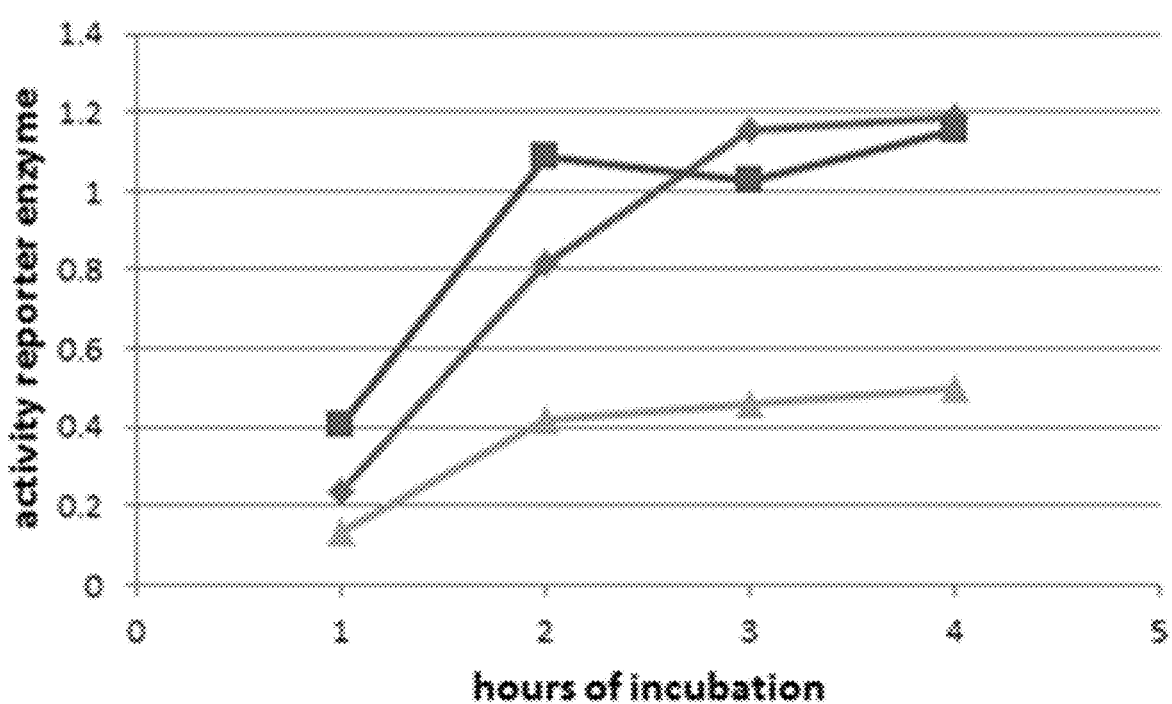
FIG. 5 Enzymatic activity of soluble St.au. SrtA using a REIA in different solvents; diamond: water; square: DES-1 (ChCl:G); triangle: DES-2 (ChCl:PE).
Figure 6:
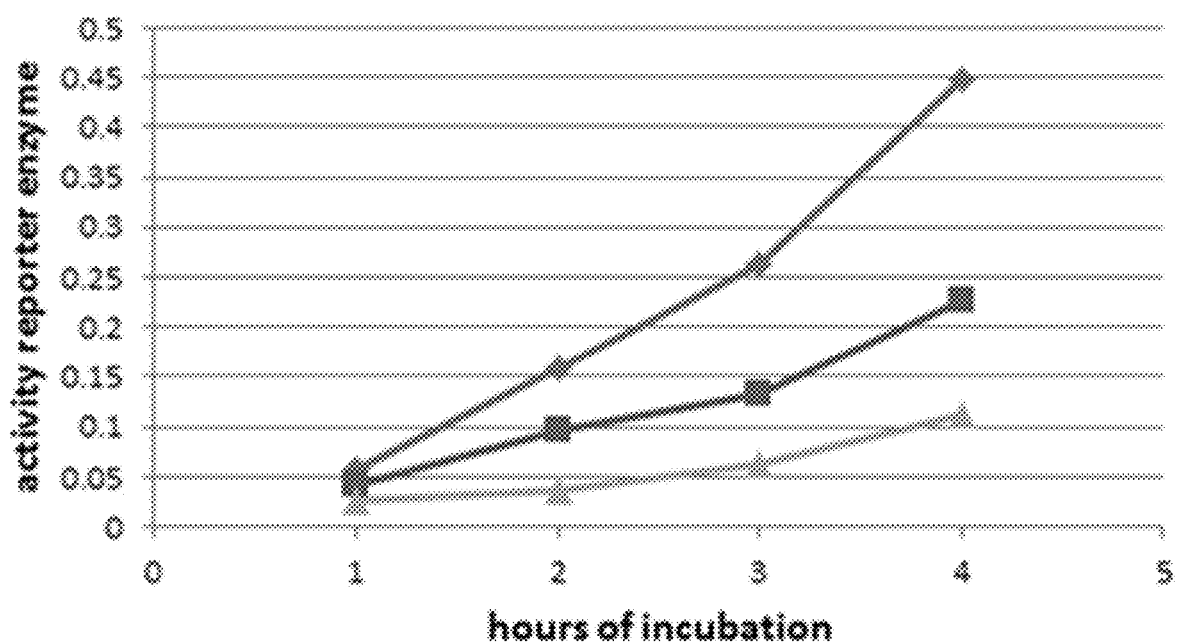
FIG. 6 Enzymatic activity of soluble *Listeria monocytogenes* SrtA using a REIA in different solvents; diamond: water; square: DES-1 (ChCl:G); triangle: DES-2 (ChCl:PE).
Figure 7:
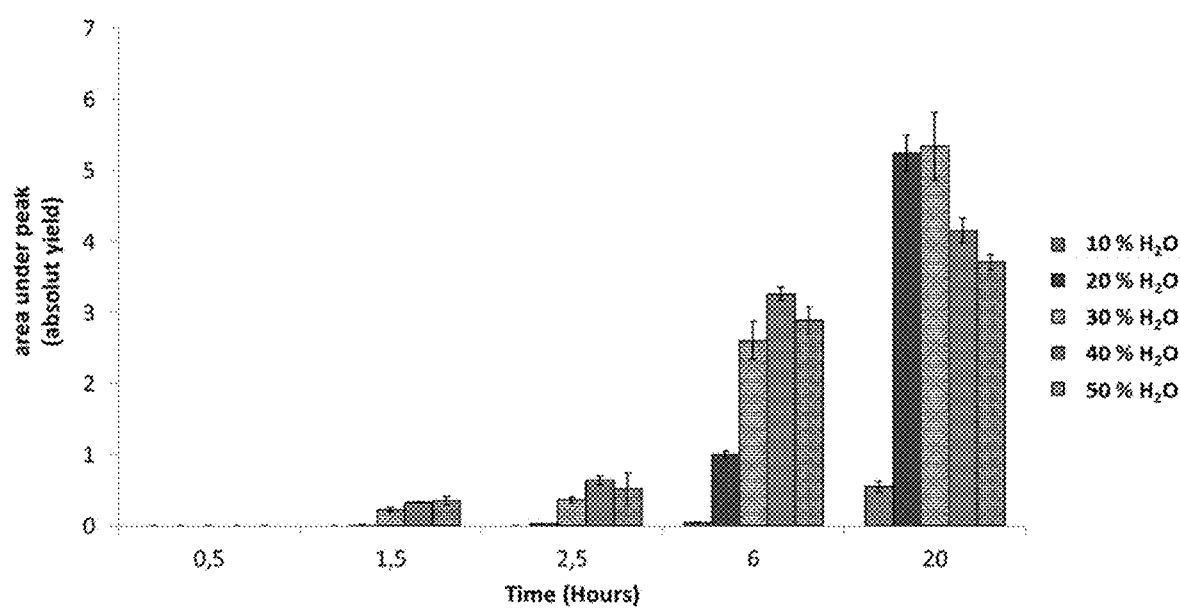
FIG. 7 Absolute reaction yields (area under peak) of sortase reaction in DES containing different amounts of aqueous co-solvent. Indicated mixtures of ChCl:Glycerol and water were prepared with 200 mM NaCl, 10 mM $CaCl_2$ and 50 mM Tris/HCl pH 7.5 and 0.05 mM Sa-SrtA, 0.5 mM LCRed640-LPETGGRRC (SEQ ID NO: 177) and 5 mM GGGG-Peg-Biotin (SEQ ID NO: 30). Samples were taken at indicated time points and analyzed by HPLC. Error bars represent the standard deviation of three independent measurements.
Figure 8:
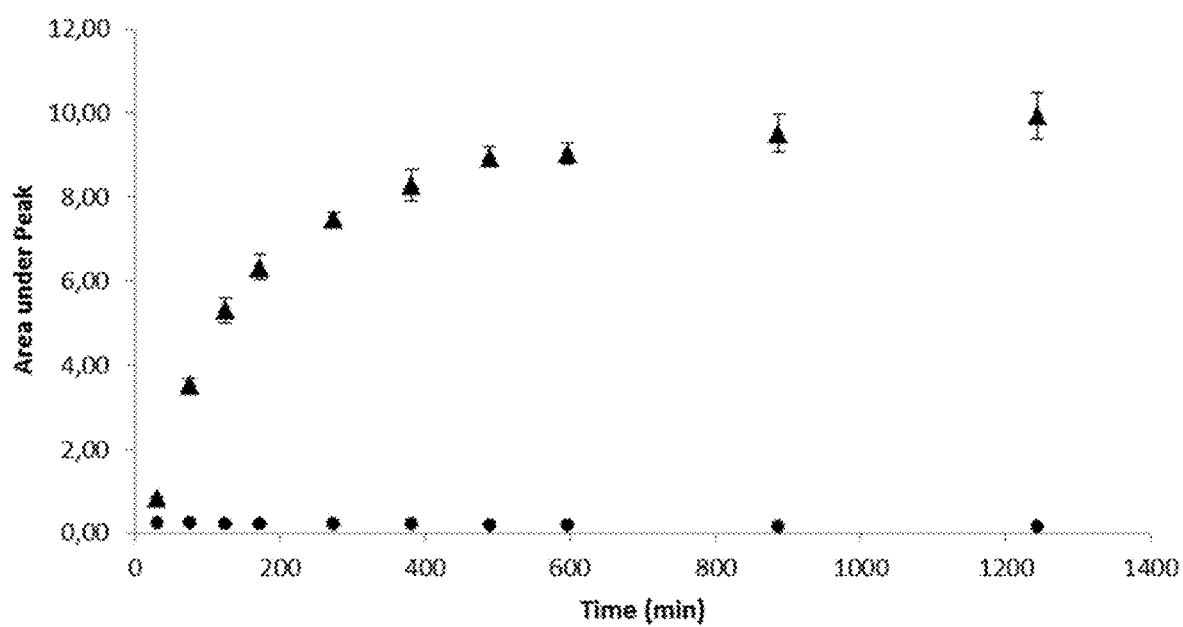
FIG. 8 Absolute reaction yields (area under peak) of sortase reactions in ChCl:Glycerol containing 25% and 100% water. Both solvents were prepared with 200 mM NaCl, 10 mM $CaCl_2$ and 50 mM Tris/HCl pH 7.5, 15 µM Sa-SrtA, 0.15 mM LCRed640-LPETGGRRC (SEQ ID NO: 177) and 0.15 mM GGWWK-BHQ2 (SEQ ID NO: 178). The reaction was analyzed at indicated time points for the generation of ligation product. Error bars represent the standard deviation of three independent measurements.

The results are shown in FIGS. 5 and 6.

Example 6

Reporter Immobilization Assay

Determination of Sortase A enzymatic activity can be done using a reporter immobilization assay (REIA) as reported in European Patent application EP14198535 and as outlined below.

Reaction Mixture:
- 20 µM polypeptide in question
- 100 µM nucleophile (GGGG/AAAA/CAAA (SEQ ID NOS 30, 181, and 3, respectively))
- 20 µM glucose dehydrogenase with C-terminal sortase motif (LPXTG (SEQ ID NO: 1))
- 250 mM MESNA
- 0.5 mM TCEP.

The glucose dehydrogenase is expressed and purified as described in WO 2007/118647.

The reaction mixture is prepared in 50 mM Tris-HCl buffer pH 7.5, 150 mM NaCl, 10 mM CaCl$_2$.

The reaction mixture is incubated at 37° C. for up to 60 hours. The reaction is stopped by addition of a 60-fold excess of inhibition buffer (50 mM Tris, pH 7.5, 200 mM NaCl, 10 mM CaCl$_2$, 5 mM iodoacetamide). The stopped reaction mixture is centrifuged for 10 min at 5000×g. The supernatant (50 µL) is added to 100 µL of 50 mM Tris buffer (pH 7.5) comprising 200 mM NaCl, 10 mM CaCl$_2$ and streptavidin coated magnetic beads. The mixture is incubated for 30 min at 30° C. with shaking at 200 rpm. Thereafter the magnetic beads are washed five times with 300 µL washing buffer each (50 mM Tris, pH 7.5, 200 mM NaCl, 10 mM CaCl$_2$, 5 mg/mL BSA, 0.1% Triton X-100) in V-bottom micro-titer-plates using a magnet and a vacuum pump. Afterwards the beads are resuspended in 100 µL citrate buffer and 80 µL thereof is transferred to a new well. Thereto 150 µL test buffer (0.2 M sodium citrate, pH 5.8, 0.3 g/L 4-nitrosoaniline, 1 mM CaCl$_2$, 30 mM glucose) are added. The kinetic of the reporter enzyme is measured over a time period of 5 min at 620 nm.

The generation of a signal is showing that the tested polypeptide has sortase A enzymatic activity.

Example 7

Reaction in DIFFERENT SOLVENTS

Trimethylamine, Acetone, Isopropanol, Acetonitrile, Dimethyl sulfoxide, DES (ChCl:Glycerol 1:2, ChCl:Ethylene glycol 1:3 and ChCl:2,3-Butanediol) and water were used as solvents. Beside Hexane the solvents supplemented with (15% water, 200 mM NaCl, 10 mM CaCl$_2$ and 50 mM Tris/HCl pH 7.5). 0.1 mM Sa-SrtA, 2 mM ULPETGGRR (SEQ ID NO: 174) and 4 mM GGGG-PEG-Biotin (SEQ ID NO: 30) were used. For Hexane the Sa-SrtA was used lyophilized. The reactions were incubated for 6 h at 37° C. at 800 rpm and stopped with the addition of 0.2 M HCl 1:1 (v:v) to the reaction mix. 20 µl was injected on a Aeris C18 Column of an HPLC-system and separated with a 31 min. linear gradient from 2% to 100% buffer B (buffer A (v/v): 95% water, 5% acetonitrile, 0.1% trifluoroacetic acid (TFA); buffer B (v/v): 5% water, 95% Acetonitrile, 0.1% TFA). Peaks were identified using a LC-MS-ESI-system under the same condition.

Example 8

Influence of WATER CONTENT

Mixtures of (ChCl:Glycerol) DES and water (10%, 20%, 30%, 40% and 50%) were prepared and additives were added to a final concentration of (200 mM NaCl, 10 mM CaCl2 and 50 mM Tris/HCl pH 7.5). 0.05 mM Sa-SrtA, 0.5 mM LCRed640-LPETGGRRC (SEQ ID NO: 177) and 5 mM GGGG-PEG-Biotin (SEQ ID NO: 30) was used. The reaction was stopped after 0.5 h, 1.5 h, 2.5 h, 6 h and 20 h with the addition of 0.2 M HCl 1:1 (v:v) with the reaction mix. 20 µl was injected on a Aeris C18 Column of an HPLC-system and separated with a 31 min. linear gradient from 2% to 100% buffer B (buffer A (v/v): 95% water, 5% acetonitrile, 0.1% trifluoroacetic acid (TFA); buffer B (v/v): 5% water, 95% acetonitrile, 0.1% TFA). Peaks were identified using a LC-MS-ESI-system. Retention times: 8.1 min Sort-tag (ULPETGGRR (SEQ ID NO: 174)), 8.6 min Nucleophile (GGGG-Peg-Biotin (SEQ ID NO: 30)), 10.2 ligation product (ULPETGGGG-Peg-Biotin (SEQ ID NO: 182)) and 13.5 min Sa-SrtA.

Example 9

Coupling of Two Lipophilic Substrates

A buffer containing 25% and 100% water in DES (ChCl:Glycerol) with (200 mM NaCl, 10 mM CaCl2 and 50 mM Tris/HCl pH 7.5) was used and 0.15 mM of both substrates (LCRed640-LPETGGRRC (SEQ ID NO: 177) and GGWWK-BHQ2 (SEQ ID NO: 178)) were weighed in. The mixture was shaken for 1 h at 40° C. and centrifuged. To start the reaction 30 μM Sa-SrtA were added to the supernatant and incubated at 37° C. At indicated time points (20 μl) was injected on a Aeris C18 Column of an HPLC-system and separated with a 8 min. linear gradient from 5% to 48% and in 15 min from 48% to 95% buffer B (buffer A (v/v): 95% water, 5% acetonitrile, 0.1% trifluoroacetic acid (TFA); buffer B (v/v): 5% water, 95%, 0.1% TFA). Peaks were identified using a LC-MS-ESI-system.

Although the foregoing invention has been described in some detail by way of illustration and example for purposes of clarity of understanding, the descriptions and examples should not be construed as limiting the scope of the invention.

The invention claimed is:

1. A method for the enzymatic production of a polypeptide comprising incubating in a deep eutectic solvent
   i) a first polypeptide comprising the amino acid sequence LPXTA (SEQ ID NO: 41), wherein X can be any amino acid residue,
   a second polypeptide that has i) a glycinyl, an alaninyl, or a cysteinyl compound at its N-terminus, or ii) an oligoglycine, or oligoalanine, or a cysteine amino acid residue followed by one to three glycine or alanine amino acid residues at its N-terminus, or iii) a lysine amino acid residue within its 5 N-terminal amino acid residues, and
   iii) *Staphylococcus aureus* sortase A or *Listeria monocytogenes* sortase A,
   wherein the deep eutectic solvent is a mixture of choline chloride with glycerol at a molar ratio of 1:2 comprising up to 5% (v/v) aqueous co-solvent;
thereby producing a polypeptide.

2. The method according to claim 1, wherein the second polypeptide has at its N-terminus the amino acid sequence GGG, AAA, CGG, CAA, KGG, or KAA.

3. The method according to claim 1, wherein the first polypeptide comprises at its C-terminus the amino acid sequence LPXTA (SEQ ID NO: 41), wherein X can be any amino acid residue.

4. The method according to claim 3, wherein the first polypeptide comprises at its C-terminus the amino acid sequence LPETA (SEQ ID NO: 42).

5. The method according to claim 1, wherein the first polypeptide and the second polypeptide are independently of each other selected from an antibody variable domain, an antibody heavy chain Fab-fragment, an antibody Fc-region, a tag, a linker, and a non-sortase motif moiety.

6. A method for the enzymatic production of a polypeptide comprising incubating in a deep eutectic solvent
   i) a first polypeptide comprising the amino acid sequence LPXTG (SEQ ID NO: 01), wherein X can be any amino acid residue or LPXTA (SEQ ID NO: 41), wherein X can be any amino acid residue,
   ii) a second polypeptide that has i) a glycinyl or a cysteinyl compound at its N-terminus, or ii) an oligoglycine or iii) a lysine amino acid residue within its 5 N-terminal amino acid residues, and
   iii) *Staphylococcus aureus* sortase A or *Listeria monocytogenes* sortase A,
   wherein the deep eutectic solvent is a mixture of choline chloride with glycerol at a molar ratio of 1:2 comprising up to 5% (v/v) aqueous co-solvent;
thereby producing a polypeptide.

7. The method according to claim 6, wherein the second polypeptide has at its N-terminus the amino acid sequence GGG, KGG, or KAA.

8. The method according to claim 6, wherein the first polypeptide comprises at its C-terminus the amino acid sequence LPXTG (SEQ ID NO: 01), wherein X can be any amino acid residue or LPXTA (SEQ ID NO: 41), wherein X can be any amino acid residue.

9. The method according to claim 8, wherein the first polypeptide comprises at its C-terminus the amino acid sequence LPETG (SEQ ID NO: 04) or LPETA (SEQ ID NO: 42).

10. The method according to claim 6, wherein the first polypeptide and the second polypeptide are independently of each other selected from an antibody variable domain, an antibody heavy chain Fab-fragment, an antibody Fc-region, a tag, a linker, and a non-sortase motif moiety.

* * * * *